(12) United States Patent
Carreira

(10) Patent No.: US 7,790,882 B2
(45) Date of Patent: Sep. 7, 2010

(54) MONOPHOSPHINE COMPOUND, TRANSITION METAL COMPLEX THEREOF AND PRODUCTION METHOD OF OPTICALLY ACTIVE COMPOUND USING THE COMPLEX AS ASYMMETRIC CATALYST

(75) Inventor: Erick M. Carreira, c/o Laboratory of Organic Chemistry ETH-Hoenggerberg, Zurich (CH)

(73) Assignees: Erick M. Carreira, Zurich (CH); Sumitomo Chemical Company, Limited, Tokyo (JP)

( * ) Notice: Subject to any disclaimer, the term of this patent is extended or adjusted under 35 U.S.C. 154(b) by 1124 days.

(21) Appl. No.: 11/149,643

(22) Filed: Jun. 10, 2005

(65) Prior Publication Data

US 2005/0277772 A1    Dec. 15, 2005

Related U.S. Application Data

(60) Provisional application No. 60/578,735, filed on Jun. 10, 2004.

(51) Int. Cl.
*C07F 1/08* (2006.01)
*C07F 15/00* (2006.01)
*C07F 17/00* (2006.01)
*C07F 9/6509* (2006.01)
*C07B 53/00* (2006.01)

(52) U.S. Cl. ............... 544/225; 544/229; 544/232

(58) Field of Classification Search ............... 544/225, 544/229, 232
See application file for complete search history.

(56) References Cited

U.S. PATENT DOCUMENTS 3,389,137 A * 6/1968 Mosby et al. ............... 544/243

FOREIGN PATENT DOCUMENTS

WO    WO 2006/004589 A2    1/2006

OTHER PUBLICATIONS

Costa, et al., Tetrahedron 61 (2005) 6442-6446.*
Alexakis, et al., JACS, 2002, 124, 5262-5263.*
Alexakis, et al., Tetrahedron: Asymmetry, vol. 16, # 22, Nov. 14, 2005, 3672-75.*
Ramirez, et al., Tetrahedron: Asymmetry, vol. 16, # 7, Apr. 4, 2005, 1289-94.*
Dong, et al., Tetrahedron: Asymmetry, vol. 15, # 10, May 24, 2004, 1537-1540.*
Meuzelaar, et al., Tetrahedron, vol. 56, # 18, Apr. 28, 2000, 2895-2903.*
Kim, et al. Acc. Chem. Res., 34 (12), 955-962, 2001.*
Alcock et al., *Tetrahedron Asymmetry*, 4(4): 743-756 (1993).
Brown et al., *J. Chem. Soc. Chem. Commun.*: 1673-1674 (1993).
Chen et al., *J. Am. Chem. Soc.*, 125: 10174-10175 (2003).
Connolly et al., *J. Org. Chem.*, 69: 6572-6589 (2004).
Gommermann et al., *Angew. Chem. Int. Ed.*, 42: 5763-5766 (2003).
Knöpfel et al., *Angew. Chem.*, 116: 6097-6099 (2004).
Knöpfel et al., *J. Am. Chem. Soc.*, 127: 9682-9683 and Supplementary Material S1-S18 (2005).
Koradin et al., *Angew. Chem. Int. Ed.*, 41(14): 2535-2538 (2002).
Morgan et al., *J. Am. Chem. Soc.*, 125: 8702-8703 (2003).
Chen et al., *J. Org. Chem.*, 64(26): 9704-9710 (Dec. 24, 1999).
Fernandez et al., *Chem. Eur. J.*, 6(10): 1840-1846 (May 15, 2000).
Knöpfel et al., *Angew. Chem. Int. Ed.*, 43(44): 5971-5973 (Nov. 12, 2004).
Knöpfel et al., *J. Am. Chem. Soc.*, 125(20): 6054-6055 (May 21, 2003).

* cited by examiner

*Primary Examiner*—James O Wilson
*Assistant Examiner*—Cecilia M Jaisle
(74) *Attorney, Agent, or Firm*—Leydig, Voit & Mayer, Ltd.

(57)    ABSTRACT

The present invention provides a compound represented by the formula (I):

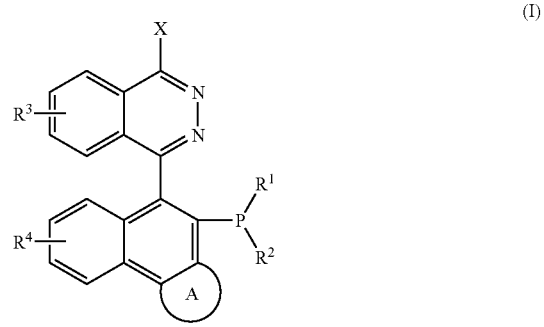

wherein ring A is void or a benzene ring optionally having substituent(s), $R^1$ and $R^2$ are each independently a phenyl group optionally having substituent(s), a cyclohexyl group and the like, $R^3$ and $R^4$ are each independently a hydrogen atom, a halogen atom, a lower alkyl group, a lower alkoxy group and the like, and X is a residue represented by —$OR^5$ or —$NHR^6$ wherein $R^5$ and $R^6$ are a lower alkyl group optionally having substituent(s), an aralkyl group optionally having substituent(s) and the like, a asymmetric transition metal complex containing the compound as a ligand and a production method of optically active compound using the complex as an asymmetric catalyst.

14 Claims, No Drawings

MONOPHOSPHINE COMPOUND, TRANSITION METAL COMPLEX THEREOF AND PRODUCTION METHOD OF OPTICALLY ACTIVE COMPOUND USING THE COMPLEX AS ASYMMETRIC CATALYST

TECHNICAL FIELD OF THE INVENTION

The present invention relates to a novel monophosphine compound, an asymmetric transition metal complex comprising the monophosphine compound as a ligand and a production method of an optically active compound which uses the asymmetric transition metal complex as an asymmetric catalyst.

BACKGROUND OF THE INVENTION

Heretofore, reports have been documented on many asymmetric transition metal complexes as catalysts for asymmetric catalyst reactions, and a number of asymmetric ligands therefor have been developed.

Many of the asymmetric ligands are asymmetric diphosphine compounds represented by 2,2'-bis(diphenylphosphino)-1,1'-binaphthyl (BINAP), and they are reported to achieve extremely superior selectivity and yield particularly in asymmetric hydrogenation reaction. However, application to asymmetric reactions other than the asymmetric hydrogenation reactions of asymmetric transition metal complexes using these asymmetric diphosphine compounds is limited. While application to the asymmetric cyclization reaction, asymmetric aldol reaction and the like has been reported (The Journal of Organic Chemistry, 2000, vol. 65, p. 5806-5816; Journal of the American Chemical Society, 2000, vol. 122, p. 4528-4529; Tetrahedron Letters, 2000, vol. 41, p. 891-895; Synlett, 1999, vol. 5, p. 605-607; Tetrahedron Asymmetry, 2000, vol. 11, p. 3561-3568), selectivity and yield are not entirely sufficient. Particularly, application to asymmetric addition reaction, asymmetric conjugate addition reaction and asymmetric hydroboration reaction highly useful as asymmetric reactions is not entirely sufficient in the selectivity and yield, and applicable substrates are limited.

Tetrahedron Asymmetry, 1993, vol. 4, pp. 743-756 discloses, as a monophosphine ligand for an asymmetric transition metal complexes, 1-(2-diphenylphosphanylnaphthalen-1-yl)isoquinoline (hereinafter sometimes to be abbreviated as QUINAP), and it has been reported that an asymmetric transition metal complex having QUINAP as a ligand catalyzes, with high selectivity, an asymmetric hydroboration reaction (Journal of the Chemical Society, Chemical Communications, 1993, p. 1673-1674) or asymmetric addition reaction of alkynes to enamine or iminium ion (Angewandte Chemie International Edition, 2002, vol. 41, pp. 2535-2541 and Angewandte Chemie International Edition, 2003, vol. 42, pp. 5763-5766), which are difficult by the use of BINAP etc.

SUMMARY OF THE INVENTION

However, QUINAP is impractical since its preparation requires as many as 7 steps to give a racemate, making the cost extremely high, formation of a diastereomer complex with 0.5 equivalent of an asymmetric palladium compound is necessary for its optical resolution (Angewandte Chemie International Edition, 2002, vol. 41, p. 2535-2541.), and separation and purification of the diastereomer complex is difficult due to easy racemization of asymmetric palladium compound.

It is therefore an object of the present invention to enable highly selective asymmetric addition reaction, asymmetric conjugate addition reaction, asymmetric hydroboration reaction and the like, to which an asymmetric transition metal complex using conventional BINAP and the like was difficult to be applied, and provide an asymmetric ligand that can be prepared easily and economically and an asymmetric transition metal complex containing the same.

The present inventors have conducted intensive studies in an attempt to solve the aforementioned problems and found that, the use, as a ligand, of an asymmetric transition metal complex containing a compound having a phthalazine ring having substituent(s) on the 4-position, instead of the isoquinoline ring of QUINAP, can achieve at least the same level of selectivity and yield as does QUINAP, and that the ligand can be easily prepared from a known compound, which resulted in the completion of the present invention.

Accordingly, the present invention provides the following.

[1] A compound represented by the formula (I):

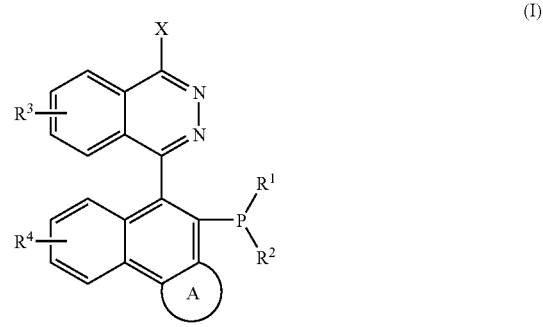

wherein ring A is void or a benzene ring optionally having substituent(s), $R^1$ and $R^2$ are each independently a phenyl group optionally having substituent(s), a cyclohexyl group, a 2-furyl group or a 3-furyl group, $R^3$ and $R^4$ are each independently a hydrogen atom, a halogen atom, a lower alkyl group, a lower alkoxy group, a cycloalkyl group optionally having substituent(s), an aralkyl group optionally having substituent(s) or an aryl group optionally having substituent(s), and X is a residue represented by —$OR^5$ or —$NHR^6$ wherein $R^5$ and $R^6$ are each a lower alkyl group optionally having substituent(s), an aralkyl group optionally having substituent(s), an aryl group optionally having substituent(s) or a heteroaryl group optionally having substituent(s) (hereinafter to be also referred to as compound (I)).

[2] The compound of the above-mentioned [1], wherein $R^1$ and $R^2$ are each independently a phenyl group, a tolyl group or a cyclohexyl group.

[3] The compound of the above-mentioned [1] or [2], wherein $R^5$ or $R^6$ is a residue having an asymmetric center.

[4] The compound of any of the above-mentioned [1] to [3], which is an optically active form.

[5] An asymmetric transition metal complex comprising the compound of the above-mentioned [4] as a ligand.

[6] The asymmetric transition metal complex of the above-mentioned [5], wherein the transition metal is a metal selected from Ru, Pd, Rh, Cu and Ag.

[7] The asymmetric transition metal complex of the above-mentioned [5] or [6], which is prepared by reacting the compound of the above-mentioned [4] with a transition metal salt or a complex thereof.

[8] The asymmetric transition metal complex of the above-mentioned [7], wherein the transition metal salt or a complex thereof is selected from $CuX^1$, $Cu(X^1)_2$, $Rh(cod)_2X^1$, (nbd) Rh (acac), $CyRu (X^1)_2$ and $AgX^1$ wherein $X^1$ is a counter ion selected from a halogen atom, $BF_4$, acetoxy, $SbF_6$, $PF_6$ and $OSO_2CF_3$, cod is a 1,5-cyclooctadiene, nbd is a norbornadiene, Cy is a cymene, and acac is an acetylacetone.

[9] A production method of an optically active compound by an asymmetric reaction, which comprises contacting a substrate with the asymmetric transition metal complex of any of the above-mentioned [5] to [8].

[10] The production method of the above-mentioned [9], wherein the asymmetric reaction is an asymmetric addition reaction, an asymmetric conjugate addition reaction, an asymmetric hydroboration reaction, an asymmetric diboration reaction, an asymmetric [3+2] cyclization reaction, an asymmetric substitution reaction or an asymmetric Diels-Alder [4+2] cyclization reaction.

[11] The production method of the above-mentioned [10], wherein the asymmetric reaction is an asymmetric addition reaction.

[12] The production method of the above-mentioned [11], wherein the asymmetric transition metal complex is prepared by reacting the compound of the above-mentioned [4] with $CuX^1$ wherein $X^1$ is as defined above.

[13] The production method of the above-mentioned [11] or [12], wherein the substrate comprises a compound represented by the formula (II): $R^7CHO$ (II) wherein $R^7$ is a lower alkyl group optionally having substituent(s), an aryl group optionally having substituent(s), a cycloalkyl group optionally having substituent(s), a lower alkenyl group optionally having substituent(s), a lower alkynyl group optionally having substituent(s), an aralkyl group optionally having substituent(s) or a heteroaryl group optionally having substituent(s) (hereinafter to be also referred to as compound (II)), a compound represented by the formula (III): $HNR^8R^9$ (III) wherein $R^8$ and $R^9$ are each independently a lower alkyl group optionally having substituent(s), a lower alkenyl group optionally having substituent(s), a cycloalkyl group optionally having substituent(s), an aralkyl group optionally having substituent(s), an aryl group optionally having substituent(s) or a heteroaryl group optionally having substituent(s), or $R^8$ and $R^9$ may form, together with the adjacent nitrogen atom, an aliphatic nitrogen-containing heterocycle optionally having substituent(s) (hereinafter to be also referred to as compound (III)), and a compound represented by the formula (IV): $HC\equiv CR^{10}$ (IV) wherein $R^{10}$ is a hydrogen atom, a lower alkyl group optionally having substituent(s), an aryl group optionally having substituent(s), a trialkylsilyl group, a cycloalkyl group optionally having substituent(s), an aralkyl group optionally having substituent(s) or a heteroaryl group optionally having substituent(s) (hereinafter to be also referred to as compound (IV)), and the optically active compound is a compound represented by the formula (V):

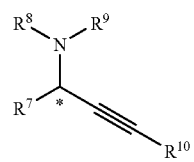

wherein $R^7$, $R^8$, $R^9$ and $R^{10}$ are as defined above and * shows an asymmetric carbon (hereinafter to be also referred to as compound (V)).

[14] The production method of the above-mentioned [13], wherein $R^8$ and $R^9$ form a 4-piperidinone together with the adjacent nitrogen atom.

[15] A production method of a compound represented by the formula (Vb):

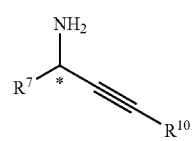

wherein each symbol is as defined above (hereinafter to be also referred to as compound (Vb)) or a salt thereof, which comprises deprotecting a compound represented by the formula (Va):

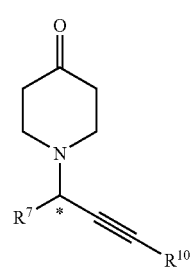

wherein each symbol is as defined above (hereinafter to be also referred to as compound (Va)) or a salt thereof, which is produced according to the method of the above-mentioned [14].

[16] The production method of the above-mentioned [10], wherein the asymmetric reaction is an asymmetric conjugate addition reaction.

[17] The production method of the above-mentioned [16], wherein the asymmetric transition metal complex is prepared by reacting the compound of the above-mentioned [4], and $Cu(X^1)_2$ wherein $X^1$ is a counter ion selected from a halogen atom, $BF_4$, acetoxy, $SbF_6$, $PF_6$ and $OSO_2CF_3$ with a reducing agent.

[18] The production method of the above-mentioned [16] or [17], wherein the substrate comprises a compound represented by the formula (XXVI):

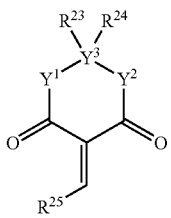

wherein $Y^1$ and $Y^2$ are each independently an oxygen atom or $NR^{26}$ wherein $R^{26}$ is a lower alkyl group optionally having substituent(s), an aryl group optionally having substituent(s), an aralkyl group optionally having substituent(s) or a heteroaryl group optionally having substituent(s), $Y^3$ is a carbon atom or a sulfur atom, $R^{23}$ and $R^{24}$ are each independently a hydrogen atom, an oxo, or $R^{23}$ and $R^{24}$ may form an oxo in combination, a lower alkyl group optionally having substituent(s), an aryl group optionally having substituent(s), an aralkyl group optionally having substituent(s) or a heteroaryl group optionally having substituent(s), and $R^{25}$ is a lower alkyl group optionally having substituent(s), a cycloalkyl group optionally having substituent(s), an aryl group optionally having substituent(s), an aralkyl group optionally having substituent(s), a heteroaryl group optionally having substituent(s), a heteroarylalkyl group optionally having substituent(s), a heteroalkyl group optionally having substituent(s), $-OCOR^{27}$, $-NR^{28}R^{29}$ or $-SR^{30}$ wherein $R^{27}$, $R^{28}$, $R^{29}$ and $R^{30}$ are each independently a lower alkyl group optionally having substituent(s), an aryl group optionally having substituent(s), an aralkyl group optionally having substituent(s) or a heteroaryl group optionally having substituent(s), or $R^{28}$ and $R^{29}$ may form, together with the adjacent nitrogen atom, an aliphatic nitrogen-containing heterocycle optionally having substituent(s) (hereinafter to be also referred to as compound (XXVI)), and compound (IV), and the optically active compound is a compound represented by the formula (XXVII):

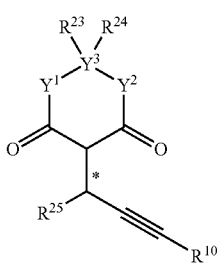

wherein $Y^1, Y^2, Y^3, R^{10}, R^{23}, R^{24}$ and $R^{25}$ are as defined above and * shows an asymmetric carbon (hereinafter to be also referred to as compound (XXVII)).

[19] The production method of the above-mentioned,[10], wherein the asymmetric reaction is an asymmetric hydroboration reaction.

[20] The production method of the above-mentioned [19], wherein the asymmetric transition metal complex is prepared by reacting the compound of the above-mentioned [4] with $Rh(cod)_2X^1$ wherein $X^1$ and cod are as defined above.

[21] The production method of the above-mentioned [19] or [20], wherein the substrate comprises a compound represented by the formula (VI): $R^{11}-HC=CH-R^2$ (VI) wherein $R^{11}$ is an aryl group optionally having substituent(s), a lower alkyl group optionally having substituent(s), a cycloalkyl group optionally having substituent(s), a aralkyl group optionally having substituent(s) or a heteroaryl group optionally having substituent(s), and $R^{12}$ is a hydrogen atom, a lower alkyl group optionally having substituent(s), a cycloalkyl group optionally having substituent(s), an aralkyl group optionally having substituent(s), an aryl group optionally having substituent(s) or a heteroaryl group optionally having substituent(s) (hereinafter to be also referred to as compound (VI)), and a boron compound represented by the formula (VII): $HBR^{13}R^{14}$ (VII) wherein $R^{13}$ and $R^{14}$ are each independently a hydrogen atom, a lower alkyl group, a lower alkoxy group, an aryl group, a heteroaryl group or an arylalkoxy group, or $R^{13}$ and $R^{14}$ may form a heterocycle or a fused ring thereof optionally having substituent(s) together with a boron atom bonded thereto (hereinafter to be also referred to as boron compound (VII)) or a complex thereof, and the optically active compound is a compound represented by the formula (VIII):

wherein $R^{11}$, $R^{12}$, $R^{13}$ and $R^{14}$ are as defined above and * shows an asymmetric carbon (hereinafter to be also referred to as compound (VIII)).

[22] A production method of a compound represented by the formula (IX):

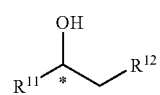

wherein $R^{11}$ and $R^{12}$ are as defined above and * shows an asymmetric carbon (hereinafter to be also referred to as compound (IX)), which comprises a step of reacting compound (VIII) produced in the above-mentioned [21], with an oxidizing agent.

[23] A production method of a compound represented by the formula (X):

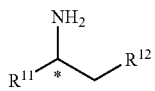
(X)

wherein $R^{11}$ and $R^{12}$ are as defined above and * shows an asymmetric carbon (hereinafter to be also referred to as compound (X)), which comprises a step of reacting compound (VIII) produced in the above-mentioned [21], with hydroxylamine-O-sulfonic acid.

[24] A production method of a compound represented by the formula (XII):

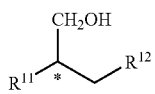
(XII)

wherein $R^{11}$ and $R^{12}$ are as defined above and * shows an asymmetric carbon (hereinafter to be also referred to as compound (XII)), which comprises a step of reacting compound (VIII) produced in the above-mentioned [21], with a compound represented by the formula (XI): $M^1CH_2X^2$ (XI) wherein $M^1$ is Li, Na, $MgX^5$ or $ZnX^5$ wherein $X^5$ is a halogen atom and $X^2$ is a halogen atom (hereinafter to be also referred to as compound (XI)).

[25] A production method of a compound represented by the formula (XIV):

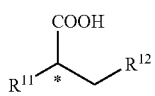
(XIV)

wherein $R^{11}$ and $R^{12}$ are as defined above and * shows an asymmetric carbon (hereinafter to be also referred to as compound (XIV)), which comprises a step of reacting compound (VIII) produced in the above-mentioned [21], with a compound represented by the formula (XIII): $M^2CH(X^3)_2$ (XIII) wherein $M^2$ is Li, Na, $MgX^6$ or $ZnX^6$ wherein $X^6$ is a halogen atom and $X^3$ is a halogen atom (hereinafter to be also referred to as compound (XIII)).

[26] The production method of the above-mentioned [10], wherein the asymmetric reaction is an asymmetric diboration reaction.

[27] The production method of the above-mentioned [26], wherein the asymmetric transition metal complex is prepared by reacting the compound of the above-mentioned [4] with (nbd)Rh(acac) wherein nbd and acac are as defined above.

[28] The production method of the above-mentioned [26] or [27], wherein the substrate comprises a compound represented by the formula (XV):

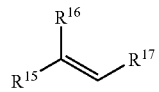
(XV)

wherein $R^{15}$ and $R^{16}$ are each independently a hydrogen atom, a lower alkyl group optionally having substituent(s), an aryl group optionally having substituent(s), a cycloalkyl group optionally having substituent(s), an aralkyl group optionally having substituent(s) or a heteroaryl group optionally having substituent(s) provided that $R^{15}$ and $R^{16}$ are not the same substituents, and $R^{17}$ is a hydrogen atom, a lower alkyl group optionally having substituent(s), an aryl group optionally having substituent(s), a cycloalkyl group optionally having substituent(s), an aralkyl group optionally having substituent(s) or a heteroaryl group optionally having substituent(s), or $R^{16}$ and $R^{17}$ may form a homocyclic ring or a fused ring thereof together with carbon atom bonded thereto (hereinafter to be also referred to as compound (XV)), and a boron compound represented by the formula (XVI): $R^{18}R^{19}B$—$BR^{18}R^{19}$ (XVI) wherein $R^{18}$ and $R^{19}$ are each independently a hydrogen atom, a lower alkyl group, a lower alkoxy group, an aryl group, a heteroaryl group or an aralkoxy group, or $R^{18}$ and $R^{19}$ may form a heterocycle or a fused ring thereof optionally having substituent(s) together with a boron atom bonded thereto (hereinafter to be also referred to as boron compound (XVI)) or a complex thereof, and the optically active compound is a compound represented by the formula (XVII):

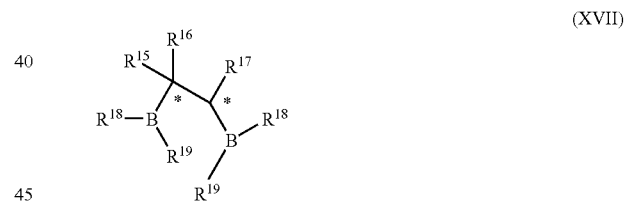
(XVII)

wherein $R^{15}$, $R^{16}$, $R^{17}$, $R^{18}$ and $R^{19}$ are as defined above and * shows an asymmetric carbon (hereinafter to be also referred to as compound (XVII)).

[29] A production method of a compound represented by the formula (XVIII):

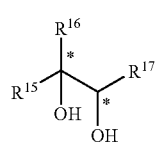
(XVIII)

wherein $R^{15}$, $R^{16}$ and $R^{17}$ are as defined above and * shows an asymmetric carbon (hereinafter to be also referred to as compound (XVIII)), which comprises a step of reacting compound (XVII) produced in the above-mentioned [28], with an oxidizing agent.

[30] A production method of compound (I), which comprises subjecting a compound represented by the formula (XIX):

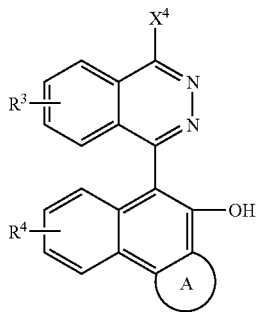

(XIX)

wherein ring A, $R^3$ and $R^4$ are as defined above and $X^4$ is a halogen atom, a p-toluenesulfonyloxy, a methanesulfonyloxy or a trifluoromethanesulfonyloxy (hereinafter to be also referred to as compound (XIX)) to the following steps (i) to (iii):

(i) a step of reaction with a compound represented by the formula (XX): $HOR^5$ (XX) or the formula (XXI): $H_2NR^6$ (XXI) wherein $R^5$ and $R^6$ are as defined above (hereinafter to be also referred to as compound (XX) and compound (XXI), respectively) to convert the residue represented by $X^4$ to a residue represented by X wherein X is as defined above;

(ii) a step of reaction with trifluoromethanesulfonic anhydride in the presence of a base to convert the hydroxyl group to —OTf wherein Tf is a trifluoromethanesulfonyl group; and (iii) a step of reacting a compound represented by the formula (XIX'):

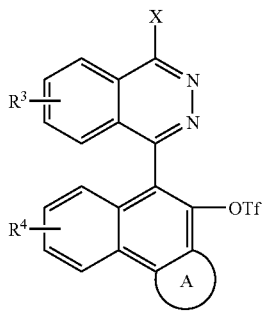

(XIX')

wherein each symbol is as defined above (hereinafter to be also referred to as compound (XIX')) produced in the aforementioned steps (i) and (ii), with a compound represented by the formula (XXII): $HPR^1R^2$ (XXII) wherein $R^1$ and $R^2$ are as defined above (hereinafter to be also referred to as compound (XXII)) in the presence of a transition metal complex containing phosphines to convert —OTf thereof to a residue represented by —$PR^1R^2$ wherein $R^1$ and $R^2$ are as defined above.

[31] The production method of the above-mentioned [30], wherein $R^5$ or $R^6$ is a residue having an asymmetric center.

[32] The production method of the above-mentioned [31], wherein comprises a step of separating compound (I) which is a diastereomer mixture.

An asymmetric transition metal complex containing compound (I) of the present invention as an asymmetric ligand has enabled asymmetric addition reaction, asymmetric conjugate addition reaction, asymmetric hydroboration reaction and the like at a high selective rate and in a high yield, to which application of a catalyst using a conventional asymmetric ligand such as BINAP etc. has been difficult.

In addition, since compound (I) can be prepared from a known compound in a relatively small number of steps of 3 steps without special operation, and even in its optical resolution, formation of a diastereomer complex with an optically active palladium compound such as QUINAP is not necessary, it can be conveniently and economically prepared.

Moreover, this production method is a highly useful method for designing a ligand suitable for various asymmetric reactions, since conversion of substituent and structure of compound (I) is easier as compared to QUINAP.

DETAILED DESCRIPTION OF THE INVENTION

The present invention is explained in detail in the following.

Each symbol used in the present specification is defined below.

The "halogen atom" for $R^3$, $R^4$, $X^2$, $X^3$, $X^4$, $X^5$ or $X^6$ is fluorine atom, a chlorine atom, a bromine atom or an iodine atom. $R^3$ and $R^4$ are each preferably a chlorine atom or a fluorine atom. $X^2$ and $X^3$ are each preferably a chlorine atom or a bromine atom. $X^4$ is preferably a chlorine atom or a bromine atom. $X^5$ and $X^6$ are each preferably a chlorine atom or a bromine atom.

The "halogen atom" as a counter ion for $X^1$ is a fluorine ion, a chlorine ion, a bromine ion or an iodine ion, preferably a chlorine ion or a bromine ion.

As the "lower alkoxy group" for $R^3$, $R^4$, $R^{13}$, $R^{14}$, $R^{18}$ or $R^{19}$, a straight chain or branched alkoxy group having 1 to 12 carbon atoms, such as methoxy, ethoxy, propoxy, isopropoxy, butoxy, isobutoxy, sec-butoxy, tert-butoxy, pentoxy, isopentoxy, neopentoxy, hexyloxy, heptyloxy, octyloxy, nonyloxy, decyloxy, undecyloxy, dodecyloxy and the like can be mentioned, with preference given to methoxy, ethoxy, isopropoxy and tert-butoxy.

As the "lower alkyl group" for $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{23}$, $R^{24}$, $R^{25}$, $R^{26}$, $R^{27}$, $R^{28}$, $R^{29}$ or $R^{30}$, a straight chain or branched alkyl group having 1 to 12 carbon atoms, such as methyl, ethyl, propyl, isopropyl, butyl, isobutyl, sec-butyl, tert-butyl, pentyl, isopentyl, neopentyl, hexyl, 2-ethylbutyl, heptyl, octyl, nonyl, decyl, undecyl, dodecyl and the like can be mentioned, with preference given to methyl, ethyl, propyl, butyl, sec-butyl and tert-butyl.

The "lower alkyl group" for $R^5$, $R^6$, $R^7$, $R^8$, $R^9$, $R^{10}$, $R^{11}$, $R^{12}$, $R^{15}$, $R^{16}$, $R^{17}$, $R^{23}$, $R^{24}$, $R^{25}$, $R^{26}$, $R^{27}$, $R^{28}$, $R^{29}$ or $R^{30}$ may have a substituent(s) at substitutable position(s), and as the substituent(s), the above-defined halogen atom, the above-defined lower alkoxy group, hydroxyl group, oxo, amino group, nitro group, cyano group, carboxyl group, alkoxycarbonyl group wherein the alkyl moiety is the above-defined "lower alkyl group", and the like can be mentioned. The number of the substituent is not particularly limited and 1 to 3 is preferable and they may be the same or different.

The "heteroalkyl group" for $R^{25}$ is the above-mentioned lower alkyl group, wherein 1 to 3 carbon atoms are substituted by at least one kind of hetero atom selected from oxygen atom, nitrogen atom and sulfur atom and, for example, methoxymethyl, 1-, or 2-methoxyethyl, 1-, or 2-ethoxyethyl, methoxyethoxyethyl, methylaminomethyl, dimethylaminomethyl, methylthiomethyl and the like can be mentioned.

The "heteroalkyl group" may have substituent(s) at substitutable position(s), and as the substituent(s), the same substituents as exemplified for the above-mentioned "lower alkyl group optionally having substituent(s)" can be mentioned. The number of the substituent is not particularly limited and 1 to 3 is preferable and they may be the same or different.

As the "lower alkenyl group" of "lower alkenyl group optionally having substituent(s)" for $R^7$, $R^8$ or $R^9$, a straight chain or branched alkenyl group having 2 to 10 carbon atoms, such as ethenyl, 1-propenyl, allyl, 1-methyl-2-propenyl, 1-butenyl, 2-butenyl, 3-butenyl, 1-pentenyl, 2-pentenyl, 1-hexenyl, 2-hexenyl, 1-heptenyl, 2-heptenyl, 1-octenyl, 2-octenyl, 1-nonenyl, 2-nonenyl, 1-decenyl, 2-decenyl and the like can be mentioned, with preference given to allyl. The alkenyl group may have a substituent at a substitutable position, and as the substituent, the above-defined halogen atom, the above-defined lower alkoxy group, hydroxyl group, oxo, amino group, nitro group, cyano group, carboxyl group, alkoxycarbonyl group wherein the alkyl moiety is the above-defined "lower alkyl group", the below-defined aryl group and the like can be mentioned. The number of the substituent is not particularly limited and 1 to 3 is preferable and they may be the same or different.

As the "lower alkynyl group" of the "lower alkynyl group optionally having substituent(s)" for $R^7$, a straight chain or branched alkynyl group having 2 to 10 carbon atoms, such as ethynyl, 1-propynyl, 2-propynyl, 1-methyl-2-propynyl, 1-butynyl, 2-butynyl, 3-butynyl, 1-pentynyl, 2-pentynyl, 1-hexynyl, 2-hexynyl, 1-heptynyl, 2-heptynyl, 1-octynyl, 2-octynyl, 1-nonynyl, 2-nonynyl, 1-decynyl, 2-decynyl and the like can be mentioned. The alkynyl group may have substituent(s) at substitutable position(s), and as the substituent(s), those similar to the substituents exemplified for the above-mentioned "alkenyl group optionally having substituent(s)" can be mentioned. The number of the substituent is not particularly limited and 1 to 3 is preferable and they may be the same or different.

As the "aryl group" octynyl, for $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{23}$, $R^{24}$, $R^{25}$, $R^{26}$, $R^{27}$, $R^{28}$, $R^{29}$ or $R^{30}$, an aryl group having 6 to 20 carbon atoms, such as phenyl, 1-, or 2-naphthyl, biphenyl and the like can be mentioned.

The aryl group for $R^3$, $R^4$, $R^5$, $R^6$, $R^7$, $R^8$, $R^9$, $R^{10}$, $R^{11}$, $R^{12}$, $R^{15}$, $R^{16}$, $R^{17}$, $R^{23}$, $R^{24}$, $R^{25}$, $R^{26}$, $R^{27}$, $R^{28}$, $R^{29}$ or $R^{30}$ may have substituent(s) at substitutable position(s), and as the substituent(s), the above-defined halogen atom, the above-defined lower alkyl group, the above-defined lower alkoxy group, hydroxyl group, amino group, nitro group, cyano group, carboxyl group, alkoxycarbonyl group wherein the alkyl moiety is the above-defined "lower alkyl group", the above-defined aryl group, the below-defined aralkyl group and the like can be mentioned. The number of the substituent is not particularly limited and 1 to 3 is preferable and they may be the same or different.

As the substituent of the "phenyl group optionally having substituent(s)" for $R^1$ or $R^2$, those similar to the substituents that the above-mentioned aryl group may have can be mentioned. The number of the substituent is not particularly limited and 1 to 3 is preferable and they may be the same or different.

Specific examples of the "phenyl group optionally having substituent(s)" include p-tolyl group, m-tolyl group, o-tolyl group and xylyl group (2,3-xylyl group, 2,4-xylyl group, 2,5-xylyl group, 2,6-xylyl group, 3,4-xylyl group and 3,5-xylyl group).

As the "heteroaryl group" for $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{23}$, $R^{24}$, $R^{25}$, $R^{26}$, $R^{27}$, $R^{28}$, $R^{29}$ or $R^{30}$, for example, a 5-to 10-membered aromatic heterocyclic group containing, besides carbon atom, 1 to 3 hetero atoms selected from an oxygen atom, a sulfur atom and a nitrogen atom, a fused heterocyclic group thereof and the like can be mentioned. For example, 2-, or 3-thienyl, 2-, or 3-furyl, 1-, 2-, or 3-pyrrolyl, 1-, 2-, 4-, or 5-imidazolyl, 2-, 4-, or 5-oxazolyl, 2-, 4-, or 5-thiazolyl, 1-, 3-, 4-, or 5-pyrazolyl, 3-, 4-, or 5-isoxazolyl, 3-, 4-, or 5-isothiazolyl, 1,2,4-triazol-1-, 3-, 4-, or 5-yl, 1,2,3-triazol-1-, 2-, or 4-yl, 1H-tetrazol-1-, or 5-yl, 2H-tetrazol-2-, or 5-yl, 2-, 3-, or 4-pyridyl, 2-, 4-, or 5-pyrimidinyl, 1-, 2-, 3-, 4-, 5-, 6-, or 7-indolyl, 2-, 3-, 4-, 5-, 6-, or 7-benzofuryl, 2-, 3-, 4-, 5-, 6-, or 7-benzothienyl, 1-, 2-, 4-, 5-, 6-, or 7-benzimidazolyl, 2-, 3-, 4-, 5-, 6-, 7-, or 8-quinolyl, 1-, 3-, 4-, 5-, 6-, 7-, or 8-isoquinolyl and the like can be mentioned.

The heteroaryl group for $R^5$, $R^6$, $R^7$, $R^8$, $R^9$, $R^{10}$, $R^{11}$, $R^{12}$, $R^{15}$, $R^{16}$, $R^{17}$, $R^{23}$, $R^{24}$, $R^{25}$, $R^{26}$, $R^{27}$, $R^{28}$, $R^{29}$ or $R^{30}$ may have substituent(s) at substitutable position(s), and as the substituent(s), those similar to the substituents exemplified for the above-mentioned "aryl group optionally having substituent(s)" can be mentioned. The number of the substituent is not particularly limited and 1 to 3 is preferable and they may be the same or different.

As the "cycloalkyl group" of the "cycloalkyl group optionally having substituent(s)" for $R^3$, $R^4$, $R^7$, $R^8$, $R^9$, $R^{10}$, $R^{11}$, $R^{12}$, $R^{15}$, $R^{16}$, $R^{17}$ or $R^{25}$, a cycloalkyl group having 3 to 7 carbon atoms, such as cyclopropyl, cyclobutyl, cyclopentyl, cyclohexyl and cycloheptyl can be mentioned. The cycloalkyl group may have substituent(s) at substitutable position(s), and as the substituent(s), those similar to the substituents exemplified for the above-mentioned "aryl group optionally having substituent(s)" or oxo can be mentioned. The number of the substituent is not particularly limited and 1 to 3 is preferable and they may be the same or different.

As the "aralkyl group" of the "aralkyl group optionally having substituent(s)" for $R^3$, $R^4$, $R^5$, $R^6$, $R^7$, $R^8$, $R^9$, $R^{10}$, $R^{11}$, $R^{12}$, $R^{15}$, $R^{16}$, $R^{17}$, $R^{23}$, $R^{24}$, $R^{25}$, $R^{26}$, $R^{27}$, $R^{28}$, $R^{29}$ or $R^{30}$, aralkyl group formed by the substitution of the above-defined "aryl group" at any position of the above-defined "lower alkyl group", for example, benzyl, 1-, or 2-phenylethyl, 1-, 2-, or 3-phenylpropyl, 1-, or 2-naphthylmethyl, 1-, or 2-(1-naphthyl)ethyl, 1-, or 2-(2-naphthyl)ethyl, 2-ethyl-1-phenylbutyl, benzhydryl, trityl and the like can be mentioned. The aralkyl group may have substituent(s) at substitutable position(s), and as the substituent(s), those similar to the substituents exemplified for the above-mentioned "aryl group optionally having substituent(s)" or oxo can be mentioned. The number of the substituent is not particularly limited and 1 to 3 is preferable and they may be the same or different.

As the "aralkyl group optionally having substituent(s)", 2-phenylethyl, 2-(4-tolyl)ethyl, 2-ethyl-2-hydroxy-1-phenylbutyl, 2-(1-naphthyl)ethyl, 2-(2-naphthyl)ethyl and the like can be mentioned.

As the "heteroarylalkyl group" of the "heteroarylalkyl group optionally having substituent(s)" for $R^{25}$, a heteroarylalkyl group formed by substitution of the above-defined "heteroaryl group" at any position of the above-defined "lower alkyl group", such as 2-, or 3-thienylmethyl, 2-, or 3-furylmethyl, 1-, 2-, or 3-pyrrolylmethyl, 1-, 2-, 4-, or 5-imidazolylmethyl, 2-, 4-, or 5-oxazolylmethyl, 2-, 4-, or 5-thiazolylmethyl, 1-, 3-, 4-, or 5-pyrazolylmethyl, 3-, 4-, or 5-isooxazolylmethyl, 3-, 4-, or 5-isothiazolylmethyl, 1,2,4-triazol-1,3-, 4-, or 5-ylmethyl, 1,2,3-triazol-1,2-, or 4-ylmethyl, 1H-tetrazol-1-, or 5-ylmethyl, 2H-tetrazol-2-, or 5-ylmethyl, 2-, 3-, or 4-pyridylmethyl, 2-, 4-, or 5-pyrimidinylmethyl, 1-, 2-, 3-, 4-, 5-, 6-, or 7-indolylmethyl, 2-, 3-, 4-, 5-, 6-, or 7-benzofurylmethyl, 2-, 3-, 4-, 5-, 6-, or 7-benzothienylmethyl, 1-, 2-, 4-, 5-, 6-, or 7-benzimidazolylmethyl, 2-, 3-, 4-, 5-, 6-, 7-, or 8-quinolylmethyl, 1-, 3-, 4-, 5-, 6-, 7-, or 8-isoquinolylmethyl, 1-, or 2-(2-, or 3-thienyl)ethyl, 1-, or 2-(2-, or 3-furyl)ethyl, 1-, or 2-(1-, 2-, or 3-pyrrolyl) ethyl, 1-, or 2-(1-, 2-, 4-, or 5-imidazolyl)ethyl, 1-, or 2-(2-, 4-, or 5-oxazolyl)ethyl, 1-, or 2-(2-, 4-, or 5-thiazolyl)ethyl, 1-, or 2-(1-, 3-, 4-, or 5-pyrazolyl)ethyl, 1-, or 2-(3-, 4-, or 5-isooxazolyl)ethyl, 1-, or 2-(3-, 4-, or 5-isothiazolyl)ethyl, 1-, or 2-(1,2,4-triazol-1,3-, 4-, or 5-yl)ethyl, 1-, or 2-(1,2,3-triazol-1-, 2-, or 4-yl)ethyl, 1-, or 2-(1H-tetrazol-1-, or 5-yl)ethyl, 1-, or 2-(2H-tetrazol-2-, or 5-yl)ethyl, 1-, or 2-(2-, 3-, or 4-pyridyl)ethyl, 1-, or 2-(2-, 4-, or 5-pyrimidinyl)ethyl, 1-, or 2-(1-, 2-, 3-, 4-, 5-, 6-, or 7-indolyl)ethyl, 1-, or 2-(2-, 3-, 4-, 5-, 6-, or 7-benzofuryl)ethyl, 1-, or 2-(2-, 3-, 4-, 5-, 6-, or 7-benzothienyl)ethyl, 1-, or 2-(1-, 2-, 4-, 5-, 6-, or 7-benzimidazolyl)ethyl, 1-, or 2-(2-, 3-, 4-, 5-, 6-, 7-, or 8-quinolyl) ethyl, 1-, or 2-(1-, 3-, 4-, 5-, 6-, 7-, or 8-isoquinolyl)ethyl and the like can be mentioned. The heteroarylalkyl group may have substituent(s) at substitutable position(s), and as the substituent(s), those similar to the substituents exemplified for the above-mentioned "aryl group optionally having substituent(s)" or oxo can be mentioned. The number of the substituent is not particularly limited and 1 to 3 is preferable and they may be the same or different.

As the substituent that may be possessed when ring A is a benzene ring, halogen atom, lower alkyl group, lower alkoxy group, cycloalkyl group optionally having substituent(s), aralkyl group optionally having substituent(s), aryl group optionally having substituent(s) and the like for $R^3$ or $R^4$ can be mentioned.

As the aliphatic nitrogen-containing heterocycle optionally formed by $R^8$ and $R^9$ or $R^{28}$ and $R^{29}$ together with the nitrogen atom bonded thereto, an aliphatic heterocycle optionally having, besides the nitrogen atom to which $R^8$ and $R^9$ or $R^{28}$ and $R^{29}$ are bonded, 1 to 4 hetero atoms selected from nitrogen atom, oxygen atom and sulfur atom, for example, pyrrolidine, piperidine, morpholine, thiomorpholine, piperazine and the like can be mentioned. The aliphatic nitrogen-containing heterocycle may have substituent(s) at substitutable position(s), and as the substituent(s), those similar to the substituents exemplified for the above-mentioned "aryl group optionally having substituent(s)" or oxo can be mentioned. The number of the substituent is not particularly limited and 1 to 3 is preferable and they may be the same or different.

As the "aliphatic nitrogen-containing heterocycle optionally having substituent(s)" for $R^8$ and $R^9$, 4-piperidinone is preferable.

As the "arylalkoxy group" for $R^{13}$, $R^{14}$, $R^{18}$ or $R^{19}$, the above-defined arylalkoxy group having a "lower aralkyl group", such as benzyloxy, 1-, or 2-phenylethoxy, 1-, 2-, or 3-phenylpropoxy, 1-, or 2-naphthylmethoxy, benzhydryloxy, trityloxy and the like can be mentioned.

As the "trialkylsilyl group" for $R^{10}$, trimethylsilyl group, tert-butyldimethylsilyl group, triethylsilyl group, triisopropylsilyl group and the like can be mentioned, with preference given to trimethylsilyl group and triethylsilyl group.

As the heterocycle optionally having substituent(s), which may be formed together with the boron atom to which $R^{13}$ and $R^{14}$ or $R^{18}$ and $R^{19}$ are bonded, or a fused ring thereof, heterocycle optionally having, besides boron atom, 1 to 3 oxygen atom, nitrogen atom or sulfur atom or a fused ring thereof, such as 1,3,2-dioxaborolane, 1,3,2-benzodioxaborole, 9-borabicyclo[3.3.1]nonane and the like can be mentioned, with preference given to 1,3,2-benzodioxaborole. The heterocycle or a fused ring thereof may have substituent(s) at substitutable position(s), and as the substituent(s), those similar to the substituents exemplified for the above-mentioned "aryl group optionally having substituent(s)" can be mentioned. The number of the substituent is not particularly limited and 1 to 3 is preferable and they may be the same or different.

In compound (XV), as the homocyclic ring optionally having substituent(s), which may be formed together with the carbon atom to which $R^{16}$ and $R^{17}$ are bonded, or a fused ring thereof, cyclopentene, cyclohexene, indene, 1,2-dihydronaphthalene and the like can be mentioned.

As the complex of boron compound (VII) or (XVI), for example, a coordinated complex such as tetrahydrofuran, dimethyl sulfide, ammonia, tert-butylamine, N,N-dimethylaniline, N,N-diisopropylethylamine, dimethylamine, isopropylamine, triethylamine, trimethylamine, morpholine, pyridine and the like can be mentioned.

In compounds (V), (Va), (Vb), (VIII), (IX), (X), (XII), (XIV), (XVII), (XVIII) and (XXVII), * means that the marked carbon atom is an asymmetric carbon, and that each compound is an optically active compound.

In the present specification, by optically active is meant that the asymmetric carbon is not a mixture of an equivalent (e.g., racemate) amount of isomers having different configurations. When one of the stereoisomers is present in excess (e.g., 6:4 mixture), the compound is defined to be optically active.

The compounds (I), (XIX) and (XIX') show atropisomerism based on the hindered rotation of a single bond linking a phthalazine ring and a naphthalene ring, and show asymmetry that can be resolved at room temperature.

The compounds defined in the present specification may be in the form of a salt. As the salt, for example, inorganic acid salt (e.g., hydrochloride, sulfate, nitrate, phosphate etc.); organic acid salt (e.g., acetate, propionate, methanesulfonate, 4-toluenesulfonate, oxalate, maleate etc.); alkali metal salt (e.g., sodium salt, potassium salt etc.); alkaline earth metal salt (e.g., calcium salt, magnesium salt etc.); organic base salt (e.g., trimethylamine salt, triethylamine salt, pyridine salt, picoline salt, dicyclohexylamine salt etc.) and the like can be mentioned.

As $R^1$ and $R^2$ in compound (I), phenyl group optionally having substituent(s) or cyclohexyl group is preferable, phenyl group, tolyl group (p-tolyl group or m-tolyl group) or cyclohexyl is more preferable. As $R^3$ and $R^4$, a hydrogen atom, lower alkyl group, lower alkoxy group or cycloalkyl group is preferable, a hydrogen atom or methoxy group is more preferable.

As $R^5$ and $R^6$ for X in compound (I), aralkyl group optionally having substituent(s) is preferable, and a residue having an asymmetric center is more preferable. To be specific, (R)—, or (S)-2-phenylethyl group, (R)—, or (S)-2-(4-tolyl) ethyl, (R)—, or (S)-2-ethyl-2-hydroxy-1-phenylbutyl, (R)—, or (S)-2-(1-naphthyl)ethyl, (R)—, or (S)-2-(2-naphthyl)ethyl and the like are preferable.

The compound (I) of the present invention can be produced by Production Method 1 as shown in the following reaction scheme.

Production Method 1

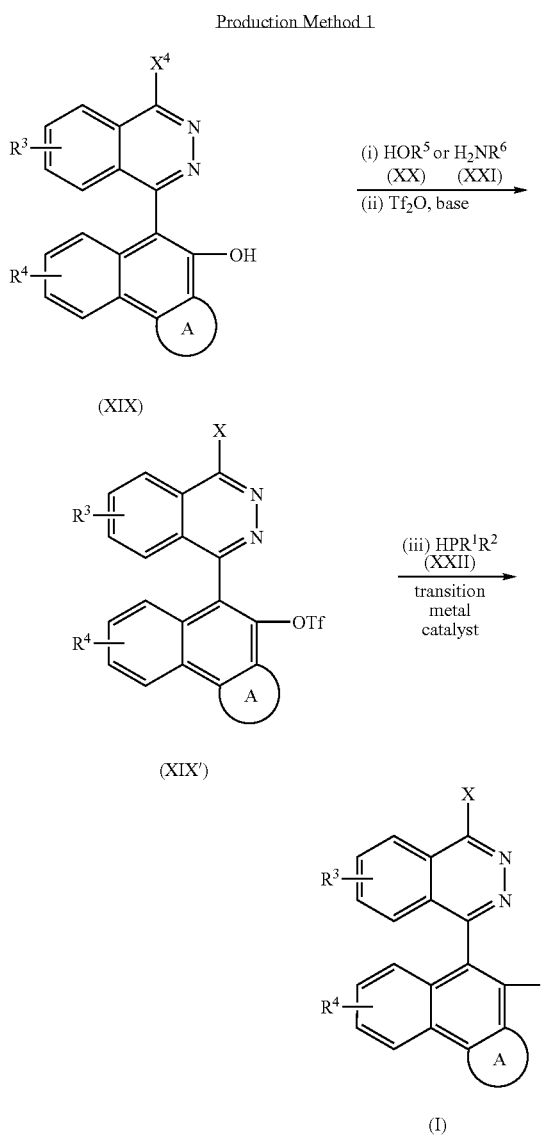

wherein each symbol is as defined above.

That is, compound (I) can be produced by subjecting compound (XIX) as starting material to steps comprising (i) a step of the reaction with compound (XX) or compound (XXI) to convert the residue represented by $X^4$ to the residue represented by X;

(ii) a step of the reaction with trifluoromethanesulfonic anhydride in the presence of a base to convert the hydroxyl group to —OTf; and (iii) a step of the reaction of compound (XIX') obtained in the aforementioned steps (i) and (ii) with compound (XXII) in the presence of transition metal complex containing phosphines to convert —OTf thereof to the residue represented by —$PR^1R^2$ wherein $R^1$ and $R^2$ are as defined above.

By employing such Production Method 1, compound (I) can be produced easily from a known compound (XIX) in short steps of 3 steps without special operation.

When $R^5$ or $R^6$ for X is a preferable mode of a residue having an asymmetric center, optical resolution is possible even without forming a diastereomer complex with an optically active palladium compound as in the case of QUINAP, since compound (I) itself becomes a diastereomer mixture.

Moreover, by this Production Method 1, substituents X, $R^3$ and $R^4$ and the like for compound (I) and skeleton itself can be converted easily, and various ligands having different electric or steric effects can be easily prepared. Therefore, Production Method 1 is highly useful for designing ligands suitable for various asymmetric reactions.

Production Method 1 is explained in the following. Each compound produced in steps (i) to (iii) can be isolated and purified by applying generally treatments by, for example, subjecting to silica gel column chromatography and the like after extraction.

In Production Method 1, the order of Step (i) and Step (ii) is not particularly limited and either one may be performed first. However, in the case of reaction with compound (XXI) in Step (i), Step (ii) is preferably performed first, because the proton of the converted group represented by —$NHR^6$ may be trifluoromethanesulfonylated in Step (ii) when Step (i) is performed first.

In Step (i), since reaction with compound (XX) (hereinafter to be also referred to as Step (i-1)) and reaction with compound (XXI) (hereinafter to be also referred to as Step (i-2)) require different reaction conditions, they are explained separately in the following.

Step (i-1) can be carried out by reacting the starting compound (compound (XIX) or triflate thereof) with compound (XX) in a solvent in the presence of a base. While the order of the addition of the reagents is not particularly limited, compound (XX) is preferably reacted in advance with a base in a solvent to sufficiently convert to an alcoholate of compound (XX) and then a starting compound is added.

As the base to be used in Step (i-1), for example, sodium hydride, sodium amide, sodium hydroxide, potassium hydroxide and the like can be mentioned with preference given to sodium hydride. The amount of the base to be used is preferably 1 to 5 equivalents, more preferably 1.1 to 2.5 equivalents, relative to compound (XX). While the reaction can be carried out even when the amount of the base to be used is outside this range, when the amount is less than this range, the alcoholate of compound (XX) may not be sufficiently produced, and when the amount is higher, a by-product may be generated.

The amount of compound (XX) to be used is preferably 1 to 5 equivalents, more preferably 1 to 1.5 equivalents, relative to the starting compound.

The solvent to be used in Step (i-1) may be any as long as it does not inhibit the reaction, for example, a single member of tetrahydrofuran (THF), toluene, xylene, chlorobenzene, dichlorobenzene, N,N-dimethylformamide, 1,2-dimethoxyethane, methyl tert-butyl ether, 1,4-dioxane or dimethylsulfoxide, or a mixed solvent thereof can be mentioned. The amount of the solvent to be used is 0.2 to 50 L per 1 kg of the starting compound.

The reaction temperature of Step (i-1) generally –20° C. to 100° C., with preference to give 0° C. to 40° C. While the reaction time varies depending on the reagent and reaction temperature to be employed, it is generally 4 hrs to 40 hrs.

Step (i-2) can be carried out by reacting the starting compound (compound (XIX) or triflate thereof) with compound (XXI) in a solvent or without solvent. The order of the addition of the reagents is not particularly limited. Since compound (XXI) has high nucleophilicity, the reaction proceeds without a base.

The amount of compound (XXI) to be used is preferably 1 to 20 equivalents, more preferably 1 to 7 equivalents, relative to the starting compound. While the reaction can be carried out even when the amount of compound (XXI) to be used is outside this range, when the amount is less than this range, the reaction may not be completed and when the amount is higher, the cost becomes disadvantageously high.

While Step (i-2) can be carried out in a solvent, when compound (XXI) is used in a relatively large amount, this step is preferably carried out without a solvent. When a solvent is used, it may be any as long as it does not inhibit the reaction and, for example, a single member of toluene, xylene, chlorobenzene, dichlorobenzene, N,N-dimethylformamide, 1,2-dimethoxyethane, methyl tert-butyl ether, 1,4-dioxane and the like or a mixed solvent thereof can be used. The amount of the solvent to be used is preferably 0.1 L to 50 L per 1 kg of the starting compound.

The reaction temperature of Step (i-2) is generally 0° C. to 180° C., with preference given to 20° C. to 150° C. While the reaction time varies depending on the reagent and reaction temperature to be employed, it is generally 0.5 hr to 40 hrs.

Step (ii) can be carried out by reacting the starting compound (compound (XIX) or the compound wherein $X^4$ is convert to X) with trifluoromethanesulfonic anhydride in a solvent in the presence of a base. The order of the addition of the reagents is not particularly limited, and respective reagents may be added sequentially or simultaneously.

As the base to be used in Step (ii), for example, pyridine, triethylamine, diisopropylethylamine, 4-dimethylaminopyridine and the like can be mentioned, with preference given to pyridine and triethylamine. The amount of the base to be used is preferably 1 to 10 equivalents, relative to the starting compound. While the reaction can be carried out even when the amount of the base to be used is outside this range, when the amount is less than this range, the reaction may not be completed and when the amount is higher, the cost becomes disadvantageously high.

The amount of trifluoromethanesulfonic anhydride to be used is preferably 1 to 5 equivalents, more preferably 1 to 1.2 equivalents, relative to the starting compound. While the reaction can be carried out even when the amount of trifluoromethanesulfonic anhydride to be used is outside this range, when the amount is less than this range, the reaction may not be completed, and when the amount is higher, a side reaction may occur and a by-product may be generated.

The solvent to be used in Step (ii) may be any as long as it does not inhibit the reaction, for example, a single member of dichloromethane, toluene, xylene, chlorobenzene, dichlorobenzene, N,N-dimethylformamide, 1,2-dimethoxyethane, methyl tert-butyl ether, 1,4-dioxane, ethyl acetate, acetonitrile, chloroform or 1,2-dichloroethane or a mixed solvent thereof can be mentioned. The amount of the solvent to be used is within the range of 0.2 to 50-fold weight, relative to the starting compound.

The reaction temperature of Step (ii) is generally −78° C. to 100° C., with preference given to −20° C. to 40° C. While the reaction time varies depending on the reagent and reaction temperature to be employed, it is generally 0.5 hr to 40 hrs.

In Step (iii), compound (I) can be produced by, for example, reacting compound (XIX') with compound (XXII) in a solvent in the presence of a transition metal complex containing phosphines. The order of the addition of the reagents is not particularly limited, and respective reagents may be added sequentially or simultaneously.

As the transition metal complex containing phosphines to be used in Step (iii), for example, $NiCl_2(dppe)$, $NiCl_2(dppp)$, $NiCl_2(dppb)$, $PdCl_2(dppe)$, $PdCl_2(dppp)$, $PdCl_2(dppb)$ (wherein dppe is 1,2-bis(diphenylphosphino)ethane, dppp is 1,3-bis(diphenylphosphino)propane and dppb is 1,4-bis(diphenylphosphino)butane) and the like can be mentioned, with preference given to $NiCl_2(dppe)$. The amount of transition metal complex containing phosphines to be used is preferably 0.01 to 1 equivalent, more preferably 0.02 to 0.2 equivalent, relative to compound (XIX'). While the reaction can be carried out even when the amount of the transition metal complex containing phosphines to be used is outside this range, when the amount is less than this range, the reaction tends to be slow, and when the amount is higher, the cost becomes disadvantageously high.

The amount of compound (XXII) to be used is preferably 1 to 10 equivalents, more preferably 1 to 3 equivalents, relative to compound (XIX'). While the reaction can be carried out even when the amount of compound (XXII) to be used is outside this range, when the amount is less than this range, the reaction may not be completed and when the amount is higher, the cost becomes disadvantageously high.

Step (iii) is preferably performed with the addition of a base for the purpose of trapping the acidity of the by-produced trifluoromethanesulfonic acid. As the base, for example, tertiary amine such as 1,4-diazabicyclo[2.2.2]octane (DABCO), diisopropylethylamine, triethylamine and the like can be mentioned. The amount of the base to be used is preferably 1 to 30 equivalents, more preferably 3 to 10 equivalents, relative to compound (XIX'). While the reaction can be carried out even when the amount of the base to be used is outside this range, when the amount is less than this range, the starting material or product may be decomposed to give a by-product, and when the amount is higher, the cost becomes disadvantageously high.

The solvent to be used in Step (iii) may be any as long as it does not inhibit the reaction, for example, a single member of N,N-dimethylformamide, toluene, xylene, chlorobenzene, dichlorobenzene, 1,2-dimethoxyethane, methyl tert-butyl ether, 1,4-dioxane, ethyl acetate, acetonitrile or 1,2-dichloroethane or a mixed solvent thereof can be mentioned. The amount of the solvent to be used is within the range of 0.2 to 50-fold weight, relative to compound (XIX').

The reaction temperature of Step (iii) is generally 0° C. to 180° C., with preference given to 40° C. to 140° C. While the reaction time varies depending on the reagent and reaction temperature to be employed, it is generally 2 hrs to 40 hrs.

When $R^5$ or $R^6$ for X is a residue having an asymmetric center, compound (I) obtained in Production Method 1 is a diastereomer mixture, and optically active compound (I) can be obtained by separation and purification. The separation and purification can be performed by conventional fractional recrystallization, silica gel chromatography and the like.

The compound (XIX), which is a starting material in Production Method 1, is a known compound, and can be prepared according to the method described in J. Org. Chem., 2003, 68, p. 6806-2609.

When compound (I) of the present invention is an optically active compound (hereinafter to be also referred to as optically active compound (I)), the asymmetric transition metal complex containing the optically active compound (I) as a ligand can be used as a catalyst for asymmetric reaction, namely, as an asymmetric catalyst.

As the transition metal of the transition metal complex, Ru, Pd, Rh, Cu, Ag and the like can be mentioned, with preference given to Rh, Cu and Ag.

The asymmetric transition metal complex can be prepared by, for example, reacting the optically active compound (I) with the transition metal salt or a complex thereof in a solvent.

As the transition metal salt or a complex thereof to be used for preparation of the asymmetric transition metal complex, for example, $CuX^1$, $Cu(X^1)_2$, $Rh(cod)_2X^1$, $(nbd)Rh(acac)$, $CyRu(X^1)_2$ or $AgX^1$ (wherein symbol or abbreviations is as defined above) and the like be mentioned, with preference given to CuX¹, Cu(X¹)₂, Rh(cod)₂X¹, (nbd)Rh(acac) and AgX¹.

While the amount of the transition metal salt or a complex thereof to be used varies depending on the kind thereof, it is preferably 0.5 to 2 equivalents, more preferably 1 to 1.3 equivalents, relative to optically active compound (I).

To change the oxidation number of the transition metal, a reductant can be added where necessary. As the reductant, ascorbic acid or a salt thereof (e.g., ascorbic acid, sodium ascorbate, potassium ascorbate etc.), phosphines (e.g., triphenylphosphine, tri(n-butyl)phosphine etc.) and the like can be mentioned.

The amount of the reductant to be used can be appropriately determined depending on the oxidation number to be changed. For example, when the oxidation number is changed by one valent, 1 equivalent to 40 equivalents, relative to the transition metal salt or a complex thereof can be added.

The solvent to be used for preparation of the asymmetric transition metal complex, may be as long as it does not inhibit the reaction, for example, a single member of tetrahydrofuran, toluene, dichloromethane, toluene, xylene, chlorobenzene, dichlorobenzene, N,N-dimethylformamide, dimethylsulfoxide, 1,2-dimethoxyethane, methyl tert-butyl ether, 1,4-dioxane, ethyl acetate, acetonitrile, chloroform, 1,2-dichloroethane, water, alcohol solvents such as methanol, ethanol, n-propanol, isopropanol, butanol and the like, and the like or a mixed solvent thereof can be mentioned. The amount of the solvent to be used is within the range of 0.2 to 50-fold weight, relative to optically active compound (I).

The reaction temperature for the preparation of the asymmetric transition metal complex is generally −20° C. to 130° C., with preference given to 0° C. to 40° C. While the reaction time varies depending on the reagent and reaction temperature to be employed, it is generally 0.5 hr to 40 hrs.

While the obtained asymmetric transition metal complex may be isolated and purified by a conventional method, a reaction mixture can be used as it is as an asymmetric catalyst.

As the asymmetric reaction catalyzed by the asymmetric transition metal complex of the present invention is not particularly limited and, for example, asymmetric hydrogenation reaction, asymmetric addition reaction, asymmetric conjugate addition reaction, asymmetric hydroboration reaction, asymmetric diboration reaction, asymmetric cyclization reaction, asymmetric aldol reaction, asymmetric substitution reaction or asymmetric Diels-Alder [4+2] cyclization reaction and the like can be mentioned, with preference given to asymmetric addition reaction, asymmetric conjugate addition reaction, asymmetric hydroboration reaction, asymmetric diboration reaction or asymmetric [2+3] cyclization reaction, asymmetric Sn2' substitution reaction and the like, for which conventional asymmetric catalysts cannot be easily applied.

In the asymmetric reaction, an optically active compound can be obtained by, for example, contacting a substrate to asymmetric transition metal complex in a solvent.

As used herein, the substrate means a compound which can be a starting material of the asymmetric reaction, with preference given to achiral or prochiral compound. It also encompasses an optically active compound or a racemate and the like, which have an asymmetric center. In addition, the substrate may be a single compound or a combination of two or more compounds.

One embodiment of the asymmetric addition reaction is shown as Production Method 2 in the following reaction scheme. In Production Method 2, compound (V) can be produced by, for example, reacting compound (II), compound (III) and compound (IV) as substrates with the asymmetric transition metal complex of the present invention as an asymmetric catalyst in a solvent. In this case, the asymmetric transition metal complex is preferably one prepared by the reaction of optically active compound (I) and CuX¹ (wherein X¹ is as defined above).

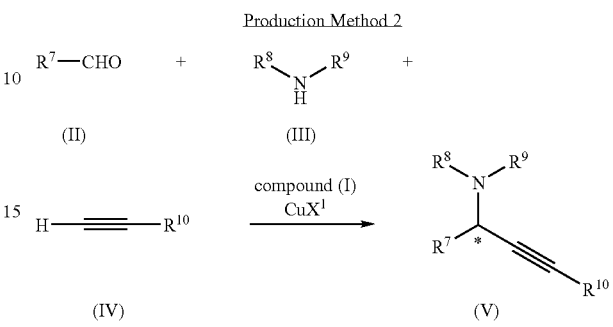

Production Method 2 wherein each symbol is as defined above.

In Production Method 2, while the order of the addition of the reagents is not particularly limited, preferably to the solution containing the prepared asymmetric transition metal complex are added compounds (II) to (IV) sequentially or simultaneously.

The amount of the asymmetric transition metal complex to be used is preferably 0.001 to 2 equivalents, more preferably 0.01 to 0.2 equivalent, relative compound (II). While the reaction can be carried out even when the amount of the asymmetric transition metal complex to be used is outside this range, when the amount is less than this range, the reaction may not be completed and when the amount is higher, the cost becomes disadvantageously high.

The amount of compound (III) to be used is preferably 1 to 10 equivalents, more preferably 1 to 2 equivalents, relative to compound (II). The amount of compound (IV) to be used is preferably 1 to 20 equivalents, more preferably 1 to 5 equivalents, relative to compound (II).

In Production Method 2, a desiccating agent is preferably added to promote the reaction. As the desiccating agent, molecular sieve, silica gel, celite and the like can be mentioned, with preference given to molecular sieve 4 Å. The amount of the desiccating agent to be used is preferably 0.5 to 40-fold weight, more preferably 1 to 10-fold weight, relative to compound (II).

In Production Method 2, a base is preferably added to promote the reaction. As the base, tertiary amine can be used. For example, triethylamine, diisopropylethylamine and the like can be mentioned. The amount of the base to be used is preferably 0.1 to 5 equivalents, more preferably 0.4 to 2 equivalents, relative to compound (IV).

The solvent to be used in Production Method 2 is preferably one used as a solvent for complex preparation. For example, a single member of toluene, xylene, chlorobenzene, dichlorobenzene, N,N-dimethylformamide, dimethylsulfoxide, 1,2-dimethoxyethane, methyl tert-butyl ether, 1,4-dioxane, ethyl acetate, acetonitrile, chloroform, 1,2-dichloroethane, dichloromethane, water, alcohol solvents such as methanol, ethanol, n-propanol, isopropanol, butanol and the like or a mixed solvent thereof can be mentioned. The amount of the solvent to be used is within the range of 0.2 to 50-fold weight relative to compound (II).

The reaction temperature is generally −78° C. to 130° C., with preference given to −20° C. to 40° C. When the reaction temperature is low' stereo selectivity tends to increase but the reaction rate become low. While the reaction time varies depending on the reagent and reaction temperature to be employed, it is generally 1 hr to 300 hrs.

The obtained compound (V) can be isolated and purified by a conventional method. The compound (V) can be isolated and purified by, for example, subjecting the mixture after extraction or the reaction mixture directly to silica gel column chromatography.

The compound (V) wherein $R^8$ and $R^9$ form 4-piperidinone together with the adjacent nitrogen atom, which is obtained in Production Method 2, namely, compound (Va), is a preferable embodiment because it can be converted to compound (Vb), which is a primary propargylamine, by deprotecting 4-piperidinone ring as shown in the following scheme.

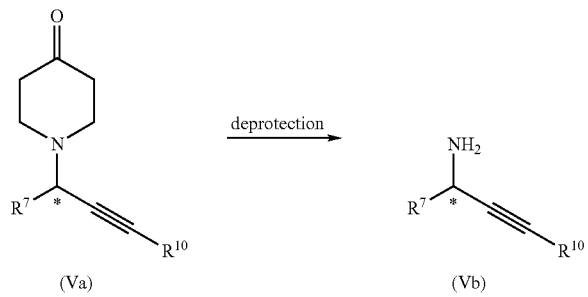

wherein each symbol is as defined above.

Such method for converting to primary amine by deprotection of 4-piperidinone ring proceeds in a high yield while retaining the optical purity, even in the presence of an unstable group such as a triple bond. Therefore, this reaction is considered to proceed conveniently and in a high yield without side reaction, even in the presence of various unstable functional groups. In this manner, the method can be applied to general conversion of 4-piperidinone derivative to amine derivative, and is useful as a novel production method of primary amine.

The deprotection can be carried out by, for example, reacting compound (Va) with ammonia and ammonium salt in an alcohol solvent. This embodiment is explained in the following but the method is not limited to this embodiment.

As the ammonium salt to be used, ammonium chloride is preferable. The amount of the ammonium salt to be used is preferably 1 to 40 equivalents, more preferably 1 to 5 equivalents, relative to compound (Va).

The ammonia can be used in the state of saturation in the alcohol solvent to be used. As the alcohol solvent, methanol, ethanol, n-propanol, isopropanol and butanol can be used.

The amount of the alcohol solvent where the ammonia is saturated is within the range of 1 to 100-fold weight relative to compound (Va).

The reaction temperature is generally 0° C. to 130° C., with preference given to 40° C. to 100° C. While the reaction time varies depending on the reagent and reaction temperature to be employed, it is generally 0.5 hr to 48 hrs.

The obtained compound (Vb) can be isolated and purified by a conventional method compound. (Vb) can be isolated and purified by, for example, subjecting the mixture after extraction or the reaction mixture directly to silica gel column chromatography.

One embodiment of the asymmetric hydroboration reaction is shown in the following reaction scheme as Production Method 3. In Production Method 3, compound (VIII) can be produced by, for example, reacting compound (VI) and boron compound (VII) as substrates, with the asymmetric transition metal complex of the present invention as an asymmetric catalyst in a solvent. In this case, the asymmetric transition metal complex is preferably one prepared by the reaction of optically active compound (I) and $Rh(cod)_2X^1$ (wherein $X^1$ and cod are as defined above).

Production Method 3

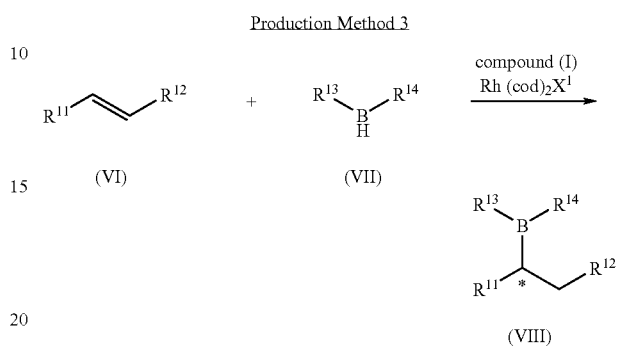

wherein each symbol and abbreviations are as defined above.

In Production Method 3, the order of the addition of the reagents is not particularly limited. Preferably, compound (VI) and boron compound (VII) are sequentially or simultaneously added to a solution in which a catalyst has been dissolved.

The amount of the asymmetric transition metal complex to be used is preferably 0.001 to 2 equivalents, more preferably 0.01 to 0.2 equivalent, relative to compound (VI). While the reaction can be carried out even when the amount of the asymmetric transition metal complex to be used is outside this range, when the amount is less than this range, the reaction may not completed and when the amount is higher, the cost becomes disadvantageously high.

While boron compound (VII) to be used in Production Method 3 is not particularly limited, catecholborane, pinacolborane and the like can be mentioned, with preference given to catecholborane. As used herein, boron compound (VII) is preferably purified by distillation etc. before use. The amount of boron compound (VII) to be used is preferably 1 to 10 equivalents, more preferably 1 to 3 equivalents, relative to compound (VI).

The solvent to be used in the hydroboration reaction may be any as long as it does not inhibit the reaction and, for example, a single member of toluene, tetrahydrofuran, xylene, chlorobenzene, dichlorobenzene, 1,2-dimethoxyethane, methyl tert-butyl ether, 1,4-dioxane and the like or a mixed solvent thereof can be mentioned. The amount of the solvent to be used is within the range of 0.2 to 50-fold weight relative to compound (VI).

The reaction temperature is generally −78° C. to 120° C., with preference given to −20° C. to 40° C. While the reaction time varies depending on the reagent and reaction temperature to be employed, it is generally 0.1 hrs to 40 hrs.

Since the obtained compound (VIII) is unstable, the reaction mixture is generally applied to the subsequent step without isolation and purification, whereby a useful optically active compound can be obtained.

The compound (IX) can be obtained by, for example, adding ethanol and the like to the reaction mixture containing compound (VIII) to stop the reaction, and then adding an oxidant to allow reaction, or by adding an oxidant directly to the reaction mixture.

As the oxidant, an aqueous hydrogen peroxide solution is generally used. At this time, an aqueous sodium hydroxide solution and the like are preferably added thereto. The amount of the oxidant to be used is preferably 5 to 60 equivalents, more preferably 10 to 40 equivalents, relative to the compound (VI).

The reaction temperature of the oxidization is generally −78° C. to 50° C., with preference given to −20° C. to 30° C. While the reaction time varies depending on the reagent and reaction temperature to be employed, it is generally 0.5 hr to 24 hrs.

The obtained compound (IX) can be isolated and purified cation according to a conventional method. For example, isolation and purification can be carried out by subjecting to silica gel column chromatography and the like after extraction and the like.

As shown in the following scheme, compound (X) can be produced by reacting compound (VIII) with hydroxylamine-O-sulfonic acid (i.e., sulfuric acid ester of hydroxylamine), according to the method described in J. M. Chem. Eur. J., 2000, 6, p. 1840-1846, compound (XII) can be produced by reacting compound (VIII) with compound (XI) and then reacting with an aqueous hydrogen peroxide solution, according to the method described in J. Org. Chem., 1999, 64, p. 9704-9710, and compound (XIV) can be produced by reacting compound (VIII) with compound (XIII) and then reacting sodium chlorite.

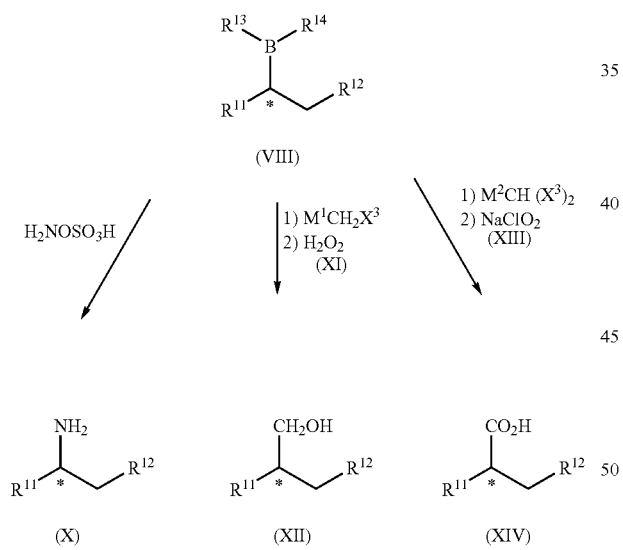

wherein each symbol is as defined above.

One embodiment of the asymmetric diboration reaction is shown in the following reaction scheme as Production Method 4. In Production Method 4, compound (XVII) and compound (XVIII) can be produced according to the method described in J. Am. Chem. Soc., 2003, 125, p. 8702-8703 using optically active compound (I) instead of QUINAP. In this case, the asymmetric transition metal complex is preferably one prepared by the reaction of optically active compound (I) and (nbd)Rh(acac) wherein nbd and acac are as defined above.

Production Method 4

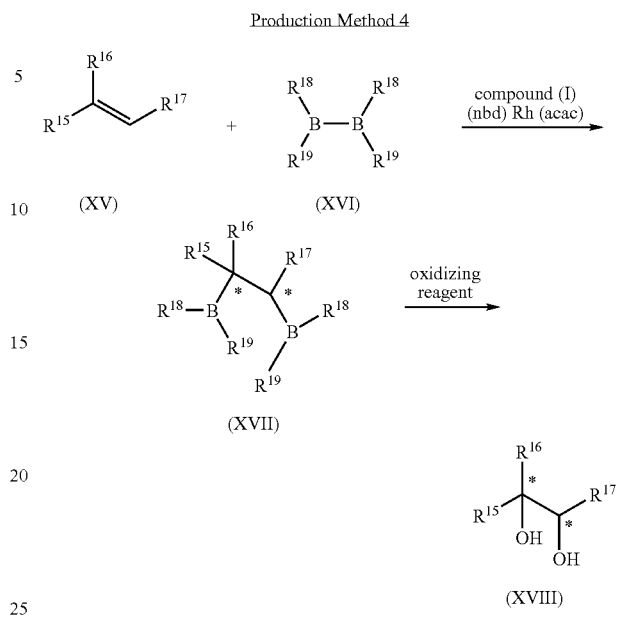

wherein each symbol and abbreviations are as defined above.

One embodiment of the asymmetric substitution reaction (Sn2') is shown in the following reaction scheme as Production Method 5. In Production Method 5, a compound represented by the formula (XXIII) can be produced according to the method described in Tetrahedron, 1994, 50, p. 4493-4506 using optically active compound (I) instead of QUINAP.

Production Method 5

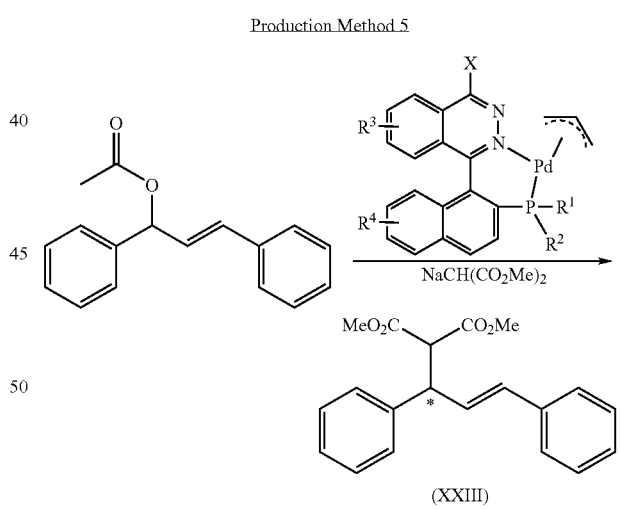

wherein each symbol is as defined above.

One embodiment of the asymmetric Diels-Alder cyclization reaction is shown in the following reaction scheme as Production Method 6. In Production Method 6, a compound represented by the formula (XXIV) can be produced according to the method described in J. Organometallics, 2001, 20, p. 2454-2458 using optically active compound (I) instead of QUINAP. In this case, the asymmetric transition metal complex is preferably one prepared by the reaction of optically active compound (I), CyRu($X^1$)$_2$ (wherein Cy and $X^1$ are as defined above) and AgSbF$_6$.

Production Method 6

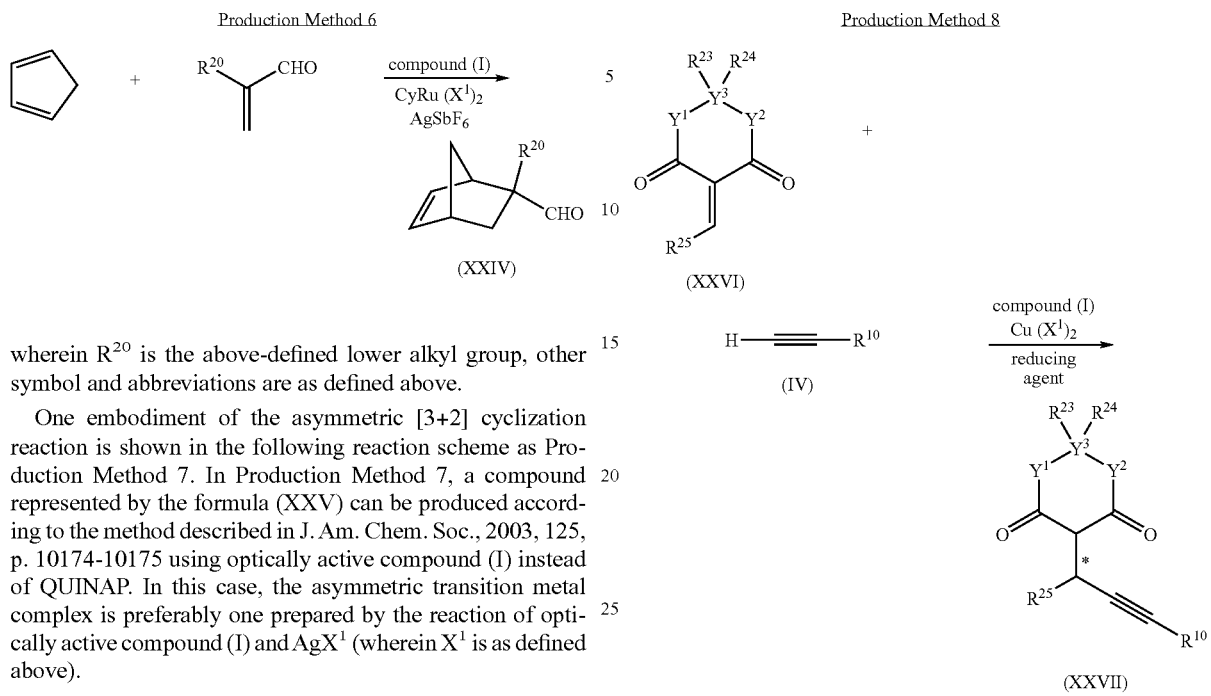

wherein $R^{20}$ is the above-defined lower alkyl group, other symbol and abbreviations are as defined above.

One embodiment of the asymmetric [3+2] cyclization reaction is shown in the following reaction scheme as Production Method 7. In Production Method 7, a compound represented by the formula (XXV) can be produced according to the method described in J. Am. Chem. Soc., 2003, 125, p. 10174-10175 using optically active compound (I) instead of QUINAP. In this case, the asymmetric transition metal complex is preferably one prepared by the reaction of optically active compound (I) and $AgX^1$ (wherein $X^1$ is as defined above).

Production Method 7

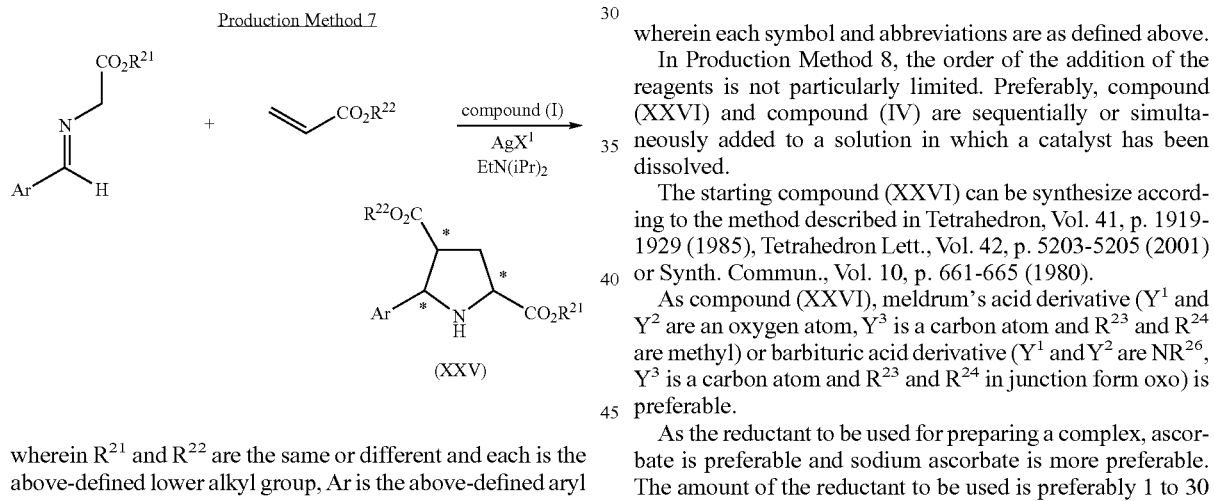

wherein $R^{21}$ and $R^{22}$ are the same or different and each is the above-defined lower alkyl group, Ar is the above-defined aryl group optionally having substituent(s) and other symbol are as defined above.

One embodiment of the asymmetric conjugate addition reaction is shown as Production Method 8 in the following reaction scheme. Production Method 8 can be carried out by applying an asymmetric transition metal complex of the present invention according to the method described in J. Am. Chem. Soc., 2003, 125, p. 6054-6055. The compound (XXVII) can be produced by, for example, reacting compound (XXVI) and compound (IV) as substrates with the asymmetric transition metal complex of the present invention as an asymmetric catalyst in a solvent. In this case, the asymmetric transition metal complex is preferably one prepared by the reaction of optically active compound (I), $Cu(X^1)_2$ (wherein $X^1$ is as defined above) and the reductant.

The compound (XXVII) is a useful synthon that can be led to various alkyne carboxylic acid derivatives by cleaving the ring structure.

Production Method 8 wherein each symbol and abbreviations are as defined above.

In Production Method 8, the order of the addition of the reagents is not particularly limited. Preferably, compound (XXVI) and compound (IV) are sequentially or simultaneously added to a solution in which a catalyst has been dissolved.

The starting compound (XXVI) can be synthesize according to the method described in Tetrahedron, Vol. 41, p. 1919-1929 (1985), Tetrahedron Lett., Vol. 42, p. 5203-5205 (2001) or Synth. Commun., Vol. 10, p. 661-665 (1980).

As compound (XXVI), meldrum's acid derivative ($Y^1$ and $Y^2$ are an oxygen atom, $Y^3$ is a carbon atom and $R^{23}$ and $R^{24}$ are methyl) or barbituric acid derivative ($Y^1$ and $Y^2$ are $NR^{26}$, $Y^3$ is a carbon atom and $R^{23}$ and $R^{24}$ in junction form oxo) is preferable.

As the reductant to be used for preparing a complex, ascorbate is preferable and sodium ascorbate is more preferable. The amount of the reductant to be used is preferably 1 to 30 equivalents, more preferably 1 to 5 equivalents, relative to $Cu(X^1)_2$.

The amount of the asymmetric transition metal complex to be used is preferably 0.01 to 1 equivalent, more preferably 0.05 to 0.5 equivalent, relative to compound (XXVI). While the reaction can be carried out even when the amount of the asymmetric-transition metal complex to be used is outside this range, when the amount is less than this range, the reaction may not be completed and when the amount is higher, the cost becomes disadvantageously high.

The amount of compound (IV) to be used is preferably 1-10 equivalents, relative to compound (XXVI).

The solvent to be used in conjugate addition reaction may be any as long as it does not inhibit the reaction, water or a mixed solvent of water and cosolvent can be mentioned. As the cosolvent, alcohol solvent such as butanol, isopropanol, ethanol, methanol and the like, tetrahydrofuran, acetonitrile, dioxane, ethyl acetate, toluene and the like or a mixed solvent thereof can be mentioned. The amount of the solvent to be used is such an amount that makes the concentration of the reaction solution 0.1 M to 10 M.

The reaction temperature is generally −20° C. to 100° C., with preference given to −20° C. to 40° C. While the reaction time varies depending on the reagent and reaction temperature to be employed, it is generally 1 hr to 120 hrs.

The obtained compound (XXVII) can be isolated and purified by a conventional method. Compound (XXVII) can be isolated and purified by, for example, subjecting the mixture after extraction or the reaction mixture directly to silica gel column chromatography.

EXAMPLES

The present invention is explained in more detail in the following by referring to Examples, which are not to be construed as limitative.

In NMR data, J is a value in Hz.

Reference Example 1

1-(4-Chlorophthalazin-1-yl)-naphthalen-2-ol

To a solution of 1,4-dichlorophthalazine (9.96 g, 50 mmol) in dichloroethane (180 ml) was added 2-naphthol (7.24 g, 50 mmol) and aluminum chloride (7.38 g, 55 mmol) and the mixture was stirred at 80° C. for 17 hrs. The dark red solution was poured in ice water (600 ml) and the resulting brown suspension was stirred vigorously for 1 hr. The solid was collected by filtration, washed with diethyl ether and dried to give 11.8 g of the title compound as a beige solid. (Yield: 77%)

$^1$H-NMR (300MHz, DMSO-$d_6$) δ: 6.99 (d, J=8.0, 1H), 7.24-7.35 (m, 2H), 7.37 (d, J=8.9, 1H), 7.49 (d, J=8.3, 1H), 7.91-8.01 (m, 2H), 8.04 (d, J=9.0, 1H), 8.13-8.19 (m, 1H), 8.41 (d, J=8.4, 1H), 9.94 (s, 1H).

Reference Example 2

1-(4-Chlorophthalazin-1-yl)-7-methoxy-naphthalen-2-ol

In a 1 L flask under nitrogen were mixed 1,4-dichlorophthalazine (11.4 g, 57.3 mmol) with 7-methoxy-naphthalen-2-ol (10.0 g, 57.5 mmol). To this was added 1,2-dichloroethane (450 ml). After stirring for 10 min, aluminum chloride (7.64 g, 57.4 mmol) was added. The resulting suspension was stirred for 20 hrs at 80° C. After cooling to room temperature, the black suspension was poured on ice-water (500 ml) and stirred for 1 hr. The two layers were separated. The aqueous layer was extracted with dichloromethane (3×200 ml). The combined organic layers were dried over sodium sulfate and concentrated under reduced pressure. The crude solid was triturated with dichloromethane (35 ml) for 1 hr and collected by filtration to give 15.2 g of the title compound as a grey solid. (Yield: 80%)

mp: >210° C.

$^1$H-NMR (300 MHz, DMSO-$d_6$) δ 3.50 (s, 3H), 6.33 (d, J=2.4, 1H), 7.01 (dd, J=2.4, J=8.7, 1H), 7.20 (d, J=8.7, 1H), 7.52 (d, J=8.4, 1H), 7.86 (d, J=9.0, 1H), 7.94 (d, J=8.7, 1H), 7.96-8.02 (m, 1H), 8.13-8.18 (m, 1H), 8.40 (d, J=8.4, 1H).

$^{13}$C-NMR (75 MHz, DMSO-$d_6$) δ 55.6, 103.6, 113.9, 115.5, 116.2, 123.9, 125.6, 126.1, 127.4, 129.1, 130.5, 131.5, 134.9, 135.0, 135.5, 154.7, 154.8, 158.8, 159.2.

FTIR (thin film, cm$^{-1}$): 3017 (w), 1625 (m), 1513 (s), 1462 (w), 1342 (m), 1290 (m), 1221 (s), 772 (s).

HRMS (ESI, pos.) calcd for $C_{19}H_{13}N_2O_2Cl$ (M+H)$^+$ 337.07. found 337.07.

Anal. Calcd for $C_{19}H_{13}N_2O_2Cl$: C, 67.76; H, 3.89. Found: C, 67.58; H, 4.13.

Reference Example 3

5-(Cyclopropylmethylene)-2,2-dimethyl-1,3-dioxane-4,6-dione

A 0.5 M solution (13 ml, 6.6 mmol) of cyclopropylmagnesiumbromide in tetrahydrofuran was added dropwise to a solution of 5-dimethylaminomethylene-2,2-dimethyl-1,3-dioxane-4,6-dione (1.0 g, 5.0 mmol) in tetrahydrofuran (12 ml) at 23° C. After stirring the mixture for 1 hr, the reaction solution was quenched with saturated aqueous ammonium chloride solution. The organic layer was separated and the water layer was extracted with dichloromethane. The combined organic layers were washed with water and brine, dried over sodium sulfate and concentrated under reduced pressure. The residue was purified by flash chromatography on silica gel (hexane/EtOAc 5:1) followed by crystallization from hexane to give 498 mg of the pure title product as a pale yellow powder. (yield: 51%)

mp: 91-92° C.

$^1$H-NMR (300 MHz, CDCl$_3$) δ 1.06-1.12 (m, 2H), 1.42-1.49 (m, 2H), 1.73 (s, 6H), 3.15-3.25 (m, 1H), 7.18 (d, J=11.9, 1H).

$^{13}$C-NMR (75 MHz, CDCl$_3$) δ 14.2, 16.8, 27.7, 104.6, 114.5, 160.8, 162.2, 174.2.

FTIR (thin film, cm$^{-1}$) : 2998 (w), 1725 (s), 1603 (s), 1396 (s) 1276 (s), 1201 (s), 1005 (m), 931 (s), 856 (m), 796 (m).

MS (ESI, pos.) calcd for $C_{10}H_{12}NaO_4^+$ (M+Na$^+$) 219.1, found 219.1.

Anal. Calcd for $C_{10}H_{12}O_4$: C, 61.22; H, 6.16. Found: C, 61.19; H, 6.21.

Example 1

(R)-1-[4-(1-Phenylethoxy)-phthalazin-1-yl]-naphthalen-2-ol

To a suspension of sodium hydride (1.21 g, 50.4 mmol) in tetrahydrofuran (100 ml) was added a solution of (R)-phenylethanol (3.11 g, 25.5 mmol) in tetrahydrofuran (5 ml) cautiously over 10 min at 23° C. The mixture was stirred for 15 min, then 1-(4-chlorophthalazin-1-yl)-naphthalen-2-ol (7.66 g, 25.0 mmol) was added portionwise. The resulting red suspension was stirred for 26 hrs at 23° C. and then the solvent was removed under reduced pressure. The residue was dissolved in dichloromethane and poured into brine. The organic layer was separated and the aqueous layer was extracted twice with dichloromethane. The combined organic layers were dried over sodium sulfate and concentrated under reduced pressure. The residue was purified by flash chromatography on silica gel (hexanes/EtOAc 5:1 to 2:1) to give 8.07 g of the title compound (2) as a 1:1 mixture of diastereomers, as a white foam. (Yield: 82%)

$^1$H-NMR (400MHz, CDCl$_3$) δ: 1.80 (d, J=6.5, 3H), 1.82 (d, J=6.5, 3H), 6.63-6.70 (m, 2H), 7.05-7.38 (m, 15H), 7.49-7.57 (m, 7H), 7.66-7.80 (m, 5H), 8.30-8.37 (m, 2H).

$^{13}$C-NMR (100 MHz, CDCl$_3$) δ: 22.6, 22.7, 74.6, 74.7, 114.5, 114.6, 119.4, 119.6, 120.6, 120.7, 123.0, 123.1, 123.1, 124.6, 124.6, 126.2, 126.2, 126.3, 126.9, 127.0, 127.8, 127.8, 128.0, 128.1, 128.5, 128.5, 128.6, 128.6, 129.3, 129.3, 130.9, 132.0, 132.1, 132.1, 132.2, 133.3, 133.3, 142.2, 142.3, 153.8, 153.8, 154.2, 154.2, 159.5, 159.5.

HRMS (MALDI) calcd. for $C_{26}H_{21}N_2O_2$ $[M+H]^+$ 393.1598. found 393.1603.

Anal. Calcd for $C_{26}H_{20}N_2O_2$: C, 79.57; H, 5.14; N, 7.14. Found: C, 79.42; H, 5.25; N, 7.21.

Example 2

Trifluoromethanesulfonic acid (R)-1-[4-(1-phenylethoxy)-phthalazin-1-yl]-naphthalen-2-yl ester To a solution of (R)-1-[4-(1-phenylethoxy)-phthalazin-1-yl]-naphthalen-2-ol (0.91 g, 2.3 mmol) in pyridine (0.56 ml, 6.9 mmol) and dichloromethane (10 ml) was added dropwise trifluoromethanesulfonic anhydride (0.41 ml, 2.4 mmol) at 0° C.

The resulting solution was stirred at 0° C. for 2 hrs and quenched with sat. aqueous ammonium chloride solution. The organic layer was separated and the aqueous layer was washed twice with dichloromethane. The combined organic layers were dried over sodium sulfate and concentrated. The residue was purified by flash chromatography on silica gel (toluene/hexanes 20:1) to give 1.1 g of the title compound as a white foam. (Yield: 91%)

$^1$H-NMR (400 MHz, CDCl$_3$) δ: 1.89 (d, J=6.5, 3H), 1.91 (d, J=6.5, 3H), 6.87 (sextet, J=6.5, 2H), 7.27-7.47 (m, 12H), 7.53-7.64 (m, 6H), 7.65-7.71 (m, 4H), 7.85-7.90 (m, 2H), 7.97-8.01 (m, 2H), 8.09-8.13 (m, 2H), 8.43-8.46 (m, 2H).

$^{13}$C-NMR (100 MHz, CDCl$_3$) δ: 22.4, 22.5, 74.8, 74.9, 118.0 (q, $J_{CF}$=320), 118.2 (q, $J_{CF}$=320), 119.5, 119.6, 120.0, 123.4, 123.4, 125.4, 125.4, 125.9, 126.1, 126.3, 126.4, 126.4, 126.5, 126.5, 126.7, 127.2, 127.4, 127.7, 127.8, 127.9, 128.2, 128.3, 128.4, 128.5, 129.1, 129.1, 131.6, 131.7, 132.1, 132.1, 132.3, 132.4, 132.4, 132.4, 133.3, 133.3, 133.5, 142.2, 142.4, 145.3, 145.4, 150.5, 150.6, 159.7, 159.7.

HRMS (MALDI) calcd. for $C_{27}H_{20}F_3N_2O_4S$ $[M+H]^+$ 525.1090. found 525.1085.

Example 3

(R,Sax)-1-(2-Diphenylphosphanylnaphthalen-1-yl)-4-(1-phenylethoxy)-phthalazine and (R,Rax)-1-(2-Diphenylphosphanylnaphthalen-1-yl)-4-(1-phenylethoxy)-phthalazine To a solution of NiCl$_2$(dppe) (201 mg, 0.381 mmol) in N,N-dimethylformamide (20 ml) was added diphenylphosphine (1.33 ml, 2.63 mmol) at 23° C. The resulting dark red solution was stirred at 100° C. for 1 hr. Then a solution of trifluoromethanesulfonic acid (R)-1-[4-(1-phenylethoxy)-phthalazin-1-yl]-naphthalen-2-yl ester (2.00 g, 3.81 mmol) and 1,4-diazabicyclo[2.2.2]octane (1.71 g, 15.3 mmol) in N,N-dimethylformamide (20 ml) was added via canula. The resulting dark green solution was stirred at 100° C. for 11 hrs. The mixture was allowed to cool to 23° C. and then diethyl ether (400 ml) was added quickly. The resulting mixture was washed with water and brine (300 ml each). The organic layer was poured into silica gel and concentrated under reduced pressure. The residue was purified by flash chromatography on silica gel (toluene/EtOAc 10:1) to give 1.21 g of the title compounds as an off-white solid (1:1 mixture of diastereomers, Yield: 55%). The diastereomers were separated by flash chromatography on silica gel (toluene/EtOAc 200:3).

An X-ray grade sample (colorless plate) was obtained after recrystallizing (R,Sax)-1-(2-diphenylphosphanylnaphthalen-1-yl)-4-(1-phenylethoxy)-phthalazine from diethyl ether-hexane. X-ray crystallography proved its configuration about axial chirality as S. (R,Sax)-1-(2-Diphenylphosphanylnaphthalen-1-yl)-4-(1-phenylethoxy)-phthalazine:

mp: 179-180° C.

$[\alpha]_D^{27}$=−160.4 (c=0.53, CHCl$_3$).

$^1$H-NMR (400 MHz, CDCl$_3$) δ: 1.84 (d, J=6.5, 3H), 6.84 (q, J=6.5, 1H), 7.06 (d, J=8.2, 1H), 7.11-7.32 (m, 13H), 7.35-7.48 (m, 5H), 7.61-7.65 (m, 1H), 7.71-7.76 (m, 1H), 7.85 (d, J=8.2, 1H), 7.88 (d, J=8.3, 1H), 8.35 (d, J=8.2, 1H).

$^{13}$C-NMR (100 MHz, CDCl$_3$) δ: 22.6 (CH$_3$), 74.4 (CH), 119.8 (C), 123.1 (CH), 126.0 (CH), 126.5 (CH), 126.6 (CH), 126.6 (CH), 126.7 (CH), 126.9 (CH), 127.6 (CH), 127.9 (CH), 128.1 (CH), 128.2 (CH), 128.3 (CH), 128.3 (CH), 128.3 (CH), 128.4 (CH), 128.5 (CH), 129.1 (CH), 129.9 (C), 129.9 (C), 130.1 (CH), 131.4 (CH), 131.6 (CH), 133.0 (C), 133.0 (C), 133.1 (CH), 133.3 (CH), 133.5 (C), 133.7 (CH), 133.9 (CH), 135.8 (C), 135.9 (C), 137.1 (C), 137.2 (C), 137.3 (C), 137.5 (C), 141.0 (C), 141.4 (C), 142.7 (C), 156.2 (C), 156.3 (C), 159.2 (C).

$^{31}$P-NMR (121 MHz, CDCl$_3$) δ: 13.2.

FTIR (KBr, cm$^{-1}$): 1581 (m), 1537 (m), 1493 (m), 1479 (m), 1378 (s), 1358 (s), 1310 (s), 1056 (m), 884 (m), 819 (m) 741 (s), 692 (s).

HRMS (MALDI) calcd. for $C_{39}H_{29}N_2OP$ $[M+H]^+$ 561.2090. found 561.2089.

Anal. Calcd for $C_{38}H_{29}N_2OP$: C, 81.41; H, 5.21; N, 5.00. Found: C, 81.14; H, 5.32; N, 4.84.

(R,Rax)-1-(2-Diphenylphosphanylnaphthalen-1-yl)-4-(1-phenylethoxy)-phthalazine:

mp: 64-65° C.

$[\alpha]_D^{25}$=78.5(c=0.25, CHCl$_3$).

$^1$H-NMR (400 MHz, CDCl$_3$) δ: 1.88 (d, J=6.5, 3H), 6.83 (q, J=6.5, 1H), 7.07-7.76 (m, 14H), 7.39-7.52 (m, 5H), 7.63-7.67 (m, 2H), 7.72-7.78 (m, 1H), 7.87-7.92 (m, 2H), 8.33-8.37 (m, 1H).

$^{13}$C-NMR (100 MHz, CDCl$_3$) δ: 22.5 (CH$_3$), 74.4 (CH), 119.8 (C), 123.1 (CH), 126.0 (CH), 126.5 (CH), 126.5 (CH), 126.5 (CH), 126.7 (CH), 126.9 (CH), 127.7 (CH), 128.0 (CH), 128.2 (CH), 128.2 (CH), 128.2 (CH), 128.2 (CH), 128.3 (CH), 128.4 (CH), 128.4 (CH), 129.0 (CH), 129.9 (C), 129.9 (C), 130.0 (CH), 131.4 (CH), 131.7 (CH), 133.0 (C), 133.0 (C), 133.1 (C), 133.3 (CH), 133.5 (CH), 133.6 (CH), 133.8 (CH), 136.2 (C), 136.3 (C), 136.8 (C), 136.9 (C), 137.3 (C), 137.4 (C), 140.7 (C), 141.0 (C), 142.6 (C), 156.2 (C), 156.2 (C), 159.3 (C).

$^{31}$P-NMR (121 MHz, CDCl$_3$) δ: −12.3

FTIR (KBr, cm$^{-1}$): 1582 (m), 1537 (m), 1491 (m), 1433 (m), 1410 (m), 1378 (s), 1307 (s), 1164 (w), 1111 (w), 1068 (m), 817 (w), 742 (s), 693 (s).

HRMS (MALDI) calcd. for $C_{39}H_{29}N_2OP$ $[M+H]^+$ 561.2090. found 561.2085.

Anal. Calcd for $C_{38}H_{29}N_2OP$: C, 81.41; H, 5.21; N, 5.00. Found: C, 81.34; H, 5.49; N, 4.86.

Example 4

(R,Sax)-1-[2-Di(p-tolyl)phosphanylnaphthalen-1-yl]-4-[1-phenylethoxy]phthalazine and (R,Rax)-1-[2-Di(p-tolyl)phosphanylnaphthalen-1-yl]-4-[1-phenylethoxy]phthalazine A mixture of di(p-tolyl)phosphine (300 mg, 1.4 mmol), NiCl$_2$(dppe) (37 mg, 0.07 mmol) and N,N-dimethylformamide (2 ml) was stirred at 100° C. under argon atmosphere for 0.5 hr. A solution of trifluoromethanesulfonic acid (R)-1-[4-(1-phenylethoxy)-phthalazin-1-yl]-naphthalen-2-yl ester (367 mg, 0.7 mmol) in N,N-dimethylformamide (1 ml) was added to a solution of 1,4-diazabicyclo[2.2.2]octane (314 mg, 2.8 mmol) in N,N-dimethylformamide (1 ml), and this mixture was transferred in one portion to the above-mentioned reaction flask via cannula. The resulting mixture was stirred at 100° C. for 24 hrs. The mixture was cooled to 0° C., poured into water (10 ml) and extracted twice with diethyl ether (10 ml). The organic layer was washed with water (10 ml) and brine (10 ml), and dried over sodium sulfate. The solvent was removed in vacuo. The residue was purified by chromatography on silica gel (toluene/AcOEt=100/1, v/v) to give 175 mg of the title compound as a mixture of two diastereomers (less polar diastereomer/more polar diastereomer=1/1.1). (yield: 42%) Then the diastereomeric mixture was subjected to chromatography on silica gel (toluene/EtOAc=200/1-100/1, v/v) to give the less polar diastereomer (55.1 mg, 0.094 mmol) as white amorphous powder. More polar diastereomer was not yet pure enough for characterization.

less polar diastereomer:

$^1$H-NMR (400 MHz, CDCl$_3$) δ: 1.58 (3H, d, J=6.5 Hz), 2.28 (3H, s), 2.32 (3H, s), 6.85 (1H, q, J=6.5 Hz), 6.97-7.45 (17H, m), 7.64 (2H, d, J=6.8 Hz), 7.45 (1H, t, J=7.2 Hz), 7.87 (2H, t, J=7.2 Hz), 8.35 (1H, d, J=8.4 Hz).

$^{31}$P-NMR (121 MHz, CDCl$_3$) δ: −14.20.

HRMS (MALDI) Calcd for $C_{40}H_{33}N_2OP^+H$: 589.2409. Found: M$^+$H=589.2397.

Example 5

(R,Sax)-1-(2-Dicyclohexylphosphanylnaphthalen-1-yl)-4-[1-phenylethoxy]phthalazine and (R,Rax)-1-(2-Dicyclohexylphosphanylnaphthalen-1-yl)-4-[1-phenylethoxy]phthalazine In a dried 10 ml Schlenk flask, a mixture of dicyclohexylphosphine (139 mg, 0.7 mmol), NiCl$_2$(dppe) (18.5 mg, 0.035 mmol), and N,N-dimethylformamide (2 ml) was stirred at 100° C. under argon atmosphere for 0.5 hr. A solution of trifluoromethanesulfonic acid (R)-1-[4-(1-phenylethoxy)-phthalazin-1-yl]-naphthalen-2-yl ester (138.6 mg, 0.35 mmol) in N,N-dimethylformamide (1 ml) was added to the solution of 1,4-diazabicyclo[2.2.2]octane (157 mg, 1.4 mmol) in N,N-dimethylformamide (1 ml), and this mixture was transferred in one portion to the above-mentioned reaction flask via cannula. The resulting mixture was stirred at 100° C. for 20 hrs. The mixture was cooled to 0° C., poured into water (10 ml) and extracted twice with diethyl ether (10 ml). The organic layer was washed with water (10 ml) and brine (10 ml), and dried over sodium sulfate. The solvent was removed in vacuo. The residue was purified by chromatography on silica gel (toluene/AcOEt=100/1, v/v) to give 14.4 mg of the title compound as a mixture of two diastereomers (less polar diastereomer/more polar diastereomer=1/1). (yield: 7.2%)

a mixture of diastereomers:

$^1$H-NMR (400 MHz, CDCl$_3$) δ: 0.72-2.19 (26H, m), 1.87 (1.55H, d, J=6.5 Hz), 1.90 (1.5H, d, J=6.5 Hz), 6.82 (0.5H, q, J=6.5 Hz), 6.88 (0.5H, q, J=6.5 Hz), 7.02-8.39 (15H, m).

$^{31}$P-NMR (121 MHz, CDCl$_3$) δ: −9.228, 9.284.

HRMS (MALDI) Calcd for $C_{38}H_{41}N_2OP^+H$: 573.3035. Found: M$^+$H=589.3023.

Example 6

7-Methoxy-1-[4-((R)-1-phenyl-ethoxy)-phthalazin-1-yl]-naphthalen-2-ol

To a suspension of sodium hydride (0.80 g, 33 mmol) in tetrahydrofuran (80 ml) was added a solution of (R)-phenylethanol (2.0 g, 17 mmol) in tetrahydrofuran (3 ml) cautiously over 10 min at 23° C. The mixture was stirred for 15 min, then 1-(4-chlorophthalazin-1-yl)-7-methoxy-naphthalen-2-ol (5.1 g, 15 mmol) was added portionwise. The resulting red suspension was stirred for 20 hrs at 23° C., then the solvent was removed under reduced pressure. The residue was dissolved in dichloromethane and poured into brine. The organic layer was separated and the aqueous layer was extracted two times with dichloromethane. The combined organic layers were dried over sodium sulfate and concentrated under reduced pressure. The residue was purified by flash chromatography on silica gel (hexane/EtOAc 4:1 to 1:1) to give 5.5 g (13 mmol) of the title compound as a 1:1 mixture of diastereomers, as a white foam.

HRMS (MALDI, pos.) calcd. for $C_{27}H_{22}N_2O_3$ [M+H] 423.16. found: 423.17.

Example 7

Perfluoro-1-butanesulfonic acid 7-methoxy-1-[4-((R)-1-phenyl-ethoxy)-phthalazin-1-yl)-naphthalen-2-yl ester A solution of 7-methoxy-1-[4-((R)-1-phenyl-ethoxy)-phthalazin-1-yl]-naphthalen-2-ol (1.0 g, 2.4 mmol) in diisopropylethylamine (0.94 ml, 7.1 mmol) and dichloromethane (35 ml) was treated with N,N-dimethylaminopyridine (DMAP, 50 mg, 0.41 mmol) at 0° C. Then perfluoro-1-butanesulfonyl fluoride (0.51 ml, 2.8 mmol) was added dropwise and the resulting solution was stirred for 19 hrs at 23° C. The resulting solution was quenched with sat. aqueous ammonium chloride solution. The organic layer was separated and the water layer was extracted twice with dichloromethane. The combined organic layers were dried over sodium sulfate and concentrated under reduced pressure. The residue was purified by flash chromatography on silica gel (hexane/EtOAc 3:1) to give 1.4 g (2.0 mmol) of the title compound as an oil.

HRMS (MALDI, pos.) calcd for $C_{31}H_{21}F_9N_2O_5S$ (M+H) 705.10. found 705.11.

Example 8

1-(2-Diphenylphosphanyl-7-methoxynaphthalen-1-yl)-4-((R)-1-phenyl-ethoxy)-phthalazine A solution of NiCl$_2$(dppe) (0.24 g, 0.46 mmol) in N,N-dimethylformamide (10 ml) was treated with diphenylphosphine (1.6 ml, 9.2 mmol) at 23° C. The resulting dark red solution was stirred at 120° C. for 30 min. Then a solution of perfluorobutanesulfonic acid 7-methoxy-1-[4-((R)-1-phenyl-ethoxy)-phthalazin-1-yl]-naphthalen-2-yl ester (2.3 g, 4.2 mmol) and 1,4-diazabicyclo[2.2.2]octane (DABCO, 2.1 g, 18 mmol) in N,N-dimethylformamide (18 ml) was added via a syringe, the flask was washed with N,N-dimethylformamide (2 ml). The resulting green solution was stirred at 105° C. for 17 hrs. The mixture was concentrated under reduced pressure (20 mbar, 70° C. bath temperature). The residue was purified by flash chromatography on silica gel (toluene→toluene/EtOAc 10:1) to give 1.4 g (2.3 mmol) of the title compounds as an oil as a 1:1 mixture of diastereomers.

Separation of the diastereomers was performed by flash chromatography on silica gel (toluene→toluene/EtOAc 10:1).

(1st Diastereomer)

HRMS (MALDI, pos.) calcd for $C_{39}H_{31}N_2O_2P$ (M+H) 591.21. found 25 591.22.

$[\alpha]_D^{31} = -102.3$ (c=0.50, $CHCl_3$)

(2nd Diastereomer)

HRMS (MALDI, pos.) calcd for $C_{39}H_{31}N_2O_2P$ (M+H) 591.21. found 591.22.

$[\alpha]_D^{29} = 16.9$ (c=0.50, $CHCl_3$)

Example 9

Trifluoromethanesulfonic acid 1-(4-chlorophthalazin-1-yl)-naphthalen-2-yl ester

To a suspension of 1-(4-chlorophthalazin-1-yl)-naphthalen-2-ol (1.0 g, 3.3 mmol) and pyridine (0.80 ml, 9.8 mmol) in dichloromethane (10 ml) was added dropwise trifluoromethanesulfonic anhydride (0.58 ml, 3.4 mmol) at 0° C. over 2 hrs. The resulting solution was quenched with sat. aqueous ammonium chloride solution. The organic layer was separated and the water layer was extracted twice with dichloromethane. The combined organic layers were dried over sodium sulfate and concentrated under reduced pressure. The residue was purified by flash chromatography on silica gel (hexanes:EtOAc 3:1) to give 1.3 g of the title compound as a light brown foam. (yield: 93%)

mp: 54-55° C. (foam).

$^1$H-NMR (300 MHz, $CDCl_3$) δ: 7.27 (d, J=6.9, 1H), 7.41-7.47 (m, 2H), 7.57-7.66 (m, 2H), 7.80-7.87 (m, 1H), 8.00-8.07 (m, 2H), 8.17 (d, J=9.3, 1H), 8.46 (d, J=8.4, 1H).

$^{13}$C-NMR (100 MHz, $CDCl_3$) δ: 118.0 (C, q, $J_{CF}$=312), 119.3 (CH) 125.1 (C), 125.5 (CH), 125.7 (C), 125.8 (CH), 126.2 (CH), 127.4 (CH), 128.3 (CH), 128.4 (CH), 132.3 (C),132.3 (CH), 132.8 (C), 133.8 (CH), 134.0 (CH), 145.1 (C), 155.0 (C), 155.6 (C).

FTIR (thin film, $cm^{-1}$): 3073 (w), 1583 (w), 1569 (w), 1528 (w) 1512 (m), 1423 (s), 1376 (m), 1290 (s), 1217 (s), 1138 (s), 1072 (m), 950 (s), 833 (s), 770 (m), 639 (m), 622 (m).

HRMS (MALDI) calcd. for $C_{19}H_{11}ClF_3N_2O_3S$ $[M+H]^+$ 439.0126, found 439.0131.

Anal. Calcd for $C_{19}H_{10}ClF_3N_2O_3S$: C, 52.01; H, 2.30; N, 6.38.

Found: C, 52.27; H, 2.56; N, 6.31.

Example 10

Trifluoromethanesulfonic acid (R)-1-[4-(1-phenylethylamino)-phthalazin-1-yl]-naphthalen-2-yl ester A solution of trifluoromethanesulfonic acid 1-(4-chlorophthalazin-1-yl)-naphthalen-2-yl ester (4.9 g, 11 mmol) in (R)-1-phenylethylamine (7.2 ml, 56 mmol) was stirred for 4 hrs at 120° C., then cooled to 23° C. The resulting viscous mixture was purified by flash chromatography on silica gel (toluene/EtOAc 7:1) to give 5.4 g of the title compound as a light brown solid as a 1:1 mixture of diastereomers. (yield: 93%)

$^1$H-NMR (300 MHz, $CDCl_3$) δ: 1.79 (t, J=6.7 Hz, 6H), 5.49 (d, J=7.0 Hz, 2H), 5.88 (quint, J=6.8 Hz, 2H), 7.13-7.65 (m, 22H), 7.73-7.82 (m, 2H), 7.85-7.90 (m, 2H), 7.94-8.00 (m, 2H), 8.08 (d, J=9.1 Hz, 2H).

$^{13}$C-NMR (100 MHz, $CDCl_3$) δ: 21.9, 22.0, 50.7, 50.7, 117.8, 117.8, 118.0 (q, $J_{CF}$=320), 118.7 (q, $J_{CF}$=320), 119.4, 119.5, 120.8, 126.1, 126.1, 126.4, 126.5, 126.7, 126.7, 127.1, 127.2, 127.2, 127.4, 127.5, 127.5, 127.7, 128.1, 128.2, 128.5, 128.6, 131.3, 131.3, 131.4, 131.4, 131.4, 131.5, 132.5, 132.5, 133.6, 133.6, 144.0, 144.3, 145.5, 145.6, 146.5, 146.5, 152.7, 152.8.

HRMS (MALDI) calcd. for $C_{27}H_{21}F_3N_3O_3S$ $[M+H]^+$ 524.1250, found 524.1258.

Anal. Calcd for $C_{27}H_{20}F_3N_3O_3S$: C, 61.94; H, 3.85; N, 8.03. Found: C, 62.15; H, 3.99; N, 7.79.

Example 11

(R,Sax)-[4-(2-Diphenylphosphanylnaphthalen-1-yl)-phthalazin-1-yl]-(1-phenylethyl)-amine and (R,Rax)-[4-(2-Diphenylphosphanyl-naphthalen-1-yl)-phthalazin-1-yl]-(1-phenyl-ethyl)-amine To a solution of $NiCl_2$(dppe) (540 mg, 1.0 mmol) in N,N-dimethylformamide (40 ml) was added diphenylphosphine-(3.6 ml, 20 mmol) at 23° C. The resulting dark red solution was stirred at 100° C. for 1 hr. Then a solution of trifluoromethanesulfonic acid (R)-1-[4-(1-phenylethylamino)-phthalazin-1-yl]-naphthalen-2-yl ester (5.3 g, 10 mmol) and 1,4-diazabicyclo[2.2.2]octane (4.6 g, 41 mmol) in N,N-dimethylformamide (40 ml) was added via canula. The resulting dark green solution was stirred at 100° C. for 15 hrs. Then the N,N-dimethylformamide was evaporated at 50° C., the residue was purified by flash chromatography on silica gel (toluene/EtOAc 10:1) to give 4.5 g of the title compounds as an off-white solid as a 2.5:1 mixture. (yield: 79%)

The mixture of diastereomers was dissolved in toluene (50 ml) and dichloromethane (100 ml). The bulk of the dichloromethane was removed under reduced pressure. Addition of hexane (50 ml) afforded 2.0 g of (R,Sax)-[4-(2-diphenylphosphanylnaphthalen-1-yl)-phthalazin-1-yl]-(1-phenylethyl)-amine as a white precipitate. (yield: 36%)

An X-ray grade sample (colorless plate) was obtained after recrystallizing the precipitate from toluene-hexane. X-ray crystallography proved its configuration about axial chirality as S.

The diastereomers included in the filtrate was separated by flash chromatography on silica gel (toluene/EtOAc 200:5). (R,Sax)-[4-(2-Diphenylphosphanylnaphthalen-1-yl)-phthalazin-1-yl]-(1-phenylethyl)-amine:

mp: >210° C.

$[\alpha]_D^{29} = -162.0$ (c=0.54, $CHCl_3$).

$^1$H-NMR (400 MHz, $CDCl_3$) δ: 1.68 (d, J=6.8, 3H), 5.34 (d, J=7.2, 1H), 5.81 (quint, J=6.9 Hz, 1H), 7.01 (d, J=8.1 Hz, 1H), 7.11-7.18 (m, 5H), 7.18-7.24 (m, 8H), 7.28-7.33 (m, 3H), 7.36-7.43 (m, 2H), 7.50-7.53 (m, 2H), 7.55-7.59 (m, 1H), 7.70 (d, J=8.3 Hz, 1H), 7.79-7.84 (m, 2H).

$^{13}$C-NMR (100 MHz, $CDCl_3$) 22.2 ($CH_3$), 50.4 (CH), 117.7 (C), 120.3 (CH), 126.5 (CH), 126.7 (CH), 126.8 (CH), 126.8 (CH), 126.9.(CH), 126.9 (CH), 127.2 (CH), 127.8 (CH), 128.0 (CH), 128.2 (CH), 128.2 (CH), 128.2 (CH), 128.3 (CH), 128.3 (C), 128.3 (C), 128.4 (CH), 128.6 (CH), 128.8 (CH), 130.1 (CH), 130.7 (CH), 130.8 (CH), 133.1 (CH), 133.2 (C), 133.3 (CH), 133.3 (C), 133.6 (C), 133.7 (CH), 133.9 (CH), 135.8 (C), 136.0 (C), 137.3 (C), 137.4 (C), 137.7 (C), 137.8 (C), 141.8 (C), 142.1 (C), 144.6 (C), 152.2 (C), 152.5 (C), 152.6 (C).

$^{31}$P-NMR (121 MHz, $CDCl_3$) δ: −13.18.

FTIR (thin film, $cm^{-1}$): 3351 (br, s), 1654 (w), 1559 (w), 1508 (s), 1420 (w), 1361 (w), 1217 (w), 820 (w), 772 (s), 698 (m).

HRMS (MALDI) calcd. for $C_{38}H_{31}N_3P^+$ $[M+H]^+$ 560.2250. found 560.2257.

Anal. Calcd for C$_{17}$H$_{21}$NO$_3$: C, 81.55; H, 5.40; N, 7.51; P, 5.53.

Found: C, 81.44; H, 5.52; N, 7.39; P, 5.67.

(R,Rax)-[4-(2-Diphenylphosphanyl-naphthalen-1-yl)-phthalazin-1-yl]-(1-phenyl-ethyl)-amine was not yet pure enough for full characterization.

$^{31}$P-NMR (121 MHz, CDCl$_3$) δ: −12.77.

HRMS (MALDI) calcd. for C$_{38}$H$_{31}$N$_3$P$^+$ [M+H]$^+$ 560.2250, found 560.2249.

Example 12

Trifluoromethanesulfonic acid 1-[4-((R)-2-ethyl-2-hydroxy-1-phenylbutylamino)phthalazin-1-yl]-naphthalen-2-yl ester To trifluoromethanesulfonic acid 1-(4-chlorophthalazin-1-yl)-naphthalen-2-yl ester (600 mg, 1.37 mmol) was added 3-((R)-aminophenyl-methyl)pentan-3-ol (1.06 g, 5.49 mmol). The resulting suspension was stirred for 24 hrs at 120° C. The mixture was purified by flash chromatography on silica gel (toluene/EtOAc 10:0→5:1) followed by crystallization from diethyl ether to give 451 mg of the title compound as a white powder as a mixture of diastereomers. (yield: 55%)

mp: 117-119° C.

$^1$H-NMR (400 MHz, CDCl$_3$) δ 0.84-1.00 (m, 12H), 1.18-1.32 (m, 2H), 1.39-1.50 (m, 2H), 1.71-1.95 (m, 4H), 2.05-2.33 (m, 2H), 5.67 (d, J=8.4, 1H), 5.7387 (d, J=8.5, 1H), 6.54-6.73 (m, 2H), 7.15-7.36 (m, 10 H), 7.43 (d, J=3.4, 1H), 7.51-7.65 (m, 9H), 7.75-7.79 (m, 2H), 7.97-8.11 (m, 6H).

$^{13}$C-NMR (125 MHz, CDCl$_3$) δ 7.6, 7.8, 8.4, 8.5, 28.1, 28.2, 29.1, 29.1, 59.1, 59.7, 78.0, 78.1, 118.1, 118.3, 118.4 (q, J$_{CF}$=318), 118.7 (q, J$_{CF}$=318), 119.9, 119.9, 121.1, 121.2, 126.2, 126.9, 127.0, 127.5, 127.6, 127.7, 127.8, 127.8, 128.2, 128.2, 128.4, 128.5, 128.6, 128.6, 129.0, 129.3, 131.7, 131.7, 131.8, 131.9, 133.0, 133.0, 133.9, 134.0, 140.6, 140.9, 145.8, 145.9, 146.5, 146.7, 153.3, 153.4.

FTIR (thin film, cm$^{-1}$): 3395 (w), 3052 (w), 2964 (w), 1508 (s), 1420 (s), 1544 (w), 1213 (s), 1138 (s).

HRMS (MALDI, pos.) calcd for C$_{32}$H$_{31}$N$_3$O$_5$F$_3$S$^+$ (M+H$^+$) 596.1825, found 596.1828.

Example 13

(R,P)-[4-(2-Diphenylphosphanyl-naphthalen-1-yl)phthalazin-1-ylamino]phenylmethyl}pentan-3-ol (1$^{st}$ diastereomer) and (R,M)-[4-(2-Diphenylphosphanyl-naphthalen-1-yl)phthalazin-1-ylamino]phenylmethyl}pentan-3-ol (2$^{nd}$ diastereomer)

A solution of NiCl$_2$(dppe) (37 mg, 0.07 mmol) in N,N-dimethylformamide (2.5 ml) was treated with diphenylphosphine (0.244 ml, 1.40 mmol) at 23° C. The resulting dark red solution was stirred at 120° C. for 30 min. A solution of trifluoromethanesulfonic acid 1-[4-((R)-2-ethyl-2-hydroxy-1-phenyl-butylamino)phthalazin-1-yl]naphthalen-2-yl ester (417 mg, 0.70 mmol) and 1,4-diazabicyclo[2.2.2]octane (DABCO, 449 mg, 2.8 mmol) in N,N-dimethylformamide (2.5 ml) was added via a syringe. The resulting green solution was stirred at 120° C. for 12 hrs. The mixture was concentrated under reduced pressure (20 mbar, 70° C. bath temperature). The residue was purified by flash chromatography on silica gel (toluene→toluene/EtOAc 5:1) to give 364 mg of the title compounds as an off-white solid as a mixture of diastereomers. (yield: 82%)

Separation of the diastereomers was performed by flash chromatography on silica gel (toluene→toluene/EtOAc 5:1)

(1$^{st}$ Diastereomer)

mp: 162-164° C.

[α]$_D^{27}$=134.9 (c=0.50, CHCl$_3$).

$^1$H-NMR (400 MHz, CDCl$_3$) δ 0.86 (t, J=7.5, 3H), 0.93 (t, J=7.6, 3H), 1.18-1.27 (m, 1H), 1.35-1.45 (m, 1H), 1.74-1.89 (m, 2H), 1.99 (bs, 1 H), 5.64 (d, J=8.4, 1H), 5.57 (d, J=8.4, 1H), 7.02 (d, J=8.0, 1H), 7.10-7.45 (m, 17H), 7.60-7.68 (m, 3H), 7.58-7.89 (m, 2H), 7.96 (d, J=8.3, 1H).

$^{13}$C-NMR (125 MHz, CDCl$_3$) δ 7.8, 8.5, 28.2, 29.1, 59.2, 78.1, 118.1, 120.9, 126.8, 126.9, 127.2, 127.6, 128.3, 128.5, 128.5, 128.5, 128.6, 128.7, 128.7, 128.7, 129.1, 129.2, 130.4, 131.2, 131.4, 133.5, 133.5, 133.7, 133.8, 133.9, 134.0, 136.3, 136.5, 137.5, 137.6, 138.2, 138.3, 141.1, 142.1, 142.4, 152.6, 152.7, 152.9.

$^{31}$P-NMR (121 MHz, CDCl$_3$) δ −12.58.

FTIR (KBr, cm$^{-1}$): 3365 (s), 3052 (m), 2965 (m), 2879 (m), 1576 (w), 1505 (s), 1478 (m), 1435 (m), 1392 (m), 1138 (w), 912 (s), 728 (s).

HRMS (MALDI, pos.) calcd for C$_{42}$H$_{39}$N$_3$O$_2$P$^+$ (M+H$^+$) 632.2825, found 632.2814.

Anal. Calcd for C$_{42}$H$_{38}$N$_3$O$_2$P: C, 79.85; H, 6.06. Found: C, 80.06; H, 6.02.

(2$^{nd}$ Diastereomer)

mp: 200° C.

[α]$_D^{26}$=−68.3 (c=0.665, CHCl$_3$)

$^1$H-NMR (400 MHz, CDCl$_3$) δ 0.89 (t, J=7.4, 3H), 0.98 (t, J=7.5, 3H), 1.23-1.32 (m, 2H), 1.39-1.48 (m, 1H), 1.76-1.95 (m, 3H), 5.68 (bs, 1H), 6.52 (bs, 1H), 6.99-7.48 (m, 17H), 7.49-7.57 (m, 1H), 7.61-7.63 (m, 2H), 7.68-7.72 (m, 1H), 7.89-7.91 (m, 2H), 7.98 (d, J=8.1, 1H).

$^{13}$C-NMR (125 MHz, CDCl$_3$) δ 7.8, 8.5, 28.2, 29.2, 59.5, 78.2, 118.2, 121.0, 126.9, 127.0, 127.2, 127.7, 128.4, 128.5, 128.6, 128.6, 128.7, 129.1, 129.1, 130.4, 131.3, 131.4, 133.6, 133.6, 133.8, 134.0, 134.0, 134.0, 136.7, 136.8, 137.4, 137.5, 137.9, 138.0, 140.9, 141.9, 142.2, 152.7, 153.0.

$^{31}$P-NMR (121 MHz, CDCl$_3$) δ −11.74.

FTIR (KBr, cm$^{-1}$): 3354 (m), 3052 (m), 2954 (m), 2868 (w), 1581 (w), 1505 (s), 1435 (m), 1392 (m), 911 (s), 739 (s).

MS (HiResMALDI, pos.) calcd for C$_{42}$H$_{39}$N$_3$O$_2$P$^+$ (M+H$^+$) 632.2825, found 632.2830.

Example 14

Trifluoromethanesulfonic acid 1-(4-chlorophthalazin-1-yl)-7-methoxynaphthalen-2-yl ester To a suspension of 1-(4-chlorophthalazin-1-yl)-7-methoxynaphthalen-2-ol (5.5 g, 16 mmol) and pyridine (4.2 ml, 54 mmol) in dichloromethane (500 ml) was added dropwise trifluoromethanesulfonic anhydride (3.2 ml, 19 mmol) over 40 min and the resulting mixture was stirred at 0° C. for 1 hr. The resulting solution was quenched with sat. aqueous ammonium chloride solution. The organic layer was separated and the aqueous layer was extracted twice with dichloromethane. The combined organic layers were dried over sodium sulfate and concentrated under reduced pressure. The resulting grey solid was dissolved in dichloromethane and passed through a short plug of silica gel. The filtrate was concentrated under reduced pressure. The residue was triturated with pentane to give 6.3 g (14 mmol) of the title compound as a grey powder.

mp: 140° C.

$^1$H-NMR (300 MHz, CDCl$_3$) δ 3.54 (s, 3H), 6.50 (s, 1H), 7.22 (dd, J=9.0, J=1.5), 7.45 (d, J=8.4, 1H), 7.47 (d, J=8.4, 1H), 7.81-7.90 (m, 2H), 8.00-8.06 (m, 2H), 8.43 (d, J=8.1, 1H).

$^{13}$C-NMR (100 MHz, CDCl$_3$) δ 55.3, 104.3, 116.7, 117.9 (q, J$_{CF}$=315), 123.6, 125.5, 125.8, 126.2, 127.9, 128.2, 129.9, 131.9, 133.8, 134.0, 134.3, 145.8, 155.2, 155.5, 159.3.

FTIR (thin film, cm$^{-1}$): 3072 (w), 3008 (w), 2941 (w), 2835 (w) 1625 (s), 1508 (s), 1468 (s), 1422 (s), 1378 (s), 1344 (m), 1290 (s), 1229 (s), 1139 (s), 989 (s), 870 (s).

HRMS (ESI, pos.) calcd for C$_{20}$H$_{12}$N$_2$O$_2$F$_3$SCl (M+H)$^+$ 469.02. found 469.02.

Anal. Calcd for C$_{20}$H$_{12}$N$_2$O$_2$F$_3$SCl: C, 51.24; H, 2.58. Found: C, 25 51.47; H, 2.73.

Example 15

Trifluoromethanesulfonic acid 7-methoxy-1-[4-((R)-1-phenylethylamino)-phthalazin-1-yl]naphthalen-2-yl ester A solution of trifluoromethanesulfonic acid 1-(4-chlorophthalazin-1-yl)-7-methoxynaphthalen-2-yl ester (2.2 g, 4.7 mmol) in (R)-1-phenylethylamine (3.5 ml, 27 mmol) was stirred for 8 hrs at 130° C., then cooled to 23° C. The resulting viscous mixture was purified by flash chromatography on silica gel (toluene/EtOAc 5:1 to 3:1) to give 2.1 g (3.8 mmol) of the title compound as a 1:1 mixture of diastereomers as a light brown foam.

HRMS (MALDI, pos.) calcd for C$_{28}$H$_{22}$F$_3$N$_3$O$_4$S (M+H) 554.13. found 554.13.

Example 16

[4-(2-Diphenylphosphanyl-7-methoxy-naphthalen-1-yl)-phthalazin-1-yl]-((R)-1-phenylethyl)-amine A solution of NiCl$_2$(dppe) (0.22 g, 0.42 mmol) in N,N-dimethylformamide (10 ml) was treated with diphenylphosphine (1.5 ml, 8.4 mmol) at 23° C. The resulting dark red solution was stirred at 120° C. for 30 min. Then a solution of trifluoromethanesulfonic acid 7-methoxy-1-[4-((R)-1-phenyl-ethylamino)-phthalazin-1-yl]-naphthalen-2-yl ester (2.3 g, 4.2 mmol) and 1,4-diazabicyclo[2.2.2]octane (DABCO, 1.9 g, 17 mmol) in N,N-dimethylformamide (13 ml) was added via a syringe, the flask was washed with N,N-dimethylformamide (2 ml). The resulting green solution was stirred at 120° C. for 17 hrs. The mixture was concentrated under reduced pressure (20 mbar, 70° C. bath temperature). The residue was purified by flash chromatography on silica gel (toluene→toluene/EtOAc 5:1) to give 1.5 g (2.5 mmol) of the title compound as an off-white solid as a 1.7:1 (1$^{st}$ diastereomer: 2$^{nd}$ diastereomer) mixture of diastereomers.

Separation of the diastereomers was performed by flash chromatography on silica gel (toluene→toluene/EtOAc 4:1)

(1$^{st}$ Diastereomer)

[α]$_D^{28}$=−171.8 (c=0.50, CHCl$_3$)

HRMS (MALDI, pos.) calcd for C$_{39}$H$_{32}$N$_3$OP (M+H) 589.23. found 589.23.

(2$^{nd}$ Diastereomer)

[α]$_D^{28}$=65.3 (c=0.50, CHCl$_3$)

HRMS (MALDI, pos.) calcd for C$_{39}$H$_{32}$N$_3$OP (M+H) 589.23. found 589.23.

Example 17

Trifluoromethanesulfonic acid 1-[4-((R)-2-ethyl-2-hydroxy-1-phenylbutylamino)-phthalazin-1-yl]-7-methoxynaphthalen-2-yl ester To trifluoromethanesulfonic acid 1-(4-chlorophthalazin-1-yl)-7-methoxynaphthalen-2-yl ester (5.0 g, 11 mmol) was added 3-((R)-α-amino-benzyl)-pentan-3-ol (10 g, 52 mmol). The suspension was stirred for 18 hrs at 120° C. After cooling to 25° C., the mixture was filtered following addition of dichloromethane. The filtrate was concentrated under reduced pressure. The residue was purified by flash chromatography on silica gel (toluene/EtOAc 10:1 to 5:1) to give the title compound as a brown solid, which was triturated from hexane/diethyl ether to give 4.8 g (7.7 mmol) of a pure product as a mixture of diastereomers.

mp: 175-177° C.

$^1$H-NMR (400 MHz, CDCl$_3$) δ 0.88-1.02 (m, 12H), 1.21-1.40 (m, 2H), 1.41-1.49 (m, 2H), 1.72-1.97 (m, 4H), 3.41 (s, 3H), 3.60 (s, 3H), 5.71 (d, J=8.7, 1H), 5.87 (d, J=8.8, 1H), 6.52-6.58 (m, 3H), 6.74 (d, J=2.4, 1H), 7.14-7.42 (m, 12H), 7.54-7.64 (m, 6H), 7.76-7.85 (m, 4H), 7.93-8.00 (m, 4H).

$^{13}$C-NMR (125 MHz, CDCl$_3$) δ 7.5, 7.6, 8.2, 8.3, 27.7, 27.7, 28.9, 28.9, 55.2, 55.2, 58.6, 59.4, 77.8, 78.2, 105.0, 105.2, 117.8 (q, J=319), 117.0, 117.1, 117.8, 118.0, 118.2 (q, J$_{CF}$=318) 119.7, 119.9, 120.5, 125.4, 125.9, 126.1, 126.2, 127.3, 127.3, 128.0, 128.1, 128.2, 128.5, 128.9, 129.7, 129.7, 130.7, 130.8, 131.4, 131.4, 131.4, 135.1, 135.2, 140.0, 140.4, 146.1, 146.2, 146.3, 152.8, 152.9, 158.9, 159.0.

FTIR (thin film, cm$^{-1}$): 2996 (w), 1625 (w), 1579 (w), 1544 (w), 1508 (s), 1420 (m), 1219 (s), 1139 (m), 772 (s).

HRMS (MALDI, pos.) calcd for C$_{32}$H$_{30}$N$_3$O$_5$F$_3$S (M+H) 626.19. found 626.19.

Anal. Calcd for C$_{32}$H$_{30}$N$_3$O$_5$F$_3$S: C, 61.43; H, 4.83. Found: C, 30 61.53; H, 4.74.

Example 18

(R,M)-3-{[4-(2-Diphenylphosphanyl-7-methoxy-naphthalen-1-yl)-phthalazin-1-ylamino]-phenyl-methyl}-pentan-3-ol (1$^{st}$ diastereomer) and (R,P)-3-{[4-(2-Diphenylphosphanyl-7-methoxy-naphthalen-1-yl)-phthalazin-1-ylamino]-phenyl-methyl}-pentan-3-ol (2$^{nd}$ diastereomer)

A solution of NiCl$_2$(dppe) (0.61 g, 1.2 mmol) in N,N-dimethylformamide (30 ml) was treated with diphenylphosphine (4.0 ml, 23 mmol) at 23° C. The resulting dark red solution was stirred at 120° C. for 30 min. Then a solution of trifluoromethanesulfonic acid 1-[4-((R)-2-ethyl-2-hydroxy-1-phenyl-butylamino)-phthalazin-1-yl]-7-methoxy-naphthalen-2-yl ester (7.3 g, 12 mmol) and 1,4-diazabicyclo[2.2.2]octane (DABCO, 5.2 g, 46 mmol) in N,N-dimethylformamide (65 ml) was added via a syringe, and the flask was washed with N,N-dimethylformamide (5 ml). The resulting green solution was stirred at 120° C. for 12 hrs. The mixture was concentrated under reduced pressure (20 mbar, 70° C. bath temperature). The residue was purified by flash chromatography on silica gel (toluene→toluene/EtOAc 4:1) to give 5.2 g (7.8 mmol) of the title compounds as an off-white solid as a 1.7:1 (1$^{st}$ diastereomer: 2$^{nd}$ diastereomer) mixture of diastereomers.

Separation of the diastereomers was performed by flash chromatography on silica gel (toluene→toluene/EtOAc 4:1).

($1^{st}$ Diastereomer)

mp: 180° C.

$[\alpha]_D^{28}$=151.7 (c=0.50, CHCl$_3$).

$^1$H-NMR (400 MHz, CDCl$_3$) δ 0.87 (t, J=5.9, 3H), 0.97 (t, J=6.0, 3H), 1.21-1.26 (m, 1H), 1.39-1.47 (m, 1H), 1.79-1.93 (m, 2H), 3.30 (s, 3H), 5.63 (d, J=6.8, 1H), 6.31 (d, J=1.8, 1H). 6.54 (d, J=6.7, 1H), 7.08-7.42 (m, 11H), 7.46 (app t, J=5.8, 1H), 7.58 (d, J=5.7, 2H), 7.71 (app t, J=6.2, 1H), 7.79 (dd, J=11.2, 7.2, 2H), 8.00 (d, J=6.6, 1H).

$^{13}$C-NMR (125 MHz, CDCl$_3$) δ 7.8, 8.61, 28.1, 29.2, 55.4, 59.4, 78.1, 105.4, 105.4, 118.3, 119.7, 120.9, 126.8, 127.5, 128.2, 128.4, 128.5, 128.6, 128.6, 128.6, 128.7, 128.7, 129.2, 129.5, 129.8, 131.2, 131.4, 133.7, 133.8, 133.9, 134.0, 134.7, 134.7, 137.0, 137.1, 137.6, 137.7, 138.2, 138.3, 140.5, 140.8, 141.1, 152.6, 152.7, 153.0, 158.5.

FTIR (KBr, cm$^{-1}$): 3337 (s), 3048 (m), 2963 (m), 2936 (m), 2878 (m), 1619 (s), 1579 (s), 1552 (s), 1504 (s), 1405 (s), 1370 (s), 1225 (s), 1141 (m), 1028 (s), 838 (s), 696 (s).

HRMS (MALDI, pos.) calcd for C$_{43}$H$_{40}$N$_3$O$_2$P (M+H) 662.29. found 662.29.

Anal. Calcd for C$_{43}$H$_{40}$N$_3$O$_2$P : C, 78.04; H, 6.09. Found: C, 78.11; H, 6.02.

($2^{nd}$ Diastereomer)

mp: 143-145° C.

$[\alpha]_D^{29}$=−41.5(c=0.50, CHCl$_3$).

$^1$H-NMR (400 MHz, CDCl$_3$) δ 0.85-0.96 (m, 6H), 1.23-1.30 (m, 1H) 1.41-1.45 (m, 1H), 1.78-1.82 (m, 1H), 1.87-1.92 (m, 1H), 3.50 (s, 3H), 5.68 (s, 1H), 6.49 (d, J=1.9, 1H), 6.99-7.42 (m, 19H), 7.62-7.67 (m, 3H), 7.80-7.82 (m, 2H), 8.08 (s, 1H).

$^{13}$C-NMR (125 MHz, CDCl$_3$) δ 7.8, 8.5, 28.1, 29.0, 55.4, 59.5, 78.0, 105.6, 119.4, 126.8, 127.6, 127.7, 128.1, 128.2, 128.3, 128.3, 128.4, 128.4, 128.5, 128.5, 128.6, 128.6, 128.7, 129.2, 129.4, 129.9, 130.0, 131.2, 131.3, 131.4, 133.8, 133.8, 133.9, 134.0, 134.7, 134.7, 137.4, 137.4, 137.5, 137.8, 137.9, 140.8, 152.5, 152.9, 158.5.

FTIR (KBr, cm$^{-1}$): 3389 (m), 3053 (m), 2961 (s), 2877 (m), 1619 (s), 1579 (m), 1504 (s), 1432 (s), 1262 (m), 1224 (s),-1092 (m), 1028 (m), 838 (s), 695 (s).

HRMS (MALDI, pos.) calcd for C$_{43}$H$_{40}$N$_3$O$_2$P (M+H) 662.29. found 662.29.

Example 19

(S,M)-3-{[4-(2-Diphenylphosphanyl-7-methoxy-naphthalen-1-yl)-phthalazin-1-ylaminol]-phenyl-methyl}-pentan-3-ol In the same manner as in Examples 17 and 18 except that 3-((S)-α-amino-benzyl)-pentan-3-ol was used instead of 3-((R)-α-amino-benzyl)-pentan-3-ol, the title compound was obtained.

mp: 180° C.

$[\alpha]_D^{25}$=−160.0 (c=0.50, CHCl$_3$)

$^1$H-NMR (400 MHz, CDCl$_3$) δ 0.87 (t, J=5.9, 3H), 0.97 (t, J=6.0, 3H), 1.21-1.26 (m, 1H), 1.39-1.47 (m, 1H), 1.79-1.93 (m, 2H), 3.30 (s, 3H), 5.63 (d, J=6.8, 1H), 6.31 (d, J=1.8, 1H) 6.54 (d, J=6.7, 1H), 7.08-7.42 (m, 11H), 7.46 (app t, J=5.8, 1H), 7.58 (d, J=5.7, 2H), 7.71 (app t, J=6.2, 1H), 7.79 (dd, J=11.2, 7.2, 2H), 8.00 (d, J=6.6, 1H).

$^{13}$C NMR (125 MHz, CDCl$_3$) δ 7.8, 8.61, 28.1, 29.2, 55.4, 59.4, 78.1, 105.4, 105.4, 118.3, 119.7, 120.9, 126.8, 127.5, 128.2, 128.4, 128.5, 128.6, 128.6, 128.6, 128.7, 129.2, 129.5, 129.8, 131.2, 131.4, 133.7, 133.8, 133.9, 134.0, 134.7, 134.7, 137.0, 137.1, 137.6, 137.7, 138.2, 138.3, 140.5, 140.8, 141.1, 152.6, 152.7, 153.0, 158.5.

FTIR (KBr, cm$^{-1}$): 3337 (s), 3048 (m), 2963 (m), 2936 (m), 2878 (m), 1619 (s), 1579 (s), 1552 (s), 1504 (s), 1405 (s), 1370 (s), 1225 (s), 1141 (m), 1028 (s), 838 (s), 696 (s).

HRMS (MALDI, pos.) calcd for C$_{43}$H$_{40}$N$_3$O$_2$P (M+H) 662.29. found 662.29.

Anal. Calcd for C$_{43}$H$_{40}$N$_3$O$_2$P: C, 78.04; H, 6.09. Found: C, 77.78; H, 6.12.

Example 20

N,N-Dibenzyl-2-methyl-5-decyn-4-amine

A 10 ml schlenk tube was charged with copper (I) bromide (3.6 mg, 0.025 mmol), (R,Sax)-[4-(2-diphenylphosphanyl-naphthalen-1-yl)-phthalazin-1-yl]-(1-phenylethyl)-amine (15.4 mg, 0.028 mmol) and 4 Å molecular sieves (0.3 g). The schlenk tube was flushed with argon for 5 min and then toluene (2 ml) was added. The resulting suspension was stirred for 1 hr at 23° C. To the reaction mixture was subsequently added 1-hexyne (41 mg, 0.50 mmol), 3-methylbutanal (43 mg, 0.50 mmol) and dibenzylamine (99 mg, 0.50 mmol). The resulting reaction mixture was stirred at 23° C. for 5 days and purified by flash chromatography on silica gel to give 128 mg of the title compound as a colorless oil.

(yield: 74%, optical purity: 92% ee)

$[\alpha]_D^{32}$=+167 (c=1.09, CHCl$_3$).

PLC conditions: column: Chiralcel OD-H (25 cm, Daicel), mobile phase: 99.5% hexane/0.5% iPrOH, flow rate: 0.1 ml/min, retention time: (minor)=45.3 min, (major)=50.3 min.

Example 21

N,N-Dibenzyl-4-methyl-1-phenyl-1-pentyn-3-amine

In the same manner as in Example 20 except that phenylacetylene (51 mg, 0.50 mmol) was used instead of n-hexyne and 2-methylpropanal (36 mg, 0.50 mmol) was used instead of 3-methylbutanal, 156 mg of the title compound was obtained as a colorless oil. (Yield: 88%, optical purity: 90% ee)

$[\alpha]_D^{26}$=+313 (c=1.06, CHCl$_3$).

HPLC conditions: column: Chiralcel OD-H×2 (25 cm, Daicel), mobile phase: 99.5% hexane/0.5% iPrOH, flow rate: 0.2 ml/min, retention time: (minor)=36.9 min, (major)=41.0 min.

Example 22

N,N-Dibenzyl-4-methyl-1-pentyn-3-amine

In the same manner as in Example 20 except that (trimethylsilyl)acetylene (74 mg, 0.75 mmol) was used instead of n-hexyne, 2-methylpropanal (36 mg, 0.50 mmol) was used instead of 3-methylbutanal and the reaction time was 3 days, 147 mg of N,N-dibenzyl-4-methyl-1-(trimethylsilyl)-1-pentyn-3-amine was obtained as a colorless oil. (Yield: 84%)

$[\alpha]_D^{33}$=+237 (c=0.99, CHCl$_3$).

N,N-Dibenzyl-4-methyl-1-(trimethylsilyl)-1-pentyn-3-amine obtained above (105 mg, 0.300 mmol) was dissolved in tetrahydrofuran (2 ml) and the solution was cooled to 0° C. To the solution was added dropwise tetrabutylammonium fluoride (0.330 ml, 0.330 mmol). After the completion of the reaction, toluene (2 ml) was added, and tetrahydrofuran was evaporated under reduced pressure. The toluene layer was directly subjected to flash chromatography on silica gel to give 77.4 mg of the title compound as a colorless oil. (Yield: 93%, optical purity: 80% ee)

$[\alpha]_D^{35}$=+205 (c=1.07, CHCl$_3$).

HPLC conditions: column: Chiralcel OD-H×2 (25 cm, Daicel), mobile phase: hexane, flow rate: 0.2 ml/min, retention time: (minor)=53.0 min, (major)=60.2 min.

Example 23

1-(1-(Trimethylsilyl)oct-1-yn-3-yl)piperidin-4-one

A 10 ml schlenk tube was charged with copper (I) bromide (3.6 mg, 0.025 mmol), (R,Rax)-[4-(2-diphenylphosphanyl-naphthalen-1-yl)-phthalazin-1-yl]-(1-phenylethyl)amine (15.7 mg, 0.028 mmol) and 4 Å molecular sieves (powdered, 0.25 g) and then purged with argon for 5 min. Dichloromethane (1 ml) was added and the resulting suspension was stirred for 60 min. To the reaction mixture were added triethylamine (56 mg, 0.55 mmol), 4-piperidone monohydrochloride monohydrate (powder, 154 mg, 1.0 mmol), (trimethylsilyl)acetylene (98 mg, 1.00 mmol) and n-hexanal (50 mg, 0.50 mmol). The flask was rinsed with an additional 1 ml of dichloromethane and then sealed. The reaction mixture was stirred vigorously at 23° C. for 22 hrs. The reaction mixture was directly purified by flash chromatography on silica gel (hexane/EtOAc=9:1) to give 102 mg of the title compound as a colorless oil. (Yield: 73%)

$[\alpha]_D^{25}$: −11.0°

$^1$H-NMR (300 MHz, CDCl$_3$) δ 0.13 (s, 9H, TMS), 0.89 (t, J=6.9, 3H), 1.28-1.34 (m, 4H), 1.43-1.48 (m, 2H), 1.63 (q, J=7.5, 2H), 2.42-2.48 (m, 4H), 2.64-2.72 (m, 2H), 2.84-2.93 (m, 2H), 3.42 (t, J=7.5, 1H).

$^{13}$C-NMR (75 MHz, CDCl$_3$) δ 0.3, 14.1, 22.6, 26.2, 31.5, 33.6, 41.5, 49.1, 57.4, 90.0, 103.0, 209.0.

FTIR (thin film, cm$^{-1}$): 2957 (s), 2860 (m), 2160 (m), 1723 (s) 1469 (w), 1337 (m), 1250 (s), 843 (s).

MS (EI) calcd for C$_{16}$H$_{29}$NOSi [M−H]$^+$ 278.1935 found 278.1936.

The title compound was treated with potassium carbonate in methanol at 23° C. for 4 hrs to give a desilylation form, which was then subjected to chiral analysis by gas chromatography (Gamma 1, 115° C., retention time: (minor)=70.472 min, (major)=71.593 min). Optical purity was 90% ee.

$[\alpha]_D^{25}$: −18.0° (desilylation form)

Example 24

1-(4-Methyl-1-(trimethylsilyl)pent-1-yn-3-yl)piperidin-4-one

In the same manner as in Example 23 except that isobutanal (108 mg, 1.50 mmol) was used instead of n-hexanal, 111 mg of the title compound was obtained as a colorless oil.

(Yield: 88%)

$[\alpha]_D^{23}$: −25.1°

$^1$H-NMR (300 MHz, CDCl$_3$) δ 0.15 (s, 9H, TMS), 1.03 (dd, J$_1$=6.5, J$_2$=16.2, 6H), 1.73-1.83 (m, 1H), 2.42-2.53 (m, 4H), 2.61-2.69 (m, 2H), 2.82-2.90 (m, 2H), 2.95 (d, J=10.3, 1H).

$^{13}$C-NMR (75 MHz, CDCl$_3$) δ 0.3, 19.8, 20.6, 30.9, 41.6, 49.3, 64.6, 90.5, 102.4, 209.3.

FTIR (thin film, cm$^{-1}$): 2959 (s), 2905(m), 2815 (m), 2160 (m), 1720 (s), 1467 (w), 1249 (m), 1212 (m), 1075 (m), 1008 (m), 843 (s), 760 (m).

MS (EI) calcd for C$_{14}$H$_{25}$NOSi [M−H]$^+$ 250.1622 found 250.1621.

The title compound was treated with potassium carbonate in methanol at 23° C. for 4 hrs to give a desilylation form, which was then subjected to chiral analysis by gas chromatography (Gamma 1, 120° C., retention time: (minor)=15.837 min, (major)=16.211 min). Optical purity was 96% ee.

$[\alpha]_D^{25}$: −37.9° (desilylation form)

Example 25

1-(1-(Furan-2-yl)-3-(trimethylsilyl)prop-2-ynyl)piperidin-4-one

In the same manner as in Example 23 except that furfural (48 mg, 0.50 mmol) was used instead of n-hexanal, 81 mg of the title compound was obtained as a white solid. (Yield: 58%)

$[\alpha]_D^{26}$: 2.5°

$^1$H-NMR (300 MHz, CDCl$_3$) δ 0.17 (s, 9H, TMS), 2.38-2.54 (m, 4H), 2.73-2.82 (m, 4H), 4.8 (s, 1H), 6.31-6.32 (m, 1H), 6.41 (d, J=3.43, 1H), 7.38-7.39 (m, 1H).

$^{13}$C-NMR (75 MHz, CDCl$_3$) δ 0.1, 41.3, 49.0, 55.5, 91.9, 98.1, 109.6, 110.0, 142.8, 150.7, 208.4.

FTIR (thin film, cm$^{-1}$): 3117 (w), 2959 (s), 2903 (m), 2817 (s), 2168 (m), 1718 (s), 1501 (w), 1330 (m), 1250 (s), 1204 (s), 1070 (m), 995 (s), 844 (s).

MS (EI) calcd for C$_{15}$H$_{21}$NO$_2$Si [M−H]$^+$ 274.1258 found 274.1258.

The title compound was subjected to chiral analysis by gas chromatography (Gamma 1, 135° C., retention time: (minor)= 97.006 min, (major)=98.568 min). Optical purity was 90% ee.

Example 26

1-(4-Methyl-1-phenylpent-1-yn-3-yl)piperidin-4-one

In the same manner as in Example 23 except that isobutanal (108 mg, 1.50 mmol) was used instead of n-hexanal and phenylacetylene (51 mg, 0.05 mmol) was used instead of (trimethylsilyl)acetylene, 105 mg of the title compound was obtained as a white solid. (Yield: 82%, optical purity: 85% ee)

HPLC conditions:

column: Chiralcel OD-H (25 cm×4.6 mm, Daicel) and Chiralcel OD-H (15 cm×4.6 mm, Daicel), mobile phase: 98.5% hexane/1.5% iPrOH, flow rate: 0.25 ml/min, detector: 254 nm, retention time: (major)=53.65 min, (minor)=60.95 min.

$^1$H-NMR (300 MHz, CDCl$_3$) δ 1.11 (dd, J$_1$=6.5, J$_2$=20.2, 6H), 1.86-1.99 (m, 1H), 2.41-2.56 (m, 4H), 2.73-2.79 (m, 2H), 2.81-3.03 (m, 2H), 3.19 (d, J=10.0, 1H), 7.26-7.43 (m, 5H).

$^{13}$C-NMR (75 MHz, CDCl$_3$) δ 20.0, 20.8, 41.7, 49.5, 64.4, 86.2, 86.5, 123.0, 127.9, 128.2, 131.5, 209.2.

FTIR (thin film, cm$^{-1}$): 3055 (w), 2960 (s), 2908 (m), 2869 (w), 2813 (m), 2360 (w), 1717 (s), 1680 (w), 1598 (w), 1489 (m), 1334 (m), 1212 (s), 1074 (m), 757 (s).

MS (EI) calcd for C$_{17}$H$_{21}$NO [M−H]$^+$ 254.1539 found 254.1541.

Example 27

4-Methyl-1-phenylpent-1-yn-3-amine

A 25 ml pressure tube was charged with 1-(4-methyl-1-phenylpent-1-yn-3-yl)piperidin-4-one (76.6 mg, 0.30 mmol) and ammonium chloride (48 mg, 0.90 mmol). The pressure tube was purged with argon for 5 min and then saturated ethanolic ammonia solution (2 ml) was added. The pressure tube was sealed tightly and the reaction mixture was stirred at 90° C. for 4 hrs. The reaction mixture was concentrated under reduced pressure and the brown residue was subjected to flash chromatography on silica gel (EtOAc/MeOH=19:1) to give 33.3 mg of a pure title compound as a yellowish oil. (yield: 64%)

$^1$H-NMR (300 MHz, CDCl$_3$) δ 1.06 (d, J=6.7, 6H), 1.81-1.92 (m, 1H), 3.62 (d, J=5.4, 1H), 7.26-7.43 (m, 5H).

Example 28

Preparation of Rh-complex

In a 10 ml schlenk flask, dichloromethane (5 ml) degassed with argon was added to a mixture of [Rh(cod)$_2$]BF$_4$ (41 mg, 0.1 mmol) and (R,Sax)-1-(2-diphenylphosphanylnaphthalen-1-yl)-4-(1-phenyl-ethoxy)-phthalazine (59 mg, 0.105 mmol). The mixture was stirred for 20 min, the solvent was then removed in vacuo. The obtained yellow-orange residue was scratched from the wall of the flask with a spatula and triturated with diethyl ether (5 ml) degassed with argon. The diethyl ether was removed via cannula and the yellow-orange residue dried in vacuo to give Rh-complex. The complex was not air stable and was stored in a glove box with exclusion of oxygen and moisture at 25° C.

Example 29

(S)-1—Phenylethanol

A solution of rhodium-complex (3.4 mg, 4 μmol) obtained in Example 28 in dichloromethane degassed with argon was transferred with a syringe to the reaction vessel. Dichloromethane was evaporated in vacuo, then dry toluene (1 ml) degassed with argon, styrene (41.7 mg, 0.4 mmol) and freshly distilled catecholborane (56 μl, 0.45 mmol) were added. The reaction mixture was stirred at room temperature for 2 hrs, cooled with ice-bath, and quenched with EtOH (1 ml). 2M aqueous sodium hydroxide solution (1 ml) and 30% aqueous hydrogen peroxide (1 ml) were added. The mixture was allowed to warm up to room temperature over 30 min and then stirred for 2 hrs at this temperature. Diethyl ether (10 ml) was added to the mixture, and the orange organic layer was then washed with 1M aqueous sodium hydoxide solution and then dried over sodium sulfate. After evaporation of the solvent, the product was purified by chromatography on silica gel (pentane/diethyl ether 2:1) to give 35.7 mg of the title compound. (Yield: 73%, optical purity: 92% ee)

$[α]_D^{29}$=−49.5 (c=0.525, CHCl$_3$).

HPLC conditions: column: Chiralcel OD-H (25 cm, Daicel), mobile phase: 99% hexane/1% iPrOH, flow rate: 0.9 ml/min, retention time: R-enantiomer=24.5 min, S-enantiomer=32.5 min.

Example 30

(S)-1-(4-Methylphenyl)ethanol

In the same manner as in Example 29 except that 4-methylstyrene (47.3 mg, 0.40 mmol) was used instead of styrene, 51.2 mg of the title compound was obtained. (Yield: 94%, optical purity: 92% ee)

Ratio 1-(4-methylphenyl)ethanol/2-(4-methylphenyl)ethanol was 98:2 as judged by $^1$H-NMR $[α]_D^{27}$=−53.0 (c=0.55, CHCl$_3$).

HPLC conditions: column: Chiralcel OD-H (25 cm, Daicel), mobile phase: 99.5% hexane/0.5% iPrOH, flow rate: 0.9 ml/min, retention time: R-enantiomer=39.8 min, S-enantiomer=42.6 min.

Example 31

(S)-1-(3-Methylphenyl)ethanol

In the same manner as in Example 29 except that 3-methylstyrene (47.3 mg, 0.40 mmol) was used instead of styrene, 46.4 mg of the title compound was obtained. (Yield: 85%, optical purity: 84% ee)

Ratio 1-(3-methylphenyl)ethanol/2-(3-methylphenyl)ethanol was 92:8 as judged by $^1$H-NMR.

$[α]_D^{26}$=−42.6 (c=0.62, CHCl$_3$).

HPLC conditions: column: Chiralcel OD-H (25 cm, Daicel), mobile phase: 99% hexane/1% iPrOH, flow rate: 0.8 ml/min, retention time: R-enantiomer=20.1 min, S-enantiomer=28.6 min.

Example 32

(S)-1-(2-Methylphenyl)ethanol

In the same manner as in Example 29 except that 2-methylstyrene (47.3 mg, 0.40 mmol) was used instead of styrene, 44.2 mg of the title compound was obtained. (Yield: 81%, optical purity: 91% ee)

Ratio 1-(2-methylphenyl)ethanol/2-(2-methylphenyl)ethanol was 91:9 as judged by $^1$H-NMR.

$[α]_D^{29}$=−72.1 (c=0.535, CHCl$_3$).

HPLC conditions: column: Chiralcel OB-H (25 cm, Daicel), mobile phase: 90% hexane/10% iPrOH, flow rate: 0.5 ml/min, retention time: S-enantiomer=10.0 min, R-enantiomer=13.7 min.

Example 33

(S)-1-(4-Methoxyphenyl)ethanol

In the same manner as in Example 29 except that 4-methoxystyrene (53.7 mg, 0.40 mmol) was used instead of styrene and the reaction time before oxidative workup was 3 hrs, 48.5 mg of the title compound was obtained. (Yield: 80%, optical purity: 90% ee)

Ratio 1-(4-methoxyphenyl)ethanol/2-(3-methoxyphenyl)ethanol was 95:5 as judged by $^1$H-NMR.

$[α]_D^{28}$=−45.5 (c=0.545, CHCl$_3$).

HPLC conditions: column: Chiralcel OD-H (25 cm, Daicel), mobile phase: 99% hexane/1% iPrOH, flow rate: 0.9 ml/min, retention time: R-enantiomer=40.0 min, S-enantiomer=45.6 min.

Example 34

(S)-1-(4-Chlorophenyl)ethanol

In the same manner as in Example 29 except that 4-chlorostyrene (55.4 mg, 0.40 mmol) was used instead of styrene and the reaction time before oxidative workup was 3 hrs, 54.2 mg of the title compound was obtained. (Yield: 87%, optical purity: 87% ee)

Ratio 1-(4-chlorophenyl)ethanol/2-(4-chlorophenyl)ethanol was 98:2 as judged by $^1$H-NMR.

$[α]_D^{27}$=−42.4 (c=0.495, CHCl$_3$).

HPLC conditions: column: Chiralcel OD-H (25 cm, Daicel), mobile phase: 99% hexane/1% iPrOH, flow rate: 0.9 ml/min, retention time: S-enantiomer=24.8 min, R-enantiomer=27.6 min.

Example 35

(S)-1-(2-Naphthyl)ethanol

In the same manner as in Example 29 except that 2-vinylnaphthalene (61.7 mg, 0.40 mmol) was used instead of styrene and the reaction time before oxidative workup was 4 hrs, 56.9 mg of the title compound was obtained. (Yield: 80%, optical purity: 81% ee)

Ratio 1-(2-naphthyl)ethanol/2-(2-naphthyl)ethanol was 86:14 as judged by $^1$H-NMR.

$[\alpha]_D^{29}$=−31.7 (c=0.51, CHCl$_3$).

HPLC conditions: column: Chiralcel OB-H (25 cm, Daicel), mobile phase: 90% hexane/10% iPrOH, flow rate: 0.5 ml/min, retention time: S-enantiomer=17.9 min, R-enantiomer=20.7 min.

Example 36

(R)-(+)-5-(1-Isopropyl-3-phenylprop-2-ynyl)-2,2-dimethyl-1,3-dioxane-4,6-dione

A solution of copper (II) acetate monohydrate (5.0 mg, 0.025 mmol) in water (0.2 ml) was treated with sodium (L)-ascorbate (10 mg, 0.050 mmol), the mixture was stirred until the mixture was turned bright orange (3 min). Subsequently, (R,M)-3-{[4-(2-diphenylphosphanyl-7-methoxy-naphthalen-1-yl)-phthalazin-1-ylamino]-phenyl-methyl}-pentan-3-ol (1st diastereomer, 16.5 mg, 0.025 mmol) and phenylacetylene (0.275 ml, 2.5 mmol) were added, the resulting mixture was stirred for 10 min at 23° C., cooled to 0° C., stirred for 5 min and treated with 5-isobutylidene-2,2-dimethyl-1,3-dioxane-4,6-dione (50 mg, 0.25 mmol). The reaction mixture was stirred vigorously at 0° C. for 14 hrs, diluted with dichloromethane (2 ml) and subjected directly to flash chromatography on silica gel (hexane/EtOAc 3:1) to give 71 mg of the pure title compound as a white solid. (yield: 94%)

mp: 111-113° C.

$[\alpha]_D^{25}$=7.93 (c=0.5, CHCl$_3$).

The other spectroscopic data was in agreement with the data reported in the literature (J. Am. Chem. Soc., 2003, 125, 6054-6055)

The title compound was treated with aniline in N,N-dimethylformamide for 1 hr at 100° C. to give (R)-3-isopropyl-5-phenyl-4-pentynanilide, which was subjected to a chiral analysis with HPCL. The optical purity was 95% ee.

HPLC conditions:
column: Chiralcel OD-H (25 cm×4.6 mm, Daicel) and Chiralcel OD-H (15 cm×4.6 mm, Daicel), mobile phase: 87% hexane/13% iPrOH, flow rate: 0.7 ml/min, detector: 254 nm, retention time: (minor)=25.4 min, (major)=27.5 min.

The absolute configuration was determined by converting the title compound into (S)-3-isopropyl-5-phenylpentanoic acid (1. H$_2$O, DMF, 100° C.; 2. H$_2$, PtO$_2$, EtOAc), which was compared with the reported literature (J. Org. Chem. 2002, 67, 4680-4683).

Example 37

(R)-(+)-5-(1-Cyclohexyl-3-phenylprop-2-ynyl)-2,2-dimethyl-1,3-dioxane-4,6-dione

A solution of copper (II) acetate monohydrate (5.0 mg, 0.025 mmol) in water (0.2 ml) was treated with sodium (L)-ascorbate (10 mg, 0.050 mmol), the mixture was stirred until the mixture was turned bright orange (3 min). Subsequently, (R,M)-3-{[4-(2-diphenylphosphanyl-7-methoxy-naphthalen-1-yl)-phthalazin-1-ylaminol]-phenyl-methyl}-pentan-3-ol (1st diastereomer, 16.5 mg, 0.025 mmol) and phenylacetylene (0.275 ml, 2.5 mmol) were added, the resulting mixture was stirred for 10 min at 23° C., cooled to 0° C., stirred for 5 min and treated with 5-(cyclohexylmethylene)-2,2-dimethyl-1,3-dioxane-4,6-dione (59 mg, 0.25 mmol). The reaction mixture was-stirred vigorously at 0° C. for 13 hrs, diluted with dichloromethane (2 ml) and subjected directly to flash chromatography on silica gel (hexane/EtOAc 3:1) to give 69 mg of the pure title compound as a white solid. (yield: 81%)

mp: 136-138° C.

$[\alpha]_D^{31}$=8.93 (c=0.50, CHCl$_3$).

$^1$H-NMR (300 MHz, CDCl$_3$) δ 0.98-1.40 (m, 5H), 1.55-1.81 (m, 10H), 2.11-2.24 (m. 1H), 2.32 (d, J=12.6, 1H), 3.34 (dd, J=2.7, 10.2, 1H), 3.78 (d, J=2.7, 1H), 7.26-7.28 (m, 3H), 7.36-7.39 (m, 2H).

$^{13}$C-NMR (75 MHz, CDCl$_3$) δ 26.0, 26.0, 26.2, 28.0, 28.6, 30.8, 32.4, 38.9, 39.4, 46.8, 84.3, 87.7, 105.2, 122.8, 128.0, 128.0, 131.6, 163.6, 165.5.

FTIR (thin film, cm$^{-1}$): 3063 (w), 3000 (w), 2932 (m), 2848 (m) 1790 (m), 1750 (s), 1394 (m), 1384 (m), 1314 (m), 1207 (m), 1059 (m).

MS (ESI, pos.) calcd for C$_{21}$H$_{24}$NaO$_4^+$ (M+Na$^+$) 363.16 found 363.45.

Anal. Calcd for C$_{21}$H$_{24}$O$_4$: C, 74.09; H, 7.11. Found: C, 73.85; H, 7.13.

The-title compound was treated with aniline in N,N-dimethylformamide for 1 hr at 1000° C. to give (R)-3-cyclohexyl-5-phenyl-4-pentynanilide, which was subjected to a chiral analysis with HPLC. The optical purity was 94% ee.

HPLC conditions:
column: Chiralcel OD-H (25 cm×4.6 mm, Daicel) and Chiralcel OD-H (15 cm×4.6 mm, Daicel), mobile phase: 87% hexane/13% iPrOH, flow rate: 0.7 ml/min, detector: 254 nm, retention time: (major)=25.4 min, (minor)=30.4 min.

The absolute configuration was determined by converting the title compound into (S)-3-cyclohexyl-5-phenylpent-4-ynoic acid (4-bromophenyl)amide (DMF/4-bromoaniline 10:1, 1 hr, 100° C.), which was compared with the known compound (Cambridge Crystallographic Data Centre, No. 268029).

Example 38

(R)-(+)-5-(1-Cyclopropyl-3-phenylprop-2-ynyl)-2,2-dimethyl-1,3-dioxane-4,6-dione A solution of copper (II) acetate monohydrate (5.0 mg, 0.025 mmol) in water (0.2 ml) was treated with sodium (L)-ascorbate (10 mg, 0.050 mmol), the mixture was stirred until the mixture was turned bright orange (3 min). Subsequently, (R,M)-3-{[4-(2-diphenylphosphanyl-7-methoxy-naphthalen-1-yl)-phthalazin-1-ylamino]-phenyl-methyl}-pentan-3-ol (1st diastereomer, 16.5 mg, 0.025 mmol) and phenylacetylene (0.275 ml, 2.5 mmol) were added, the resulting mixture was stirred for 10 min at 23° C., cooled to 0° C., stirred for 5 min and treated with 5-(cyclopropylmethylene)-2,2-dimethyl-1,3-dioxane-4,6-dione (49 mg, 0.25 mmol). The reaction mixture was stirred vigorously at 0° C. for 51 hrs, diluted with dichloromethane (2 ml) and subjected directly to flash chromatography on silica gel (hexane/dichloromethane 1:3) to give 59 mg of the pure title compound as a white solid. (yield: 79%)

mp: 96-97° C.

$[\alpha]_D^{25}$=105.4 (c=0.505, CHCl$_3$).

$^1$H-NMR (300 MHz, CDCl$_3$) δ 0.30-0.37 (m, 1H), 0.51-0.65 (m, 2H), 0.70-0.79 (m, 1H), 1.66-1.76 (m, 1H), 1.80 (s, 6H), 2.98 (dd, J=2.6, 9.5, 1H), 3.76 (d, J=2.6, 1H), 7.25-7.29 (m, 3H), 7.37-7.42 (m, 2H).

$^{13}$C-NMR (75 MHz, CDCl$_3$) δ 4.9, 6.3, 14.7, 27.8, 28.5, 37.7, 50.7, 83.4, 86.9, 105.2, 122.7, 128.0, 131.7, 163.6, 164.5.

FTIR (thin film, cm$^{-1}$): 3003 (w), 2881 (w), 1785 (m), 1749 (s) 1490 (w), 1334 (m), 1298 (s), 1204 (m), 1005 (m), 758 (m), 693 (m).

MS (ESI, neg.) calcd for C$_{18}$H$_{17}$O$_4^-$ (M–H$^+$) 297.1 found 297.2.

Anal. Calcd for C18H$_{18}$O$_4$: C, 72.47; H, 6.08. Found: C, 72.34; H, 6.11.

The title compound was treated with aniline in N,N-dimethylformamide for 1 hr at 100° C. to give (R)-3-cyclopropyl-5-phenyl-4-pentynanilide, which was subjected to a chiral analysis with HPLC. The optical purity was 97% ee.

HPLC conditions:

column: Chiralpak AD-H (25 cm×4.6 mm, Daicel), mobile phase: 90% hexane/10% iPrOH, flow rate: 0.8 ml/min, detector: 254 nm, retention time: (minor)=14.5 min, (major)=16.5 min.

Example 39

(R)-(+)-5-(1-Isobutyl-3-phenylprop-2-ynyl)-2,2-dimethyl-1,3-dioxane-4,6-dione

A solution of copper (II) acetate monohydrate (10.0 mg, 0.050 mmol) in water (0.2 ml) was treated with sodium (L)-ascorbate (20 mg, 0.10 mmol), the mixture was stirred until the mixture was turned bright orange (3 min). Subsequently, (R,M)-3-{[4-(2-diphenylphosphanyl-7-methoxy-naphthalen-1-yl)-phthalazin-1-ylaminol]-phenyl-methyl}-pentan-3-ol (1st diastereomer, 33.1 mg, 0.050 mmol) and phenylacetylene (0.275 ml, 2.5 mmol) were added, the resulting mixture was stirred for 10 min at 23° C., cooled to 0° C., stirred for 5 min and treated with 5-(1-isopentylidene)-2,2-dimethyl-1,3-dioxane-4,6-dione (53 mg, 0.25 mmol). The reaction mixture was stirred vigorously at 0° C. for 24 hrs, diluted with dichloromethane (2 ml) and subjected directly to flash chromatography on silica gel (hexane/EtOAc 5:1) to give 67 mg of the pure title compound as a white solid. (Yield: 85%)

mp: 100-102° C.

$[\alpha]_D^{27}$=18.1 (c=0.52, CHCl$_3$).

$^1$H-NMR (300 MHz, CDCl$_3$) δ 0.99 (d, J=2.5, 3H), 1.01 (d, J=2.5, 3H), 1.35-1.44 (m, 1H), 1.78 (s, 6H), 1.87-2.00 (m, 1H), 2.10-2.20 (m, 1H), 3.65 (d, J=2.7, 1H), 3.72-3.79 (m, 1H), 7.24-7.30 (m, 3H), 7.35-7.42 (m, 2H).

$^{13}$C-NMR (75 MHz, CDCl$_3$) δ 21.6, 23.3, 26.4, 27.7, 28.6, 30.4, 41.4, 50.3, 83.5, 88.0, 105.2, 122.9, 128.0, 128.1, 131.7, 163.6, 164.3.

FTIR (thin film, cm$^{-1}$): 2956 (m), 1791 (m), 1750 (s), 1384 (m), 1306 (s), 1206 (m), 1060 (m), 1006 (m), 884 (w), 756 (m).

MS (ESI, neg.) calcd for C$_{19}$H$_{21}$O$_4$ (M–H$^+$) 313.15 found 313.3.

Anal. Calcd for C$_{19}$H$_{22}$O$_4$: C, 72.59; H, 7.05. Found: C, 72.52; H, 7.11.

The title compound was treated with aniline in N,N-dimethylformamide for 1 hr at 100° C. to give (R)-3-isobutyl-5-phenyl-4-pentynanilide, which was subjected to a chiral analysis with HPLC. The optical purity was 90% ee.

HPLC conditions:

column: Chiralcel OD-H (25 cm×4.6 mm, Daicel) and Chiralcel OD-H (15 cm×4.6 mm, Daicel), mobile phase: 87% hexane/13% iPrOH, flow rate: 0.7 ml/min, detector: 254 nm, retention time: (minor)=25.0 min, (major)=26.8 min.

Example 40

(R)-(+)-5-(1-Ethyl-3-phenylprop-2-ynyl)-2,2-dimethyl-1,3-dioxane-4,6-dione

A solution of copper (II) acetate monohydrate (10 mg, 0.050 mmol) in water (0.2 ml) was treated with sodium (L)-ascorbate (20 mg, 0.10 mmol), the mixture was stirred until the mixture was turned bright orange (3 min). Subsequently, (R,M)-3-{[4-(2-diphenylphosphanyl-7-methoxy-naphthalen-1-yl)-phthalazin-1-ylamino]-phenyl-methyl}-pentan-3-ol (1st diastereomer, 33.1 mg, 0.050 mmol) and phenylacetylene (0.275 ml, 2.5 mmol) were added, the resulting mixture was stirred for 10 min at 23° C., cooled to 0° C., stirred for 5 min and treated with 5-(1-propylidene)-2,2-dimethyl-1,3-dioxane-4,6-dione (46 mg, 0.25 mmol). The reaction mixture was stirred vigorously at 0° C. for 24 hrs, diluted with dichloromethane (2 ml) and subjected directly to flash chromatography on silica gel (hexane/EtOAc 3:1-2:1) to give 59 mg of the pure title compound as a white solid. (yield: 83%)

mp: 105-110° C.

$[\alpha]_D^{25}$=20.5 (c=0.54, CHCl$_3$).

The other spectroscopic data was in agreement with the data reported in the literature (J. Am. Chem. Soc., 2003, 125, 6054-6055)

The title compound was treated with aniline in N,N-dimethylformamide for 1 hr at 100° C. to give (R)-3-ethyl-5-phenyl-4-pentynanilide, which was subjected to a chiral analysis with HPLC. The optical purity was 82% ee.

HPLC conditions:

column: Chiralcel OD-H (25 cm×4.6 mm, Daicel) and Chiralcel OD-H (15 cm×4.6 mm, Daicel), mobile phase: 87% hexane/13% iPrOH, flow rate: 0.7 ml/min, detector: 254 nm, retention time: (major)=27.0 min, (minor)=33.5 min.

Example 41

(S)-(+)-5-(1,3-Diphenylprop-2-ynyl)-2,2-dimethyl-1,3-dioxane-4,6-dione

A solution of copper (II) acetate monohydrate (20 mg, 0.10 mmol) in water (0.4 ml) was treated with sodium (L)-ascorbate (40 mg, 0.20 mmol), the mixture was stirred until the mixture was turned bright orange (3 min). Subsequently, (R,M)-3-{[4-(2-diphenylphosphanyl-7-methoxy-naphthalen-1-yl)-phthalazin-1-ylamino]-phenyl-methyl}-pentan-3-ol (1st diastereomer, 66.2 mg, 0.10 mmol) and phenylacetylene (0.55 ml, 5.0 mmol) were added, the resulting mixture was stirred for 10 min at 23° C., cooled to 0° C., stirred for 5 min and treated with 5-benzylidene-2,2-dimethyl-1,3-dioxane-4,6-dione (116 mg, 0.50 mmol). The reaction mixture was stirred vigorously at 0° C. for 66 hrs, diluted with dichloromethane (2 ml) and subjected directly to flash chromatography on silica gel (hexane/EtOAc 3:1→1:1) to give 110 mg of the pure title compound as a white solid. (yield: 64%)

mp: 153-156° C. (decomposition).

$[\alpha]_D^{27}$=59.5 (c=0.31, CHCl$_3$).

The other spectroscopic data was in agreement with the data reported in the literature (J. Am. Chem. Soc., 2003, 125, 6054-6055).

The title compound was treated with aniline in N,N-dimethylformamide for 1 hr at 100° C. to give (R)-3,5-diphenyl-4-pentynanilide, which was subjected to a chiral analysis with HPLC. The optical purity was 83% ee.

HPLC conditions:

column:-Chiralcel OD-H (25 cm×4.6 mm, Daicel), mobile phase: 87% hexane/13% iPrOH, flow rate: 0.7 ml/min, detector: 254 nm, retention time: (minor)=21.5 min, (major)=24.4 min.

The absolute configuration was determined by converting the title compound into (S)-methyl-3,5-diphenyl-2-methoxycarbonyl-5-oxopentane (1. H$_2$, Pd/C, MeOH, rt; 2. cat. HCl, MeOH, reflux; 3. CrO$_3$, AcOH, rt), which was compared with the reported literature (J. Am. Chem. Soc., 1995, 117, 6194-6198).

Example 42

(S)-(+)-5-(3-Phenyl-1-m-tolylprop-2-ynyl)-2,2-dimethyl-1,3-dioxane-4,6-dione

A solution of copper (II) acetate monohydrate (20 mg, 0.10 mmol) in water (0.4 ml) was treated with sodium (L)-ascorbate (40 mg, 0.20 mmol), the mixture was stirred until the mixture was turned bright orange (3 min). Subsequently, (R,M)-3-{[4-(2-diphenylphosphanyl-7-methoxy-naphthalen-1-yl)-phthalazin-1-ylamino]-phenyl-methyl}-pentan-3-ol (1st diastereomer, 66.2 mg, 0.10 mmol) and phenylacetylene (0.55 ml, 5.0 mmol) were added, the resulting mixture was stirred for 10 min at 23° C., cooled to 0° C., stirred for 5 min and treated with 5-(3-methylbenzylidene)-2,2-dimethyl-1,3-dioxane-4,6-dione (123 mg, 0.50 mmol). The reaction mixture was stirred vigorously at 0° C. for 66 hrs, diluted with dichloromethane (2 ml) and subjected directly to flash chromatography on silica gel (hexane/EtOAc 3:1→1:1) to give 151 mg of the pure title compound as a white solid. (yield: 87%)

mp: 136-137° C. (decomposition).

$[\alpha]_D^{27}$=61.3 (c=0.53, CHCl$_3$).

$^1$H-NMR (300 MHz, CDCl$_3$) δ 1.63 (s, 3H), 1.74 (s, 3H), 2.38 (s, 3H), 4.00 (d, J=2.6, 1H), 5.12 (d, J=2.6, 1H), 7.11 (d, J=7.5, 1H), 7.26 (t, J=7.5, 1H), 7.30-7.33 (m, 3H), 7.43 (d, J=7.5, 2H), 7.46-7.51 (m, 2H).

$^{13}$C-NMR (75 MHz, CDCl$_3$) δ 21.7, 27.9, 28.4, 37.1., 52.9, 85.4, 86.3, 105.2, 122.7, 125.6, 128.1. 128.2, 128.3 128.5. 129.1, 131.7, 136.9, 138.1, 162.9, 163.7.

FTIR (thin film, cm$^{-1}$): 3003 (w), 1786 (m), 1749 (s), 1607 (w), 1490 (m), 1296 (s), 1205 (m), 1006 (m), 758 (m), 692 (m).

MS (ESI, neg.) calcd for C$_{22}$H$_{19}$O$_4^-$ (M–H$^+$) 347.1 found 347.2.

Anal. Calcd for C$_{22}$H$_{20}$O$_4$: C, 75.84; H, 5.79. Found: C, 75.66; H, 5.93.

The title compound was treated with aniline in N,N-dimethylformamide for 1 hr at 100° C. to give (R)-5-phenyl-3-(m-tolyl)-4-pentynanilide, which was subjected to a chiral analysis with HPLC. The optical purity was 90% ee.

HPLC conditions:

column: Chiralcel OD-H (25 cm×4.6 mm, Daicel), mobile phase: 87% hexane/13% iPrOH, flow rate: 0.7 ml/min, detector: 254 nm, retention time: (minor)=19.8 min, (major)=21.7 min.

The obtained solid (123 mg) was recrystallized from ethyl acetate (40° C.) to give white crystals (85 mg) whose optical purity was 98% ee. (recovery rate: 69%)

$[\alpha]_D^{30}$ =67.9 (c=0.53, CHCl$_3$)

mp: 136-137° C. (decomposition).

Example 43

(S)-5-(1-(4-Methoxyphenyl)-3-phenylprop-2-ynyl)-2,2-dimethyl-1,3-dioxane-4,6-dione A solution of copper (II) acetate monohydrate (10 mg, 0.050 mmol) in water (0.2 ml) was treated with sodium (L)-ascorbate (20 mg, 0.10 mmol), the mixture was stirred until the mixture was turned bright orange (3 min). Subsequently, (R,M)-3-{[4-(2-diphenylphosphanyl-7-methoxy-naphthalen-1-yl)-phthalazin-1-ylamino]-phenyl-methyl}-pentan-3-ol (1st diastereomer, 33.1 mg, 0.050 mmol) and phenylacetylene (0.275 ml, 2.5 mmol) were added, the resulting mixture was stirred for 10 min at 23° C., cooled to 0° C., stirred for 5 min and treated with 5-(4-methoxybenzylidene)-2,2-dimethyl-1,3-dioxane-4,6-dione (65.6 mg, 0.25 mmol). The reaction mixture was stirred vigorously at 0° C. for 64 hrs, diluted with dichloromethane (2 ml) and subjected directly to flash chromatography on silica gel (hexane/EtOAc 3:1→1:1) to give 25 mg of the pure title compound as a white solid. (yield: 27%)

The spectroscopic data was in agreement with the data reported in the literature (J. Am. Chem. Soc., 2003, 125, 6054-6055).

The title compound was treated with aniline in N,N-dimethylformamide for 1 hr at 100° C. to give (R)-3-(4-methoxyphenyl)-5-phenyl-4-pentynanilide, which was subjected to a chiral analysis with HPLC. The optical purity was 81% ee.

HPLC conditions:

Column: Chiralcel OD-H (25 cm×4.6 mm, Daicel), mobile phase: 87% hexane/13% iPrOH, flow rate: 1 ml/min, detector: 254 nm, retention time: (minor)=18.7 min, (major)=21.5 min.

Example 44

(S)-5-(1-(4-Bromophenyl)-3-phenylprop-2-ynyl)-2,2-dimethyl-1,3-dioxane-4,6-dione A solution of copper (II) acetate monohydrate (10 mg, 0.050 mmol) in water (0.2 ml) was treated with sodium (L)-ascorbate (20 mg, 0.10 mmol), the mixture was stirred until the mixture was turned bright orange (3 min). Subsequently, (R,M)-3-{[4-(2-diphenylphosphanyl-7-methoxy-naphthalen-1-yl)-phthalazin-1-ylamino]-phenyl-methyl}-pentan-3-ol (1st diastereomer, 33.1 mg, 0.050 mmol) and phenylacetylene (0.275 ml, 2.5 mmol) were added, the resulting mixture was stirred for 10 min at 23° C., cooled to 0° C., stirred for 5 min and treated with 5-(4-bromobenzylidene)-2,2-dimethyl-1,3-dioxane-4,6-dione (77.7 mg, 0.25 mmol). The reaction mixture was stirred vigorously at 0° C. for 42 hrs, diluted with dichloromethane (2 ml) and subjected directly to flash chromatography on silica gel (hexane/EtOAc 3:1→1:1) to give 53 mg of the pure title compound as a white solid. (Yield: 39%)

The spectroscopic data was in agreement with the data reported in the literature (J. Am. Chem. Soc., 2003, 125, 6054-6055).

The title compound was treated with aniline in N,N-dimethylformamide for 1 hr at 100° C. to give (R)-3-(4-bromophenyl)-5-phenyl-4-pentynanilide, which was subjected to a chiral analysis with HPLC. The optical purity was 80% ee.

HPLC conditions:
column: Chiralcel OD-H (25 cm×4.6 mm, Daicel) and Chiralcel OD-H (15 cm×4.6 mm, Daicel), mobile phase: 87% hexane/13% iPrOH, flow rate: 1 ml/min, detector: 254 nm, retention time: (minor)=14.8 min, (major)=19.6 min.

Example 45

(S)-5-(1-(Furan-2-yl)-3-phenylprop-2-ynyl)-2,2-dimethyl-1,3-dioxane-4,6-dione

A solution of copper (II) acetate monohydrate (10 mg, 0.050 mmol) in water (0.2 ml) was treated with sodium (L)-ascorbate (20 mg, 0.10 mmol), the mixture was stirred until the mixture was turned bright orange (3 min). Subsequently, (R,M)-3-{[4-(2-diphenylphosphanyl-7-methoxy-naphthalen-1-yl)-phthalazin-1-ylamino]-phenyl-methyl}-pentan-3-ol (1st diastereomer, 33.1 mg, 0.050 mmol) and phenylacetylene (0.275 ml, 2.5 mmol) were added, the resulting mixture was stirred for 10 min at 23° C., cooled to 0° C., stirred for 5 min and treated with 5-(2-furfurylidene)-2,2-dimethyl-1,3-dioxane-4,6-dione (55.6 mg, 0.25 mmol). The reaction mixture was stirred vigorously at 0° C. for 64 hrs, diluted with dichloromethane (2 ml) and subjected directly to flash chromatography on silica gel (hexane/EtOAc 3:1→1:1) to give 26 mg of the pure title compound as a white solid. (yield: 32%)

The spectroscopic data was in agreement with the data reported in the literature (J. Am. Chem. Soc., 2003, 125, 6054-6055).

The title compound was treated with aniline in N,N-dimethylformamide for 1 hr at 100° C. to give (R)-3-(furan-2-yl)-5-phenyl-4-pentynanilide, which was subjected to a chiral analysis with HPLC. The optical purity was 83% ee.

HPLC conditions:
column: Chiralcel OD-H (25 cm×4.6 mm, Daicel) and Chiralcel OD-H (15 cm×4.6 mm, Daicel), mobile phase: 93% hexane/7% iPrOH, flow rate: 0.7 ml/min, detector: 254 nm, retention time: (major)=72.4 min, (minor)=79.5 min.

INDUSTRIAL APPLICABILITY

An asymmetric transition metal complex containing the compound of the present invention as a ligand is a superior asymmetric catalyst for an asymmetric reaction, particularly asymmetric addition reaction, asymmetric conjugate addition reaction, asymmetric hydroboration reaction, asymmetric diboration reaction and the like. Particularly, when the asymmetric transition metal complex is used for, for example, an asymmetric conjugate addition reaction such as a production method of the compound (XXVII) from the compound (XXVI), the objective product having higher optical purity can be obtained even in the case the optical purity of the asymmetric transition metal complex to be used in the reaction is relatively low.

Therefore, an asymmetric reaction using the asymmetric transition metal complex as an asymmetric catalyst can be a production method useful for optically active synthetic intermediates for pharmaceutical agents (e.g., ibuprofen and the like), agricultural chemicals and the like.

This application is based on provisional patent application No. 60/578735 filed in the United States, the contents of which are hereby incorporated by reference.

What is claimed is:

1. A compound represented by the formula (I):

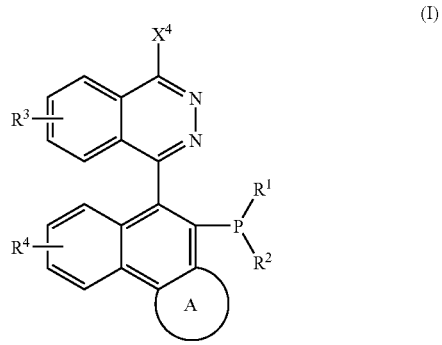

wherein ring A is void or a benzene ring optionally having substituent(s), $R^1$ and $R^2$ are each independently a phenyl group optionally having substituent(s), a cyclohexyl group, a 2-furyl group or a 3-furyl group, $R^3$ and $R^4$ are each independently a hydrogen atom, a halogen atom, a lower alkyl group, a lower alkoxy group, a cycloalkyl group optionally having substituent(s), an aralkyl group optionally having substituent(s) or an aryl group optionally having substituent(s), and X is a residue represented by —$OR^5$ or —$NHR^6$ wherein $R^5$ and $R^6$ are each a lower alkyl group optionally having substituent(s), an aralkyl group optionally having substituent(s), an aryl group optionally having substituent(s) or a heteroaryl group optionally having substituent(s), wherein each substituent of the benzene ring is independently a halogen atom, a lower alkyl group, a lower alkoxy group, a cycloalkyl group optionally having substituent(s), an aralkyl group optionally having substituent(s), or an aryl group optionally having substituent(s);

each substituent of the cycloalkyl group is independently a halogen atom, a lower alkyl group, a lower alkoxy group, a hydroxyl group, an amino group, a nitro group, a cyano group, a carboxyl group, an alkoxycarbonyl group, an aryl group, an aralkyl group, or oxo;

each substituent of the phenyl, aryl, aralkyl, and heteroaryl group is independently a halogen atom, a lower alkyl group, a lower alkoxy group, a hydroxyl group, an amino group, a nitro group, a cyano group, a carboxyl group, an alkoxycarbonyl group, an aryl group, or an aralkyl group; and each substituent of the lower alkyl group is independently is a halogen atom, a lower alkoxy group, a hydroxyl group, oxo, an amino group, a nitro group, a cyano group, a carboxyl group, or an alkoxycarbonyl group.

2. The compound of claim 1, wherein $R^1$ and $R^2$ are each independently a phenyl group, a tolyl group or a cyclohexyl group.

3. The compound of claim 1, wherein $R^5$ or $R^6$ is a group having an asymmetric center.

4. The compound of claim 1, which is an optically active form.

5. An asymmetric transition metal complex comprising the compound of claim 4 as a ligand and a transition metal selected from Ru, Rh, Cu, and Ag, wherein the asymmetric transition metal complex is prepared by reacting the compound of formula (I) with a transition metal salt or a complex of a transition metal salt, wherein the transition metal salt or a complex thereof is selected from $CuX^1$, $Cu(X^1)_2$, $Rh(cod)_2X^1$, $(nbd)Rh(acac)$, $CyRu(X^1)_2$ and $AgX^1$ and wherein $X^1$ is a counter ion selected from a halogen atom, $BF_4$, acetoxy, $SbF_6$, $PF_6$ and $OSO_2CF_3$, and wherein cod represents 1,5-cyclooctadiene, nbd represents norbornadiene, Cy represents cymene, and acac represents acetylacetone.

6. A method of preparing an optically active compound represented by the following formula (V), which method comprises contacting a compound of formula (II):

$$R^7CHO \quad (II)$$

wherein $R^7$ is a lower alkyl group optionally having substituent(s), an aryl group optionally having substituent(s), a cycloalkyl group optionally having substituent(s), a lower alkenyl group optionally having substituent(s), a lower alkynyl group optionally having substituent(s), an aralkyl group optionally having substituent(s), or a heteroaryl group optionally having substituent(s), a compound of formula (III):

$$HNR^8R^9 \quad (III)$$

wherein $R^8$ and $R^9$ are each independently a lower alkyl group optionally having substituent(s), a lower alkenyl group optionally having substituent(s), a cycloalkyl group optionally having substituent(s), an aralkyl group optionally having substituent(s), an aryl group optionally having substituent(s), or a heteroaryl group optionally having substituent(s), or $R^8$ and $R^9$ may form, together with the adjacent nitrogen atom, an aliphatic nitrogen-containing heterocycle optionally having substituent(s), and a compound of formula (IV):

$$HC \equiv CR^{10} \quad (IV)$$

wherein $R^{10}$ is a hydrogen atom, a lower alkyl group optionally having substituent(s), an aryl group optionally having substituent(s), a trialkylsilyl group, a cycloalkyl group optionally having substituent(s), an aralkyl group optionally having substituent(s), or a heteroaryl group optionally having substituent(s), with an asymmetric transition metal complex, wherein the asymmetric transition metal complex is prepared by reacting an optically active compound of formula (I) of claim 1 with $CuX^1$, wherein $X^1$ is a counter ion selected from the group consisting of a halogen atom, $BF_4$, acetoxy, $SbF_6$, $PF_6$ and $OSO_2CF_3$ to form an optically active compound of formula (V):

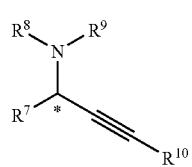

wherein $R^7$, $R^8$, $R^9$ and $R^{10}$ are as defined above and * shows an asymmetric carbon, wherein a substituted lower alkyl group has at least one substituent selected from the group consisting of halogen, lower alkoxy group, hydroxyl group, oxo, amino group, nitro group, cyano group, carboxyl group, and alkoxycarbonyl group, a substituted aryl group has at least one substituent selected from the group consisting of halogen, lower alkyl group, lower alkoxy group, hydroxyl group, amino group, nitro group, cyano group, carboxyl group, alkoxycarbonyl group, aryl group, and aralkyl group, a substituted cycloalkyl group has at least one substituent selected from the group consisting of halogen, lower alkyl group, lower alkoxy group, hydroxyl group, amino group, nitro group, cyano group, carboxyl group, alkoxycarbonyl group, aryl group, aralkyl group, and oxo, a substituted lower alkenyl group has at least one substituent selected from the group consisting of halogen, lower alkoxy group, hydroxyl group, oxo, amino group, nitro group, cyano group, carboxyl group, alkoxycarbonyl group, and aryl group, a substituted lower alkenyl group has at least one substituent selected from the group consisting of halogen, lower alkoxy group, hydroxyl group, oxo, amino group, nitro group, cyano group, carboxyl group, alkoxycarbonyl group, and aryl group, a substituted aralkyl group has at least one substituent selected from the group consisting of halogen, lower alkyl group, lower alkoxy group, hydroxyl group, amino group, nitro group, cyano group, carboxyl group, alkoxycarbonyl group, aryl group, aralkyl group, and oxo, a substituted heteroaryl group has at least one substituent selected from the group consisting of halogen, lower alkyl group, lower alkoxy group, hydroxyl group, amino group, nitro group, cyano group, carboxyl group, alkoxycarbonyl group, aryl group, and aralkyl group, and a substituted aliphatic nitrogen-containing heterocycle has at least one substituent selected from the group consisting of halogen, lower alkyl group, lower alkoxy group, hydroxyl group, amino group, nitro group, cyano group, carboxyl group, alkoxycarbonyl group, aryl group, aralkyl group, and oxo.

7. The method of claim 6, wherein $R^8$ and $R^9$ form a 4-piperidinonyl together with the adjacent nitrogen atom.

8. The method of claim 6, wherein the asymmetric transition metal complex is prepared by reacting the compound of formula (I), and $Cu(X^1)_2$ wherein $X^1$ is a counter ion selected from a halogen atom, $BF_4$, acetoxy, $SbF_6$, $PF_6$ and $OSO_2CF_3$ with a reducing agent selected from the group consisting of ascorbic acid or a salt thereof, triphenylphosphine, and tri(n-butyl)phosphine.

9. A method of preparing an optically active compound represented by the following formula (XXVII), which method comprises contacting a compound represented by the formula (XXVI):

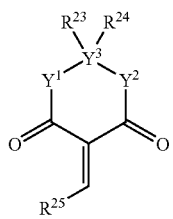

(XXVI)

wherein
$Y^1$ and $Y^2$ are each independently an oxygen atom or $NR^{26}$
  wherein $R^{26}$ is a lower alkyl group optionally having substituent(s), an aryl group optionally having substituent(s), an aralkyl group optionally having substituent(s) or a heteroaryl group optionally having substituent(s),
$Y^3$ is a carbon atom or a sulfur atom,
$R^{23}$ and $R^{24}$ are each independently a hydrogen atom, a lower alkyl group optionally having substituent(s), an aryl group optionally having substituent(s), an aralkyl group optionally having substituent(s) or a heteroaryl group optionally having substituent(s),
or $R^{23}$ and $R^{24}$ in combination can form an oxo,
or when $Y^3$ is a sulfur atom, then $R^{23}$ and $R^{24}$ can each independently be an oxo, and
$R^{25}$ is $-OCOR^{27}$, $-NR^{28}R^{29}$, $-SR^{30}$, a lower alkyl group optionally having substituent(s), a cycloalkyl group optionally having substituent(s), an aryl group optionally having substituent(s), an aralkyl group optionally having substituent(s), a heteroaryl group optionally having substituent(s), a heteroarylalkyl group optionally having substituent(s), or a heteroalkyl group optionally having substituent(s),
  wherein $R^{27}$, $R^{28}$, $R^{29}$ and $R^{30}$ are each independently a lower alkyl group optionally having substituent(s), an aryl group optionally having substituent(s), an aralkyl group optionally having substituent(s) or a heteroaryl group optionally having substituent(s), or $R^{28}$ and $R^{29}$ may form, together with the adjacent nitrogen atom, an aliphatic nitrogen-containing heterocycle optionally having substituent(s),
and
a compound represented by the formula (IV):

$$HC\equiv CR^{10} \qquad (IV)$$

wherein $R^{10}$ is a hydrogen atom, a lower alkyl group optionally having substituent(s), an aryl group optionally having substituent(s), a trialkylsilyl group, a cycloalkyl group optionally having substituent(s), an aralkyl group optionally having substituent(s) or a heteroaryl group optionally having substituent(s),
with an asymmetric transition metal complex,
  wherein the asymmetric transition metal complex is prepared by reacting an optically active compound of formula (I) of claim 1 and $Cu(X^1)_2$
    wherein $X^1$ is a counter ion selected from a halogen atom, $BF_4$, acetoxy, $SbF_6$, $PF_6$ and $OSO_2CF_3$
  with a reducing agent selected from the group consisting of ascorbic acid or a salt thereof, triphenylphosphine, and tri(n-butyl)phosphine to form the optically active compound represented by the formula (XXVII):

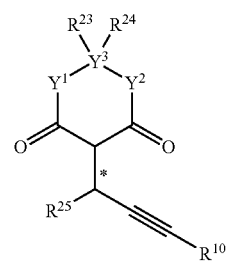

(XXVII)

wherein $Y^1$, $Y^2$, $Y^3$, $R^{10}$, $R^{23}$, $R^{24}$ and $R^{25}$ are as defined above and * shows an asymmetric carbon,
wherein
a substituted lower alkyl group has at least one substituent selected from the group consisting of halogen, lower alkoxy group, hydroxyl group, oxo, amino group, nitro group, cyano group, carboxyl group, and alkoxycarbonyl group,
a substituted heteroalkyl group has at least one substituent selected from the group consisting of halogen, lower alkoxy group, hydroxyl group, oxo, amino group, nitro group, cyano group, carboxyl group, and alkoxycarbonyl group,
a substituted aryl group has at least one substituent selected from the group consisting of halogen, lower alkyl group, lower alkoxy group, hydroxyl group, amino group, nitro group, cyano group, carboxyl group, alkoxycarbonyl group, aryl group, and aralkyl group,
a substituted cycloalkyl group has at least one substituent selected from the group consisting of halogen, lower alkyl group, lower alkoxy group, hydroxyl group, amino group, nitro group, cyano group, carboxyl group, alkoxycarbonyl group, aryl group, aralkyl group, and oxo,
a substituted aralkyl group has at least one substituent selected from the group consisting of halogen, lower alkyl group, lower alkoxy group, hydroxyl group, amino group, nitro group, cyano group, carboxyl group, alkoxycarbonyl group, aryl group, aralkyl group, and oxo,
a substituted heteroaryl group has at least one substituent selected from the group consisting of halogen, lower alkyl group, lower alkoxy group, hydroxyl group, amino group, nitro group, cyano group, carboxyl group, alkoxycarbonyl group, aryl group, and aralkyl group,
a substituted heteroarylalkyl group has at least one substituent selected from the group consisting of halogen, lower alkyl group, lower alkoxy group, hydroxyl group, amino group, nitro group, cyano group, carboxyl group, alkoxycarbonyl group, aryl group, aralkyl group, and oxo, and
a substituted aliphatic nitrogen-containing heterocycle has at least one substituent selected from the group consisting of halogen, lower alkyl group, lower alkoxy group, hydroxyl group, amino group, nitro group, cyano group, carboxyl group, alkoxycarbonyl group, aryl group, aralkyl group, and oxo.

10. A method of preparing an optically active compound represented by the following formula (VIII), which method comprises contacting a compound represented by the formula (VI):

$$R^{11}-HC=CH-R^{12} \quad (VI)$$

wherein $R^{11}$ is an aryl group optionally having substituent(s), a lower alkyl group optionally having substituent(s), a cycloalkyl group optionally having substituent(s), an aralkyl group optionally having substituent(s) or a heteroaryl group optionally having substituent(s), and $R^{12}$ is a hydrogen atom, a lower alkyl group optionally having substituent(s), a cycloalkyl group optionally having substituent(s), an aralkyl group optionally having substituent(s), an aryl group optionally having substituent(s) or a heteroaryl group optionally having substituent(s), and a boron compound represented by the formula (VII):

$$HBR^{13}R^{14} \quad (VII)$$

wherein $R^{13}$ and $R^{14}$ are each independently a hydrogen atom, a lower alkyl group, a lower alkoxy group, an aryl group, a heteroaryl group or an arylalkoxy group, or $R^{13}$ and $R^{14}$ may form a heterocycle or a fused ring thereof optionally having substituent(s) together with a boron atom bonded thereto, with an asymmetric transition metal complex, wherein the asymmetric transition metal complex is prepared by reacting an optically active compound of formula (I) of claim 1 with $Rh(cod)_2X^1$ wherein $X^1$ is a counter ion selected from a halogen atom, $BF_4$, acetoxy, $SbF_6$, $PF_6$ and $OSO_2CF_3$ and cod represents 1,5-cyclooctadiene to form the optically active compound represented by the formula (VIII):

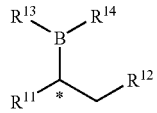

wherein $R^{11}$, $R^{12}$, $R^{13}$ and $R^{14}$ are as defined above and
* shows an asymmetric carbon, wherein a substituted lower alkyl group has at least one substituent selected from the group consisting of halogen, lower alkoxy group, hydroxyl group, oxo, amino group, nitro group, cyano group, carboxyl group, and alkoxycarbonyl group, a substituted aryl group has at least one substituent selected from the group consisting of halogen, lower alkyl group, lower alkoxy group, hydroxyl group, amino group, nitro group, cyano group, carboxyl group, alkoxycarbonyl group, aryl group, and aralkyl group, a substituted cycloalkyl group has at least one substituent selected from the group consisting of halogen, lower alkyl group, lower alkoxy group, hydroxyl group, amino group, nitro group, cyano group, carboxyl group, alkoxycarbonyl group, aryl group, aralkyl group, and oxo, a substituted aralkyl group has at least one substituent selected from the group consisting of halogen, lower alkyl group, lower alkoxy group, hydroxyl group, amino group, nitro group, cyano group, carboxyl group, alkoxycarbonyl group, aryl group, aralkyl group, and oxo, a substituted heteroaryl group has at least one substituent selected from the group consisting of halogen, lower alkyl group, lower alkoxy group, hydroxyl group, amino group, nitro group, cyano group, carboxyl group, alkoxycarbonyl group, aryl group, and aralkyl group, and a substituted heterocycle or fused ring of $R^{13}$ and $R^{14}$ has at least one substituent selected from the group consisting of halogen, lower alkyl group, lower alkoxy group, hydroxyl group, amino group, nitro group, cyano group, carboxyl group, alkoxycarbonyl group, aryl group, and aralkyl group.

11. A method of preparing an optically active compound represented by the following formula (XVII), which method comprises contacting a compound represented by the formula (XV):

wherein $R^{15}$ and $R^{16}$ are each independently a hydrogen atom, a lower alkyl group optionally having substituent(s), an aryl group optionally having substituent(s), a cycloalkyl group optionally having substituent(s), an aralkyl group optionally having substituent(s) or a heteroaryl group optionally having substituent(s) provided that $R^{15}$ and $R^{16}$ are not the same substituents, and $R^{17}$ is a hydrogen atom, a lower alkyl group optionally having substituent(s), an aryl group optionally having substituent(s), a cycloalkyl group optionally having substituent(s), an aralkyl group optionally having substituent(s) or a heteroaryl group optionally having substituent(s), or $R^{16}$ and $R^{17}$ may form a homocyclic ring or a fused ring thereof together with carbon atom bonded thereto, and a boron compound represented by the formula (XVI):

$$R^{18}R^{19}B-BR^{18}R^{19} \quad (XVI)$$

wherein $R^{18}$ and $R^{19}$ are each independently a hydrogen atom, a lower alkyl group, a lower alkoxy group, an aryl group, a heteroaryl group or an arylalkoxy group, or $R^{18}$ and $R^{19}$ may form a heterocycle or a fused ring thereof optionally having substituent(s) together with a boron atom bonded thereto, with an asymmetric transition metal complex, wherein the asymmetric transition metal complex is prepared by reacting an optically active compound of formula (I) of claim 1 with (nbd)Rh(acac) wherein nbd represents norbornadiene and acac represents acetylacetone to form the optically active compound represented by the formula (XVII):

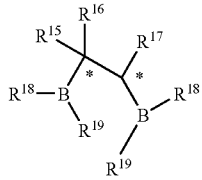

(XVII)

wherein $R^{15}$, $R^{16}$, $R^{17}$, $R^{18}$ and $R^{19}$ are as defined above, wherein a substituted lower alkyl group has at least one substituent selected from the group consisting of halogen, lower alkoxy group, hydroxyl group, oxo, amino group, nitro group, cyano group, carboxyl group, and alkoxycarbonyl group, a substituted aryl group has at least one substituent selected from the group consisting of halogen, lower alkyl group, lower alkoxy group, hydroxyl group, amino group, nitro group, cyano group, carboxyl group, alkoxycarbonyl group, aryl group, and aralkyl group, a substituted cycloalkyl group has at least one substituent selected from the group consisting of halogen, lower alkyl group, lower alkoxy group, hydroxyl group, amino group, nitro group, cyano group, carboxyl group, alkoxycarbonyl group, aryl group, aralkyl group, and oxo, a substituted aralkyl group has at least one substituent selected from the group consisting of halogen, lower alkyl group, lower alkoxy group, hydroxyl group, amino group, nitro group, cyano group, carboxyl group, alkoxycarbonyl group, aryl group, aralkyl group, and oxo, a substituted heteroaryl group has at least one substituent selected from the group consisting of halogen, lower alkyl group, lower alkoxy group, hydroxyl group, amino group, nitro group, cyano group, carboxyl group, alkoxycarbonyl group, aryl group, and aralkyl group, and a substituted heterocycle or fused ring of $R^{18}$ and $R^{19}$ has at least one substituent selected from the group consisting of halogen, lower alkyl group, lower alkoxy group, hydroxyl group, amino group, nitro group, cyano group, carboxyl group, alkoxycarbonyl group, aryl group, and aralkyl group.

12. A method of preparing the compound of claim 1, which comprises (i) reacting a compound represented by the formula (XIX):

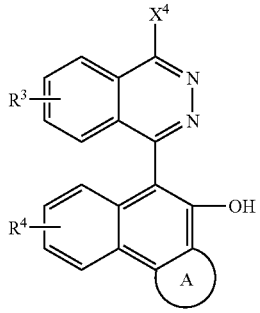

(XIX)

wherein ring A, $R^3$ and $R^4$ are as defined in claim 1 and $X^4$ is a halogen atom, a p-toluenesulfonyloxy, a methanesulfonyloxy or a trifluoromethanesulfonyloxy, with a compound represented by the formula (XX):

HOR$^5$ (XX)

or the formula (XXI):

H$_2$NR$^6$ (XXI), wherein $R^5$ and $R^6$ are as defined in claim 1, to convert the residue represented by $X^4$ to a residue represented by X wherein X is as defined in claim 1; then (ii) reacting the compound obtained in step (i) with trifluoromethanesulfonic anhydride in the presence of a base to convert the hydroxyl group to —OTf wherein Tf is a trifluoromethanesulfonyl group; to obtain a compound represented by the formula (XIX')

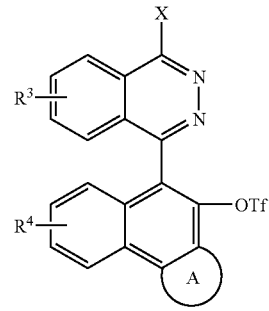

(XIX')

wherein each symbol is as defined above,
or (i) reacting a compound represented by the formula (XIX):

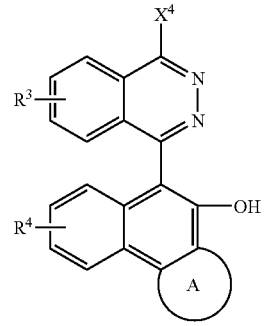

(XIX)

wherein ring A, $R^3$ and $R^4$ are as defined in claim 1 and $X^4$ is a halogen atom, a p-toluenesulfonyloxy, a methanesulfonyloxy or a trifluoromethanesulfonyloxy, with trifluoromethanesulfonic anhydride in the presence of a base to convert the hydroxyl group to —OTf wherein Tf is a trifluoromethanesulfonyl group; then (ii) reacting the compound obtained in step (i) with a compound represented by the formula (XX):

HOR$^5$ (XX)

or the formula (XXI):

H$_2$NR$^6$ (XXI), wherein $R^5$ and $R^6$ are as defined in claim 1,
to convert the residue represented by $X^4$ to a residue represented by X, wherein X is as defined in claim 1, to obtain a compound represented by the formula (XIX')

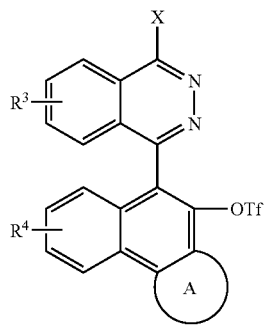

(XIX')

wherein each symbol is as defined above,
and
(iii) reacting the compound represented by the formula (XIX') with a compound represented by the formula (XXII):

$$HPR^1R^2 \qquad (XXII),$$

wherein $R^1$ and $R^2$ are as defined in claim 1, in the presence of a transition metal complex containing —$PR^1R^2$, wherein $R^1$ and $R^2$ are as defined in claim 1, to convert —OTf thereof to a residue represented by —$PR^1R^2$ wherein $R^1$ and $R^2$ are as defined in claim 1 to produce a compound represented by the formula (I).

13. The method of claim 12, wherein $R^5$ or $R^6$ is a residue having an asymmetric center.

14. The method of claim 13, which comprises after step (iii) separating by fractional recrystallization or silica gel chromatography a compound represented by the formula (I), which is a diastereomer mixture.

\* \* \* \* \*

UNITED STATES PATENT AND TRADEMARK OFFICE
CERTIFICATE OF CORRECTION

PATENT NO.         : 7,790,882 B2                                              Page 1 of 1
APPLICATION NO.    : 11/149643
DATED              : September 7, 2010
INVENTOR(S)        : Carreira It is certified that error appears in the above-identified patent and that said Letters Patent is hereby corrected as shown below:

In the claims:
Claim 1, at column 52, lines 5-19, formula (I) should read:

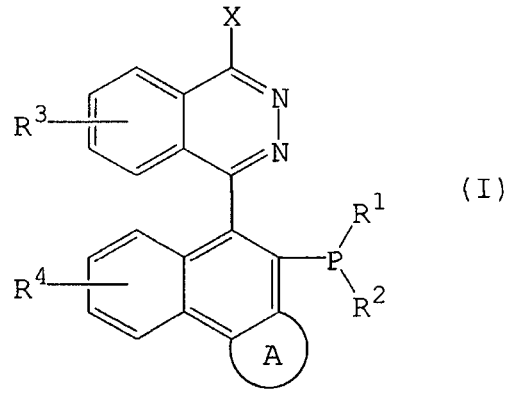

Claim 6, at column 54, line 29, "alkenyl" should read "alkynyl"

Signed and Sealed this
First Day of March, 2011

David J. Kappos
*Director of the United States Patent and Trademark Office*